(12) United States Patent (10) Patent No.: US 8,512,748 B2
Pearnchob et al. (45) Date of Patent: Aug. 20, 2013

(54) CONTROLLED RELEASE SYSTEM AND METHOD FOR MANUFACTURING THE SAME

(75) Inventors: Nantharat Pearnchob, Biberach (DE); Thomas Friedl, Ochsenhausen (DE); Karl Gerhard Wagner, Biberach (DE); Florian Sommer, Kisslegg (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 457 days.

(21) Appl. No.: 11/837,962

(22) Filed: Aug. 13, 2007

(65) Prior Publication Data

US 2008/0069873 A1 Mar. 20, 2008

(30) Foreign Application Priority Data

Aug. 25, 2006 (EP) .................................. 06017754

(51) Int. Cl.
*A61K 9/22* (2006.01)
*A61K 9/56* (2006.01)
*A61K 47/30* (2006.01)

(52) U.S. Cl.
USPC ...................... 424/468; 424/459; 514/772.3

(58) Field of Classification Search
USPC ................... 424/468, 459; 514/772.3
See application file for complete search history.

(56) References Cited

U.S. PATENT DOCUMENTS

| 3,096,248 A | 7/1963 | Rudzki |
| 3,406,178 A | 10/1968 | Crocker et al. |
| 3,472,854 A | 10/1969 | Archer |
| 4,200,641 A | 4/1980 | Vandenberk et al. |
| 4,367,217 A * | 1/1983 | Gruber et al. ................ 424/494 |
| 4,737,500 A | 4/1988 | Sorg |
| 4,792,452 A | 12/1988 | Howard et al. |
| 4,797,399 A | 1/1989 | Ueda et al. |
| 4,859,692 A | 8/1989 | Bernstein et al. |

(Continued)

FOREIGN PATENT DOCUMENTS

| BE | 904945 | 12/1986 |
| CA | 2455628 A1 | 2/2003 |

(Continued)

OTHER PUBLICATIONS

Aizenberg et al, "Cyproheptadine Treatment of Sexual Dysfunction Induced by Serotonin Reuptake Inhibitors," Clinical Neuropharmacology, vol. 18, No. 4, pp. 320-324, 1995 Lippincott-Raven Publishers, Philadelphia.
Archer, T.; "5-HT, Pain and Anxiety" Behavioural Pharmacology of 5-HT, pp. 299-300 (1989).
Chemical Abstract 88-98788c (Apr. 10, 1978),Awouters et al, "Oxatomide, a new orally active drug which inhibits both the release and the effects of allergic mediators."

(Continued)

*Primary Examiner* — Aradhana Sasan
(74) *Attorney, Agent, or Firm* — Michael P. Morris; Timothy X. Witkowski; Paula Wittmayer

(57) ABSTRACT

The invention is directed to a pharmaceutical controlled release system for administration, particularly oral administration, of active substances with pH-dependent solubilities, comprising
a) a core material containing or consisting of one or more pharmaceutically acceptable pH modifiers;
b) optionally an insulating layer,
c) a first layer containing or consisting of one or more pharmaceutically acceptable water-insoluble polymers;
d) a second layer containing or consisting of at least one active substance having a pH-dependent solubility;
e) a third layer containing or consisting of one or more pharmaceutically acceptable polymers having anionic or no ionic groups; and
f) optionally a fourth layer, preferably in form of an outer coating layer.
It is provided a pH-independent release profile of active substances having pH-dependent solubilities in vitro and vivo.

26 Claims, 14 Drawing Sheets

(56) References Cited

U.S. PATENT DOCUMENTS

| | | |
|---|---|---|
| 4,886,803 A | 12/1989 | Sueda et al. |
| 4,940,793 A | 7/1990 | Botrè et al. |
| 4,954,503 A | 9/1990 | Strupczewski et al. |
| 4,968,508 A | 11/1990 | Oren et al. |
| 5,002,948 A | 3/1991 | Perregaard et al. |
| 5,036,088 A | 7/1991 | Kitaura et al. |
| 5,225,417 A | 7/1993 | Dappen et al. |
| 5,405,642 A | 4/1995 | Gilis et al. |
| 5,407,686 A | 4/1995 | Patel et al. |
| 5,434,156 A | 7/1995 | Björk et al. |
| 5,492,907 A | 2/1996 | Pickar et al. |
| 5,552,412 A | 9/1996 | Cameron et al. |
| 5,576,318 A | 11/1996 | Bietti et al. |
| 5,591,743 A | 1/1997 | Patoiseau et al. |
| 5,854,290 A | 12/1998 | Arnsten et al. |
| 5,883,094 A | 3/1999 | Fliri et al. |
| 5,916,916 A | 6/1999 | Hauser et al. |
| 5,929,054 A | 7/1999 | Baker et al. |
| 5,932,249 A * | 8/1999 | Gruber et al. ............... 424/489 |
| 5,977,106 A | 11/1999 | Patoiseau et al. |
| 6,068,846 A | 5/2000 | Cho et al. |
| 6,083,947 A | 7/2000 | Granger et al. |
| 6,165,513 A | 12/2000 | Dansereau et al. |
| 6,187,340 B1 | 2/2001 | Fukuta et al. |
| 6,281,218 B1 | 8/2001 | Cereda et al. |
| 6,284,757 B1 | 9/2001 | Sanner |
| 6,346,548 B1 | 2/2002 | Miller et al. |
| 6,426,087 B1 | 7/2002 | Saslawski et al. |
| 6,482,841 B1 | 11/2002 | Letelier et al. |
| 6,521,623 B1 | 2/2003 | Cereda et al. |
| 6,586,435 B2 | 7/2003 | Cereda et al. |
| 6,627,646 B2 | 9/2003 | Bakale et al. |
| 6,680,071 B1 | 1/2004 | Johnson et al. |
| 7,151,103 B2 | 12/2006 | Borsini et al. |
| 7,183,410 B2 | 2/2007 | Bombarda et al. |
| 7,420,057 B2 | 9/2008 | Bombarda et al. |
| 2002/0001397 A1 | 1/2002 | Ishikawa et al. |
| 2002/0010216 A1 | 1/2002 | Rogosky et al. |
| 2002/0103208 A1 | 8/2002 | Cereda et al. |
| 2002/0151543 A1 | 10/2002 | Barberich et al. |
| 2003/0027823 A1 | 2/2003 | Cereda et al. |
| 2003/0060475 A1 | 3/2003 | Borsini |
| 2003/0083228 A1 | 5/2003 | Carpino et al. |
| 2003/0104980 A1 | 6/2003 | Borsini et al. |
| 2003/0119850 A1 | 6/2003 | Bombarda et al. |
| 2004/0023948 A1 | 2/2004 | Green et al. |
| 2004/0048877 A1 | 3/2004 | Friedl et al. |
| 2004/0116532 A1 | 6/2004 | Heacock et al. |
| 2004/0132697 A1 | 7/2004 | Thurlow et al. |
| 2004/0147581 A1 | 7/2004 | Taylor et al. |
| 2004/0180904 A1 | 9/2004 | Beck |
| 2004/0193452 A1 | 9/2004 | Berman |
| 2004/0235861 A1 | 11/2004 | Borsini |
| 2004/0258749 A1 | 12/2004 | Guldner et al. |
| 2005/0004105 A1 | 1/2005 | Leahy et al. |
| 2005/0037983 A1 | 2/2005 | Dinan et al. |
| 2005/0065158 A1 | 3/2005 | Naylor et al. |
| 2005/0095293 A1* | 5/2005 | Brauns et al. ............... 424/469 |
| 2005/0159430 A1 | 7/2005 | Bombarda et al. |
| 2005/0239798 A1 | 10/2005 | Pyke |
| 2005/0245539 A1 | 11/2005 | Mendla et al. |
| 2006/0014757 A1 | 1/2006 | Pyke |
| 2006/0025420 A1 | 2/2006 | Brauns et al. |
| 2006/0052391 A1 | 3/2006 | Dolsten |
| 2006/0160822 A1 | 7/2006 | Borsini |
| 2006/0199805 A1 | 9/2006 | Pyke et al. |
| 2006/0204486 A1 | 9/2006 | Pyke et al. |
| 2006/0211685 A1 | 9/2006 | Pyke et al. |
| 2006/0252773 A1 | 11/2006 | Ceci et al. |
| 2006/0258640 A1 | 11/2006 | Ceci et al. |
| 2006/0264511 A1 | 11/2006 | Pyke |
| 2006/0264512 A1 | 11/2006 | Pyke |
| 2007/0032654 A1 | 2/2007 | Bombarda et al. |
| 2007/0032655 A1 | 2/2007 | Bombarda et al. |
| 2007/0072872 A1 | 3/2007 | Borsini et al. |
| 2007/0105869 A1 | 5/2007 | Pollentier et al. |
| 2007/0123540 A1 | 5/2007 | Ceci |
| 2007/0196473 A1 | 8/2007 | Friedl et al. |
| 2007/0265276 A1 | 11/2007 | Pollentier et al. |
| 2008/0038346 A1* | 2/2008 | Eisenreich et al. ............ 424/468 |
| 2008/0038347 A1* | 2/2008 | Eisenreich et al. ............ 424/468 |
| 2008/0103155 A1 | 5/2008 | Mendla et al. |
| 2008/0119482 A1 | 5/2008 | Dolsten |
| 2008/0242678 A1 | 10/2008 | Ceci et al. |
| 2008/0242679 A1 | 10/2008 | Ceci |
| 2009/0023712 A1 | 1/2009 | Ferger et al. |
| 2009/0054458 A1 | 2/2009 | Bombarda et al. |
| 2009/0176698 A1 | 7/2009 | Baiker et al. |
| 2009/0239881 A1 | 9/2009 | Becker |
| 2009/0247546 A1 | 10/2009 | Ceci et al. |
| 2009/0312242 A1 | 12/2009 | Castro et al. |
| 2009/0318469 A1 | 12/2009 | Pyke et al. |

FOREIGN PATENT DOCUMENTS

| | | |
|---|---|---|
| CL | 1033-1999 | 5/1999 |
| CL | 2394-1999 | 10/1999 |
| CL | 1491-2001 | 6/2001 |
| CL | 2833-2001 | 11/2001 |
| CL | 418-2002 | 3/2002 |
| CL | 1706-2002 | 7/2002 |
| CL | 1878-2002 | 8/2002 |
| CL | 2389-2002 | 10/2002 |
| CL | 1751-2004 | 7/2004 |
| CL | 911-2005 | 4/2005 |
| CN | 1571670 A | 1/2005 |
| CN | 1655789 A | 8/2005 |
| DE | 3620643 A1 | 1/1987 |
| DE | 10209982.0 | 3/2002 |
| DE | 10138273 A1 | 2/2003 |
| EP | 0200322 A1 | 11/1986 |
| EP | 0376607 A1 | 7/1990 |
| EP | 0497985 A1 | 8/1992 |
| EP | 0526434 B1 | 2/1993 |
| EP | 0705832 A1 | 4/1996 |
| EP | 0816356 A1 | 1/1998 |
| EP | 0982030 A2 | 3/2000 |
| EP | 1256343 A1 | 11/2002 |
| EP | 1285658 | 2/2003 |
| EP | 1285658 A2 | 2/2003 |
| EP | 1014985 | 5/2003 |
| EP | 1518858 A1 | 3/2005 |
| EP | 1674102 | 6/2006 |
| GB | 2023594 A | 1/1980 |
| IE | 1992/1340 | 10/1992 |
| IL | 159151 | 2/2003 |
| IL | 160389 | 2/2004 |
| JP | 8-143476 | 6/1996 |
| RU | 93014306 A | 3/1995 |
| WO | WO 9202215 A1 | 8/1991 |
| WO | 92/03167 A1 | 3/1992 |
| WO | 92/19606 A1 | 11/1992 |
| WO | 93/03016 A1 | 2/1993 |
| WO | 95/01965 A1 | 1/1995 |
| WO | WO 95/19978 A1 | 7/1995 |
| WO | 95/34555 A1 | 12/1995 |
| WO | 96/05834 A1 | 2/1996 |
| WO | 96/16949 A1 | 6/1996 |
| WO | WO 98/19668 | * 5/1998 |
| WO | 98/33784 A1 | 8/1998 |
| WO | 98/42344 A1 | 10/1998 |
| WO | 99/19302 A1 | 4/1999 |
| WO | WO9959593 A1 | 5/1999 |
| WO | WO 99/59584 A1 | 11/1999 |
| WO | 00/28993 A1 | 5/2000 |
| WO | WO 00/24383 A1 | 5/2000 |
| WO | WO 00/63193 A1 | 10/2000 |
| WO | 00/64441 A2 | 11/2000 |
| WO | WO 00/67735 A2 | 11/2000 |
| WO | WO 01/00224 A1 | 1/2001 |
| WO | 01/12170 A2 | 2/2001 |
| WO | 01/21593 A1 | 3/2001 |
| WO | WO 02/00654 A1 | 1/2002 |
| WO | 02/24662 A1 | 3/2002 |
| WO | WO 02/41894 A2 | 5/2002 |

| | | |
|---|---|---|
| WO | WO 02/072586 A1 | 9/2002 |
| WO | 02/079143 A1 | 10/2002 |
| WO | WO 03/007949 A1 | 1/2003 |
| WO | 03/011396 A1 | 2/2003 |
| WO | 03/013539 A1 | 2/2003 |
| WO | 03/014079 A1 | 2/2003 |
| WO | 03/035072 A1 | 5/2003 |
| WO | WO 03074032 A1 | 9/2003 |
| WO | 03/097058 A1 | 11/2003 |
| WO | 2004/041259 A1 | 5/2004 |
| WO | 2004/045509 A2 | 6/2004 |
| WO | 2004/069339 A1 | 8/2004 |
| WO | 2005/007166 A1 | 1/2005 |
| WO | WO 2005/007166 A1 | 1/2005 |
| WO | 2005/044238 A1 | 5/2005 |
| WO | 2005/087207 A1 | 9/2005 |
| WO | 2005/102342 A1 | 11/2005 |
| WO | 2005/102343 A1 | 11/2005 |
| WO | 2006/010574 A1 | 2/2006 |
| WO | 2006/019715 A1 | 2/2006 |
| WO | WO 2006024471 A1 | 3/2006 |
| WO | 2006/096435 A1 | 9/2006 |
| WO | WO 2006/096434 A2 | 9/2006 |
| WO | 2006/125041 A1 | 11/2006 |
| WO | 2007/014929 A1 | 2/2007 |
| WO | 2007023325 A2 | 3/2007 |
| WO | 2007/048803 A1 | 5/2007 |
| WO | WO 2007048803 A1 | 5/2007 |
| WO | WO 2007090091 A2 | 8/2007 |
| WO | WO 2008/006839 A2 | 1/2008 |
| WO | WO 2008006838 A1 | 1/2008 |
| WO | WO 2008/022932 A2 | 2/2008 |
| WO | WO 2008019996 A2 | 2/2008 |
| WO | WO 2008116890 A2 | 10/2008 |

OTHER PUBLICATIONS

Backhauss et al., "A Mouse Model of Focal Cerebral Ischemia for Screening Neuroprotective Drug Effects," Journal of Pharmacological Methods 27, 1992, pp. 27-32.
Basson, R. et al; "Report of the international consensus development conference on female sexual dysfunction: definitions and classifications;" The Journal of Urology; vol. 163 pp. 888-893, Mar. 2000.
Baxter,G., "5-$HT_2$ Receptor Subtypes: a family re-united?", Trends in Pharmacological Sciences, Elsevier, Haywarth, GB, vol. 16, No. 3, Mar. 1995, pp. 105-110.
Beers, M.H. et al; The Merck Manual of Diagnosis and Therapy; 17th Ed., 1999, pp. 1595-1598.
Bernstein, J. et al; "Concomitant Polymorphs"; Angewandte Chemie, Int. Ed., 1999, pp. 3441-3461.
Bevan et al; "5-HT and sexual behaviour" Behavioural Pharmacology of 5-HT, pp. 33-34, 87-88 (1989).
Borsini, F. et al; Behavioral Effects of Flibanserin (BIMT 17), Sep. 1999, Pharmacology, Biochemistry and Behavior, vol. 64, Issue 1, abstract.
Borsini, F. et al; Behavioral Effects of Flibanserin (BIMT 17), Sep. 1999, Pharmacology Biochemistry and Behavior, vol. 64, Issue 1, pp. 137-146.
Borsini, F. et al; "Flibanserin," Drugs of the future, (1998) vol. 23 (1) pp. 9-16.
Borsini, F. et al; "BIMT 17, a 5-$HT_{2A}$ receptor antagonist and 5-$HT_{1A}$ receptor full agonist in rat cerebral cortex"; Naunyn-Schmiedeberg's Archives of Pharm., 1995, 352 pp. 276-282.
Borsini, F. et al; "Lack of interaction between flibanserin and antidepressants in inducing serotonergic syndrome in rats" International Journal of Neuropsychopharmacology (2001) pp. 9-15, vol. 4, No. 1, University Press, Cambridge, GB.
Borsini, F. et al, "Mechanism of action of flibanserin in the learned helplessness paradigm in rats," European Journal of Pharmacology 433:81-89 (2001).
Borsini, F. et al; "Pharmacology of Flibanserin" CNS Drug Reviews 2002; vol. 8, No. 2, pp. 117-142.
Borsini, F. et al., "BIMT 17: a putative antidepressant with a fast onset of action?" Psychopharmacology (1997) 134:378-386.
Brambilla et al., "Effect of Flibanserin (BIMT 17), fluoxetine 8-OH-DPAT and busprione on serotonin synthesis in rat brain," Europ. Neuropsychopharmacology, Vo. 10, No. 1, 1999, pp. 63-67.

Carey, John, "Viagra for Women?" Business Week.com (Dec. 28, 2006).
R. Cesana et al; "The effect of MIMT 17, a new potential antidepressant, in the forced swimming test in mice" Behavioral Pharmacology (1995) pp. 688-694, vol. 6. Rapid Science Publishers, GB.
Chalmers et al; "Corticotrophin-releasing factor receptors: from molecular biology to drug design" TiPS vol. 17 pp. 166-172, Apr. 1996.
Chemical Abstracts Service, Columbus 1978, Damir et al., "Hemodynamic effects of pharmacological block during acute overload of the heart" Database accession # 1978:591197 XP-002436715.
Chemical Abstract: Database, Collino, F. et al; accession No. 98:16650: "Mannich bases of bensimidazoles, benzotriazoles and other analogous compounds, with pharmacological activity."—XP 002197885.
Cloninger, C.R.; "A systematic method for clinical description and classification of personality variants" Arch. Gen. Psychiatry, vol. 44 pp. 573-588 (Jun. 1987).
Cools, A.R.; "Depression and psychosis" Behavioural Pharmacology of 5-HT, pp. 153-155 (1989).
Cremers and Boehm, "Non Erectile Dysfunction Application of Sildenafil", Herz, vol. 28, No. 4, pp. 325-333, 2003.
Crook, T. and Larkin, M.; "Effects of ondansertron in age-associated memory impairment" The role of ondansetron, a novel 5-HT3 antagonist, in the treatment of psychiatric disorders, 5th World Congress of Biochemical Psychiatry, pp. 21-23 (1991).
Cyr, Monica et al; "Nefazodone: Its place among antidepressants," Annals of Pharmacotherapy, vol. 30 No. 9 pp. 1006-1012; 1996.
Chemical Abstract 118-124537e Damour et al, "Preparation and formulation of 1[(4-phenylpiperazino)alkyl]benzimidazolin-2-ones and analogs as serotonin $S_2$ antagonists" ( Mar. 29, 1993).
Darlington, C.; "Flibanserin Boehringer Ingelheim Corp."; Current Opinion in CPNS investigational drugs vol. 1, No. 4, 1999, pp. 510-513; Pharma Press Ltd, London, GB.
DeVry, J.;"5-$HT_{1A}$ receptors in psychopathology and the mechanism of action of clinically effective therapeutic agents" Drug News and Perspectives 1996, vol. 9 No. 5 pp. 270-280.
Deangelis, L.; "5-$HT_{2A}$ antagonists in psychiatric disorders;" Current Opinion in Investigational Drugs 2002; vol. 3 No. 1 pp. 106-112; ISSN: 1472-4472.
Dimmock, P. et al; "Efficacy of selective serotonin-reuptake inhibitors in premenstrual syndrome: A systematic review" The Lancet, vol. 356, No. 9236 pp. 1131-1136, Sep. 30, 2000.
Fourcroy, Jean L. ; "Female sexual dysfunction: potential for pharmaotherapy" Drugs 2003, vol. 63 No. 14 pp. 1445-1457.
Frampton, et al; "Pentoxifylline ( Oxpentifylline) A Review of its Therapeutic Efficacy in the Management of Peripheral Vascular and Cerebrovascular Disorders;" (Drug Evaluation) Drugs and Aging 7 (6) pp. 480-503, 1995.
Fujikura et al; "Effects of naftidrofuryl oxalate, a 5-HT2 antagonist, on neuronal damage and local cerebral blood flow following transient cerebral ischemia in gerbils;" Brain Research 636 (1994) pp. 103-106.
Geyer, M.; "5-$HT_2$ antagonists increase tactile startle habituation in an animal model of habituation deficit in schizophrenia" Behavioural Pharmacology of 5-HT, pp. 243-246 (1989).
Giron, D; "Thermal analysis and calorimetric methods in the characterisation of polymorphs and solvates"; Thermochimica Acta, Elsevier Science; 248; 1995; pp. 1-59.
Goa, et al; "Buspirone. A preliminary review of its pharmacological properties and therapeutic efficacy as an anxiolytic;" Drugs 1986 vol. 32 pp. 114-129.
Gonzales, "Natural Compound May Offer New Treatment for Chronic Pain" NIDA Notes, vol. 16, No. 3—Aug. 2001, www.nida.nih.gov/NIDA_Notes/NNVol16N3/Natural.htm.
Gould;"Salt selection for basic drugs;" International Journal of Pharmaceutics; vol. 33, Issue 1-3, pp. 201-217, Nov. 1986.
Greene, T.; "Protective groups in organic synthesis:", Harvard University pp. 10-17 (1981), Wiley-Interscience Publication).
Hansenne, M. et al; "Harm avoidance dimension of the tridimensional personality questionnaire and serotonin-1A activity in depressed patients;" Biol. Psychiatry 1997, vol. 42 pp. 959-961.

Invernizzi et al,"Flibanserin, a potential antidepressant drug, lowers 5-HT and raises dopamine and noradrenaline in the rat prefrontal cortex dialysate: role of 5-$HT_{1A}$ receptors"; British Journal of Pharmacology, vol. 139 pp. 1281-1288, Jun. 2003.
Kleven, M., "Modification of behavioral effects of 8-hydroxy-2-(di-n-propylamino) tetralin following chronic ethanol consumption in the rat: evidence for the involvement of 5-$HT_{1A}$ receptors in ethanol dependence.", European Journal of Pharmacology, 1995, vol. 281, No. 3, pp. 219-228.
CAPLUS abstract 1999:285050, Koba, "Involvement of peripheral 5-$HT_{2A}$ receptor activation in pain behavior evoked by formalin paw injection in the rat," Kyushu Shika Gakkai Zaahi 53(1):253-60 (1999).
Lammers, GJ. et al; "Ritanserin, a 5-$HT_2$ receptor blocker, as add on treatment in narcolepsy;" Sleep 1991, vol. 14, No. 2 pp. 130-132.
Leonard, B.E.; "Sub-types of serotonin receptors: biochemical changes and pharmacological consequences" International Clinical Psychopharmacology 7, pp. 13-21 (1992).
Lyrer, "Neue Ansatze in der Akutbehandlung des zerebrovaskularen Insultes(New Approaches in the Acute Treatment of Cerebrovascular Insult)" Schweiz. Med. Wochenschr. vol. 124 No. 45 pp. 2005-2012 (1994).
Marazziti, Donatella et al; "Region-dependent effects of flibanserin and buspirone on adenylyl cyclase activity in the human brain" Int'l Journal of Neuropsychopharmacology, Jun. 2002, p. 131-140, vol. 5, No. 2.
Martindale: "Anxiolytic Sedatives Hypnotics and Antipsychotics" The complete drug reference, 1999, p. 635, Pharmaceutial Press, London 32.
McCall, RB. et al; "Role of serotonin 1A and serotonin 2 receptors in the central regulation of the cardiovascular system;" Pharmacological Reviews 1994, vol. 46 No. 3 pp. 231-243.
Merriam Webster New Collegiate Dictionary, definition of Diagnosis, 1981, p. 311.
Meston and Gorzalka, "Psychoactive Drugs and Human Sexual Behavior: The Role of Serotonergic Activity," Journal of Psychoactive Drugs, vol. 24(1), Jan.-Mar. 1992 pp. 1-40.
"The Merck Manual of diagnosis and therapy", Merck Research Laboratories, USA 1999, p. 1410, col. 1-p. 1413, col. 2, paragraph 1; p. 1412, tables 173-2 XP-002439435.
Miranda, et al., Dexketoprofen-Induced antinociception in animal models of acute pain: Synergy with morphine and paracetamol; Neuropharmacology 52 (2007) 291-296.
Moynihan, R., "The making of disease: female sexual dysfunction" British Medical Journal, 2003. vol. 326, pp. 45-47.
Nadeson, et al., "Antinociceptive role of 5-$HT_{1A}$ receptors in rat spinal cord" Laboratory Investigations, British Journal of Anaesthesia 88(5):679-84 (2002).
Okamoto et al., "5-HT2A receptor subtype in the peripheral branch of sensory fibers is involved in the potentiation of inflammatory pain in rats," Pain 99 (2002) 133-143.
Petkov, V.D. et al; "Participation of different 5-HT receptors in the memory process in rats and its modulation by the serotonin depletory p-chlorophenylalanine;" Acta Neurobiol. Exp. 1995 vol. 55 pp. 243-252.
Philips & Slaughter; "Depression and Sexual Desire," American Family Physician, vol. 62/No. 4, Aug. 15, 2000.
Podhorna, J. et al; "Flibanserin has anxiolytic effects without locomotor side effects in the infant rat ultrasonic vocalization model of anxiety;" British Journal of Pharacology (2000) vol. 130 No. 4 pp. 739-746.
Prehn et al; "Neuroprotective properties of 5-HT1A receptor agonists in rodent models of focal and global cerebral ischemia;" European Journal of Pharmacology, 203 (1991) 213-222.
Prehn et al., "Effects of serotonergic drugs in experimental brain ischemia: evidence for a protective role of serotonin in cerebral ischemia;" Brain Research 630 (1993) pp. 10-20.
Riekkinen et al; "The effects of increased serotonergic and decreased cholinergic activities on spatial navigation performance in rats" Pharmacology Biochemistry & Behavior, vol. 39 pp. 25-29 (1991).
Rueter, L.E. et al; "Electrophysiological examination of the effects of sustained flibanserin administration on serotonin receptors in rat brain;" British J. of Pharm, 1999, vol. 126, No. 3, pp. 627-638.

Risch, S. Craig et al; "Neurochemical alterations of serotonergic neuronal systems in depression;" J. Clin. Psychiatry 1992, vol. 53 No. 10 Suppl. 3-7.
Robinson, D.S. "Serotonin receptor subtypes and affective disorders;" Clinical Neuropharmacology 1993, vol. 16 No. Suppl. 3 pp. S1-S5.
Rosland et al., "The formalin test in mice: effect of formalin concentration," Pain 42 (1990) 235-242.
Shibata et al., "Ischemia-induced impairment of 2-deoxyglucose uptake and CA1 field potentials in rat hippocampal slices: protection by 5-HT1A receptor agonists and 5-HT2 receptor antagonists;" European Journal of Pharmacology, 229 (1992) pp. 21-29.
Shipton, B. et al., "Valvular heart disease: review and update," American Family PhysicianJun. 1, 2001, vol. 63 # 11, pp. 2201-2208.
Sietsema, D. et al, "From Taboo to Treatment?" Good Clinical Practice Journal, Jan. 2005, vol. 12, # 1, pp. 23-27.
Spine-health.com, Types of Back Pain: Acute Pain, Chronic Pain and Neuropathic Pain, www.spine-health.com/topics/cd/chronic_pain/chronicpain02.html, Oct. 2, 2007.
Steiner, M., Recognition of Premenstrual Dysphoric Disorder and Its Treatment; The Lancet, vol. 356, No. 9236, Sep. 30, 2000, pp. 1126-1127.
Vandenberk et al; Piperazine and piperidine derivatives, Chemical Abstract 88-50920n (Jan. 30, 1978).
Walsh K. et al., "Sexual dysfunction in the older women and overview of the current understanding and management" Drugs and Aging, 2004, vol. 21, # 10 pp. 655-675.
Zajecka, John et al; "Sexual function and satisfaction in the treatment of chronic major depression with nefazodone, psychotherapy, and their combination;" Journal Clin. Psychiatry, vol. 63 No. 8 pp. 709-716, Aug. 2002.
U.S. Appl. No. 11/956,949, filed Dec. 14, 2007, D. Lewis-D'Agostino et al.
U.S. Appl. No. 11/960,957, filed Dec. 20, 2007, Klaus Mendla et al.
U.S. Appl. No. 11/940,655, filed Nov. 15, 2007; Dolsten, Mikael.
U.S. Appl. No. 11/997,567, filed Feb. 1, 2008, Ceci, Angelo.
U.S. Appl. No. 12/280,804, filed Aug. 27, 2008, Ceci.
U.S. Appl. No. 12/306,946, filed Dec. 29, 2008, Becker.
U.S. Appl. No. 12/306,945, filed Dec. 29, 2008, Pyke.
U.S. Appl. No. 12/306,878, filed Dec. 29, 2008, Castrol et al.
Alexander et al., J. of Am. Acad. of Nurse Practitioners, 2007, 19:152-163.
Guilleminault et al., Atypical Sexual Behavior During Sleep, Phychosomatic Med., 2002, 64:328-336.
Basson et al., Sexual psychophysiology and effects of sildenafil citrate in oestrogenised women with acquired genital arousal disorder and impaired orgasm: a randomised controlled trial, BJOG: an International Journal of Obstetrics and Gyn., Nov. 2003, 110:1014-1024.
Basson et al., Efficacy and Safety of Sildenafil Citrate in Women with Sexual Dysfunction Associated with Female Sexual Arousal Disorder, J Women's Health & Gender-Based Medicine, Nov. 4, 2002 11:367-77.
Black et al., Inappropriate sexual behaviors in dementia, J of Geriatric Psychiatry & Neurology, Sep. 2005, 18(3):155-162.
Clayton, Epidemiology and Neurobiology of Femal Sexual Dysfunction, J Sex Med., Nov. 4, 2007, Suppl 4:260-8.
Clayton et al., Burden of phase-specific sexual dysfunction with SSRIs, J Affect Disord., Mar. 2006, 91(1):27-32.
Clayton et al., Prevalence of Sexual Dysfunction Among Newer Antidepressants, J. Clin. Psychiatry, 2002, 63(4):357-366.
CMU Pharmaceutical polymorphism, http://www.andrew.cmu.edu/user/suter/polymorph.html, internet p. 1-3 (2002): obtained Feb. 11, 2009.
Sexual Dysfunction and Hypotestosteronemia in Patients With Obstructive Sleep Apnea Syndrome and Its Effects With CPAP Therapy, http:...clinicaltrials.gov/ct2/show/NCT00832065, obtained Apr. 1, 2009, 4pgs.
Doelker et al., Crystalline modifications and polymorphism changes during drug manufacturing, Annales Pharmaceutiques Francaises, 2002, 60(3):161-169, Summary only.

Doelker et al., Physicochemical behavior or active substances. Consequences for the feasibility and stability of pharmaceutical forms, S.T.P. Pharma Pratiques, 1999, 9(5):399-409, Summary only.
Engleson, Concise Encyclopedia Chemistry, 1993, pp. 872-873.
Giraldi et al., Physiology of Female Sexual Function. Animal Models, J Sex Med, 2004, 1(3):237-253.
Girgis et al., A double-blind trial of clomipramine in premature ejaculation, Andrologia, Jul.-Aug. 1982, 14(4):364-8.
Goldfischer et al., Selected 2008 Abstracts from the International Society for the Study of Women's Sexual Health, J. Sex. Med., 2008, 5(suppl. 3):159-160.
Goodman, An assessment of clomipramine (Anafranil) in the treatment of premature ejaculation, J Int Med Res., 1980; 8(Suppl 3):53-9.
Haensel et al., Fluoxetine and premature ejaculation: A double-blind, crossover, placebo-controlled study, J Clin Psychopharmacology, 1998, 18:72-77.
Haensel et al., Clomipramine and sexual function in men with premature ejaculation and controls, J Urology, Oct. 1996, 156(B193):1310-1315.
Jain et al., Polymorphism in Pharmacy, Indian Drugs, 1986, 23(6):315-329.
Kandeel et al., Male Sexual Function and its Disorders: Physiology, Pathophysiology, Clinical investigation, and Treatment, Endocrine Reviews, 2001, 22(3):342-388 at 370.
Kennedy et al., Antidepressant-Induced Sexual Dysfunction During Treatment with Moclobemide, Paroxetine, Sertraline, and Venlafaxine, J Clin Psychiatry, 2000; 61:276-81.
Kennedy et al., Sexual dysfunction before antidepressant therapy in major depression, J. Affective Disorders, 1999, 56:201-208.
Konarski et al., Effects of Acute Flibanserin on FDG-PET Brain Glucose Metabolism in Men with Major Depressive Disorder, Aug. 2008 Barcelona meeting of the European College of Nueropsychopharmacology, 3 pgs. (poster-abstract).
McKenna, Neural Circuitry Involved in Sexual Function, J Spinal Cord Med., 2001, 24:148-154.
McMahon et al., Efficacy of type-5 phosphodiesterase inhibitors in the drug treatment of premature ejaculation: a systematic review, BJU Int., 2006, 98:259-72.
Montejo-Gonzales et al., SSRI-induced sexual dysfunction: fluoxetine, paroxetine, sertraline, and fluvoxamine in a prospective, multicenter, and descriptive clinical study of 344 patients, J Sex Marital, 1997 Fall; 23(3):176-94.
Muzaffar et al., J. Pharmacy, 1979, 1(1):59-66.
Nurnberg et al., Sildenafil for Sexual Dysfunction in Women Taking Antidepressants, Am J Psychiatry, October—Letters to the Editor, 1999, 156(10):1664.
Nurnberg et al., Sildenafil Treatment of Women with Antidepressant-Associated Sexual Dysfunction, JAMA, Jul. 2008, 300(4):395-404.
Pfaus et al., What can animal models tell us about human sexual response?, Annu Rev Sex Res, 2003, 14:1-63.
Porter, Remingtons, 1990, Chpt 90, pp. 1666-1675.
Pryor et al., Efficacy and tolerability of dapoxetine in treatment of premature ejaculation: an integrated analysis of two double-blind, randomized controlled trials, Lancet, 2006, 368(9539):929-37.
Pyke et al., Flibanserin: A Novel Centrally Acting Agent that is not an Effective Antidepressant but has Potential to Treat Decreased Sexual Desire in Women, APA, May 2008, 1 pg. (accepted poster).
Pyke et al., Flibanserin: A Novel Centrally Acting Agent that is not an Effective Antidepressant but has Potential to Treat Decreased Sexual Desire in Women, APA, May 2008, 1 pg. (accepted abstract).
Rapkin, General Gynecology, 2007, 196:97-106.
Rendell et al., Sildenafil for Treatment of Erectile Dysfunction in Men with Diabetes, JAMA, 1999, 281:421-426.
Rosen et al., Effects of SSRIs on sexual function: a critical review, J Clin Psychopharmacol., Feb. 1999 19(1):67-85.
Rosen et al., PDE-5 inhibition and sexual response: Pharmacological mechanisms and clinical outcomes, Annual Review of Sex Res, 2002, pp. 36-88.
Rosen, Sexual pharmacology in the 21st century, J Gend Specif Med., Jul.-Aug. 2000, 3(5):45-52.
Rowland, Neurobiology of Sexual Response in Men and Women, 1:CNS Spectr., Aug. 2006, 11(8 Suppl 9):6-12.
Rubenstein, Pharmaceutics: The Science of Dosage Form Design, ed. Aulton, 1988, pp. 304-321.
Martin, Sexsomnia, http://lakesidepress.com/pulmonary/ Sleep/sexsomnia html, obtianed Apr. 1, 2009, 5pgs.
Stearns et al., J. of Clin. Oncology, 2002, 20(6):1436-1438.
Stedman's Medical Dictionary definition "Prevention," 2000, 28th Ed., 3 pgs., Lippincott Williams & Wilkins.
Stoleru et al., Brain processing of visual sexual stimuli in men with hypoactive sexual desire disorder, Psychiatry Res.: Neuroimaging, 2003, 124(2):67-86.
Clayton et al., Validation of the Decreased Sexual Desire Screener (DSDS): a Brief Diagnostic Instrument for Generalized, Acquired Hypoactive Sexual Desire Disorder in Women, International Society for the Study of Womens Sexual Health (ISSWSH) annual meeting, 2007, 2 pgs. (poster and abstract).
Wunderlich et al., Using e-Diaries to Measure Sexual Desire in Women with Hypoactive Sexual Desire Disorder, International Society for the Study of Womens Sexual Health (ISSWSH) annual meeting, 2007, 11 pgs. (Oral Presentation).
Clayton et al., Validation of the Sexual Interest and Desire Inventory-Female (SIDI-F) in North American Women, International Society for the Study of Womens Sexual Health (ISSWSH) annual meeting, 2007, 3 pgs. (poster and abstract).
Clayton et al., Validity of Sexual Distress Scales vs Electronic Diary in Women with Decreased Sexual Desire , American College of Obstetrics and Gynecologists (ACOG) annual meeting, 2007, 1 pg. (abstract only).
Clayton et al., Validating the Sexual Interest and Desire Inventory (SIDI-F) in North American Women , American College of Obstetrics and Gynecologists (ACOG) annual meeting, 2007, 1 pg. (abstract only).
Clayton et al., Validation of the Sexual Interest and Desire Inventory-Female (SIDI-F) in North American Women, American Psychiatric Association (APA) annual meeting, 2007, 2 pgs. (poster and abstract).
Tignol et al., Using e-Diaries to Measure Sexual Desire in Women with Hypoactive Sexual Desire Disorder, European Society for Sexual Medicine (ESSM) annual meeting, 2007, 9 pgs. (oral presentation).
Clayton, Baseline characteristics of patients enrolled in three Phase III North American trials of flibanserin in premenopausal women with Hypoactive Sexual Desire Disorder, Joint Congress of the European and International Societies of Sexual Medicine (ESSM/ISSM) 2008, 10 pgs. (oral presentation).
Clayton et al., Baseline characteristics of patients enrolled in three Phase III North American trials of flibanserin in premenopausal women with Hypoactive Sexual Desire Disorder, Joint Congress of the European and International Societies of Sexual Medicine (ESSM/ISSM) 2008, 1 pgs. (abstract).
Clayton et al., Baseline characteristics of patients enrolled in three Phase III North American trials of flibanserin in premenopausal women with Hypoactive Sexual Desire Disorder, International Society for the Study of Womens Sexual Health (ISSWSH) annual meeting 2009, poster, 2 pgs. (poster and abstract).
Clayton et al., Validation of the Decreased Sexual Desire Screener (DSDS): A Brief Diagnostic Instrument for Generalized Acquired Female Hypoactive Sexual Desire Disorder (HSDD); J. Sex Med., 2009, pp. 1-9. (epub ahead of print).
Dean, Decreased Sexual Desire Screener© (DSDS©) for Diagnosis of Hypoactive Sexual Desire Disorder in Women, WONCA Europe conference, 2008, 8 pgs. (oral presentation).
Dean et al., Decreased Sexual Desire Screener© (DSDS©) for Diagnosis of Hypoactive Sexual Desire Disorder in Women, WONCA Europe conference, 2008, 1 pg. (abstract).
Derogatis et al., Validation of Sexual Distress Scales and Electronic Diary in Women with Hypoactive Sexual Desire Disorder, International Society for the Study of Womens Sexual Health (ISSWSH) annual meeting, 2007, 3 pgs. (poster and abstract).
Derogatis et al., Validation of Sexual Distress Scales and Electronic Diary in Women with Hypoactive Sexual Desire Disorder. American Psychiatric Association (APA) annual meeting, 2007, 2 pgs. (poster and abstract).

Derogatis et al., Content Validity of the Female Sexual Distress Scale-Revised (FSDS-R) in Women with Hypoactive Sexual Desire Disorder (HSDD), Joint Congress of the European and International Societies of Sexual Medicine (ESSM/ISSM) 2008, 5 pgs. (poster, oral presentation and abstract).

Derogatis et al., Validation of the Female Sexual Distress Scale Revised (FSDS-R) for assessing distress in women with Hypoactive Sexual Desire Disorder (HSDD), J Sex Med., 2008, 5:357-364.

Dennerstein et al., Differentiating Four Cognitive-Behavioral Types of Women with Low Sexual Desire, International Society for the Study of Womens Sexual Health (ISSWSH) annual meeting, 2007, 9 pgs. (Oral Presentation).

Dennerstein et al., Differentiating Four Cognitive-Behavioral Types of Women with Decreased Sexual Desire, International Society for the Study of Womens Sexual Health (ISSWSH) annual meeting, 2007, 2 pgs. (abstract).

Dennerstein et al., Differentiating Four Cognitive-Behavioral Types of Women with Decreased Sexual Desire, American Psychiatric Association (APA) annual meeting, 2007, 3 pgs. (poster and abstract).

Dennerstein et al., Differentiating Four Cognitive-Behavioral Types of Women with Decreased Sexual Desire, European Society for Sexual Medicine (ESSM) annual meeting, 2007, 3 pgs. (poster and abstract).

Dennerstein, Differentiating Four Cognitive-Behavioral Types of Women with Low Sexual Desire, European Society for Sexual Medicine (ESSM) annual meeting, 2007, 10 pgs. (oral presentation).

Dennerstein et al., Attitudes Towards Partner Interactions of Women With Characteristics of HSDD: Preliminary Results of a Multinational Study of 1,402 Women. International Society for the Study of Womens Sexual Health (ISSWSH) annual meeting, 2008, 12 pgs. (oral presentation and abstract).

Goldfischer et al., Validation of the Decreased Sexual Desire Screener (DSDS): a Brief Diagnostic Instrument for Generalized, Acquired Hypoactive Sexual Desire Disorder in Women, American Psychiatric Association (APA) annual meeting, 2007, 2 pgs. (poster and abstract).

Pyke et al., The ROSE Study: Placebo-controlled Randomized Withdrawal Trial of Flibanserin for Hypoactive Sexual Desire Disorder in Premenopausal Women, Sexual Medicine Society of North America (SMSNA) annual meeting, 2007, 1 pg. (poster).

Goldfischer et al., Efficacy of Continued Flibanserin Treatment on Sexual Desire and Satisfying Sexual Events in Premenopausal Women With HSDD: Results From the ROSE Study, International Society for the Study of Womens Sexual Health (ISSWSH) annual meeting, 2008, 1 pgs. (abstract).

Goldfischer et al., Efficacy of Continued Flibanserin Treatment on Distress Associated with Sexual Dysfunction in Premenopausal Women With HSDD: Results From the ROSE Study, International Society for the Study of Womens Sexual Health (ISSWSH) annual meeting, 2008, 2 pgs. (poster and abstract).

Goldfischer et al., Efficacy of Continued Flibanserin Treatment on Sexual Functioning in Premenopausal Women With HSDD: Results From the ROSE Study, International Society for the Study of Womens Sexual Health (ISSWSH) annual meeting, 2008, oral presentation, 1 pg. (abstract only).

Goldfischer et al., The ROSE Study: Placebo-controlled Randomized Withdrawal Trial of Flibanserin for Hypoactive Sexual Desire Disorder in Premenopausal Women, European Board and College of Obstetrics and Gynaecology (EBCOG) annual meeting, 2008, 1 pg. (abstract only).

Goldfischer et al., The ROSE Study: Placebo-controlled Randomized Withdrawal Trial of Flibanserin for Hypoactive Sexual Desire Disorder in Premenopausal Women. European Federation of Sexology (EFS), 2008, 7 pgs. (oral presentation and abstract).

Goldfischer et al., Decreased Sexual Desire Screener (DSDS) for Diagnosis of Hypoactive Sexual Desire Disorder in Women, American College of Obstetrics and Gynecologists (ACOG) annual meeting, 2008, 2 pgs. (poster and abstract).

Goldfischer et al., Efficacy of Continued Flibanserin Treatment in Premenopausal Women with Hypoactive Sexual Desire Disorder: Results from the ROSE Study, International Academy of Sex Research (IASR) annual meeting, 2008, 3 pgs. (poster and abstract).

Goldfischer et al., Safety and Tolerability of Flibanserin in Premenopausal Women with Hypoactive Sexual Desire Disorder: Results from the ROSE Study, International Academy of Sex Research (IASR) annual meeting, 2008, 3 pgs. (poster and abstract).

Goldfischer et al., Efficacy and Safety of Flibanserin in Premenopausal Women with Hypoactive Sexual Desire Disorder: Results from the Randomized Withdrawal ROSE Study, Institute on Psychiatric Services (IPS) annual meeting, 2008, 2 pgs. (poster and abstract).

Goldfischer et al., Decreased Sexual Desire Screener (DSDS) for Diagnosis of Hypoactive Sexual Desire Disorder in Women, Sexual Medicine Society of North America (SMSNA) annual meeting, 2008, 3 pgs. (poster and abstract).

Goldfischer et al., Efficacy and Safety of Flibanserin in Premenopausal Women with Hypoactive Sexual Desire Disorder: Results From the Randomized Withdrawal ROSE Study, Sexual Medicine Society of North America (SMSNA) annual meeting, 2008, 3 pgs. (poster and abstract).

Goldfischer, Efficacy of Continued Flibanserin Treatment in Premenopausal Women with Hypoactive Sexual Desire Disorder: Results From the ROSE Study, Joint Congress of the European and International Societies of Sexual Medicine (ESSM/ISSM), 2008, 10 pgs. (oral presentation).

Goldfischer et al., Efficacy of Continued Flibanserin Treatment in Premenopausal Women with Hypoactive Sexual Desire Disorder: Results From the ROSE Study, Joint Congress of the European and International Societies of Sexual Medicine (ESSM/ISSM), 2008, 2 pgs. (abstract).

Goldfischer et al., Safety and Tolerability of Continued Flibanserin Treatment in Premenopausal Women with Hypoactive Sexual Desire Disorder: Results From the ROSE Study, Joint Congress of the European and International Societies of Sexual Medicine (ESSM/ISSM), 2008, 2 pgs. (poster and abstract).

Goldstein et al., Differences in Patient-Physician Communication Regarding Hypoactive Sexual Desire Disorder (HSDD), Sexual Medicine Society of North America (SMSNA) annual meeting, 2007, 3 pgs. (poster and abstract).

Goldstein et al., Emotions Related to Distress in Patients with Hypoactive Sexual Desire Disorder: Results of Patient and Physician Interviews, Sexual Medicine Society of North America (SMSNA) annual meeting, 2007, 3 pgs. (poster and abstract).

Jolly et al., Design of Phase III Pivotal Trials of Flibanserin in Female Hypoactive Sexual Desire Disorder (HSDD), European Federation of Sexology (EFS), 2008, 2 pgs. (poster and abstract).

Konarski et al., Effects of Acute Flibanserin on FDG-PET Brain Glucose Metabolism in Men with Major Depressive Disorder, European College of Neuropsychopharmacology congress (ECNP), 2008, 3 pgs. (poster and abstract).

Nappi et al., Validation of the Sexual Interest and Desire Inventory-Female (SIDI-F) in European Women, European Federation of Sexology (EFS), 2008, 2 pgs. (poster and abstract).

Nappi, Decreased Sexual Desire Screener (DSDS) for Diagnosis of Hypoactive Sexual Desire Disorder (HSDD) in European Women, Joint Congress of the European and International Societies of Sexual Medicine (ESSM/ISSM), 2008, 8 pgs. (oral presentation).

Nappi et al., Decreased Sexual Desire Screener (DSDS) for Diagnosis of Hypoactive Sexual Desire Disorder (HSDD) in European Women, Joint Congress of the European and International Societies of Sexual Medicine (ESSM/ISSM), 2008, 1 pg. (abstract).

Nappi et al., Decreased Sexual Desire Screener (DSDS) for Diagnosis of Hypoactive Sexual Desire Disorder (HSDD) in European Women, International Society for the Study of Womens Sexual Health (ISSWSH) annual meeting, 2009, oral presentation, 8 pgs. (oral presentation).

Nappi et al., Decreased Sexual Desire Screener (DSDS) for Diagnosis of Hypoactive Sexual Desire Disorder (HSDD) in European Women, International Society for the Study of Womens Sexual Health (ISSWSH) annual meeting, 2009, oral presentation, 1 pg. (abstract).

Pyke et al., Using e-Diaries to Measure Sexual Desire in Women with Hypoactive Sexual Desire Disorder, American Psychiatric Association (APA) annual meeting, 2007, 2 pgs. (poster and abstract).

Pyke et al., The ROSE Study: Placebo-Controlled Randomized Withdrawal Trial of Flibanserin for Hypoactive Sexual Desire Disorder in Premenopausal Women (Study Design Only), Institute on Psychiatric Services (IPS) annual meeting, 2007, 2 pgs. (poster and abstract).
Pyke et al., Safety and Tolerability of Flibanserin in Premenopausal Women With Hypoactive Sexual Desire Disorder (HSDD): Results From the ROSE Study, American Psychiatric Association (APA) annual meeting, 2008, 2 pgs. (poster and abstract).
Pyke et al., Flibanserin: a Novel Centrally Acting Agent That is not an Effective Antidepressant but has Potential to Treat Decreased Sexual Desire in Women, American Psychiatric Association (APA) annual meeting, 2008, 2 pgs. (poster and abstract).
Rosen et al., The Predictors of Sexual Distress in Women With Low Sexual Desire, International Society for the Study of Womens Sexual Health (ISSWSH) annual meeting, 2009, oral presentation, 15 pgs. (oral presentation and abstract).
Shifren et al., Sexual Problems and Distress in United States Women: Prevalence and Correlates, Obstet. Gynecology, Nov. 2008, 112(5):970-978.
Shifren et al., Treatment-seeking Behavior of U.S. Women with Hypoactive Sexual Desire Disorder (HSDD), American College of Obstetrics and Gynecologists (ACOG) annual meeting, 2008, 2 pgs. (poster and abstract).
Pyke et al., Validation of the Sexual Interest and Desire Inventory-Female (SIDI-F) in European Women, International Society for the Study of Womens Sexual Health (ISSWSH) annual meeting, 2007, 20 pgs. (oral presentation).
Nappi et al., Validation of the Sexual Interest and Desire Inventory-Female (SIDI-F) in European Women, European Society for Sexual Medicine (ESSM) annual meeting, 2007, 19 pgs. (oral presentation).
Sand et al., The Female Sexual Function Index (FSFI): A Potential "Gold Standard" Measure for Assessing Therapeutically-Induced Change in Female Sexual Function, ASRM, 2009, Oct. 17-21, 2009, Atlanta, Georgia, 2 pgs. (poster and abstract).
Smith et al., Pharmacokinetics of Flibanserin in Premenopausal Women With Hypoactive Sexual Desire Disorder Including Effects on the Female Sexual Function Index, ESSM, 2009, Nov. 2009, 2 pgs., Lyon. (poster and abstract).
Clayton et al., Efficacy of Flibanserin as a Potential Treatment for Hypoactive Sexual Desire Disorder in North American Premenopausal Women: Results From the Dahlia Trial, ESSM, 2009, Nov. 2009, 2 pgs., Lyon. (poster and abstract).
Thorp et al., Efficacy of Flibanserin as a Potential Treatment for Hypoactive Sexual Desire Disorder in North American Premenopausal Women: Results From the Daisy Trial, ESSM, 2009, Nov. 2009, 3 pgs., Lyon. (poster and abstract).
Jolly et al., Design of Randomized Controlled Trials of Flibanserin in Premenopausal Women With Hypoactive Sexual Desire Disorder, ESSM 2009, Nov. 2009, 3 pgs., Lyon. (poster and abstract).
Revicki et al., Content Validity of the Female Sexual Function Index in Pre- and Postmenopausal Women With Hypoactive Sexual Desire Disorder, ESSM 2009, Nov. 2009, 2 pgs., Lyon. (poster and abstract).
Aubert et al., Comparison of Flibanserin With the 5-Htla Agonist (+)-8-Oh-Dpat in Affecting Interactions Between Male-Female Marmoset Pairs, ESSM 2009, Nov. 2009, 2 pgs., Lyon (poster and abstract).
Rosen et al., Criterion Validity of the Sexual Desire Domain of the Female Sexual Function Index (FSFI): Identifying a Diagnostic Cut-Point for Differentiating Women With and Without HSDD, ESSM 2009, Nov. 2009, 3 pgs., Lyon. (poster and abstract).
Rosen et al., Validation of the FSFI Sexual Desire Domain Diagnostic Cut-Point in Predicting Hsdd in Women: Independent Replication and Confirmation, ESSM 2009, Nov. 2009, 2 pgs., Lyon. (poster and abstract).
Nappi, Efficacy of Flibanserin as a Potential Treatment for Hypoactive Sexual Desire Disorder in European Premenopausal Women: Results From the Orchid Trial; ESSM 2009, Nov. 2009, 12 pgs., Lyon. (oral presentation).
Nappi et al., Efficacy of Flibanserin as a Potential Treatment for Hypoactive Sexual Desire Disorder in European Premenopausal Women: Results From the Orchid Trial; ESSM 2009, Nov. 2009, 1 pg., Lyon. (abstract).
Holstege et al., Differences in Brain Activity in Premenopausal Women With Hypoactive Sexual Desire Disorder (HSDD) Compared to Women Without Sexual Dysfunction, ESSM 2009, Nov. 2009, 2 pgs., Lyon. (abstract only).
Holstege et al., Brain activation and de-activation caused by erotic movies is lower in HSDD—than in non-HSDD volunteers, ESSM 2009, 8 pgs. (oral presentation).
Jolly, Efficacy of Flibanserin 100 Mg Qhs as a Potential Treatment for Hypoactive Sexual Desire Disorder in Premenopausal Women, ESSM 2009, Nov. 2009, 12 pgs., Lyon. (oral presentation).
Jolly et al., Efficacy of Flibanserin 100 Mg Qhs as a Potential Treatment for Hypoactive Sexual Desire Disorder in Premenopausal Women, ESSM 2009, Nov. 2009, 1 pgs., Lyon. (abstract).
Jolly et al., Efficacy of Flibanserin 100 Mg Qhs as a Potential Treatment for Hypoactive Sexual Desire Disorder in North American Premenopausal Women, ESSM 2009, Nov. 2009, 2 pgs., Lyon. (poster and abstract).
Clayton, Safety and Tolerability of Flibanserin in Premenopausal Women With Hypoactive Sexual Desire Disorder, ESSM 2009, Nov. 2009, 12 pgs., Lyon. (oral presentation).
Jolly et al., Safety and Tolerability of Flibanserin in Premenopausal Women With Hypoactive Sexual Desire Disorder, ESSM 2009, Nov. 2009, 1 pg., Lyon. (abstract).
Jolly et al., Efficacy of Flibanserin as a Potential Treatment for Hypoactive Sexual Desire Disorder in North American Premenopausal Women: Results From the Violet Trial, ESSM 2009, Nov. 2009, 3 pgs., Lyon. (poster and abstract).
Fuchs, Baseline Characteristics of Patients Enrolled in Three Phase III North American Trials of Flibanserin in Premenopausal Women With Hypoactive Sexual Desire Disorder, FIGO 2009, Oct. 2009, 10 pgs., Cape Town, South Africa. (oral presentation).
Goldfischer, Efficacy and Safety of Flibanserin in a Randomized Withdrawal Study of Premenopausal Women With Hypoactive Sexual Desire Disorder, FIGO2009, Oct. 2009, 12 pgs., Cape Town, South Africa. (oral presentation).
Goldfischer et al., Efficacy and Safety of Flibanserin in a Randomized Withdrawal Study of Premenopausal Women With Hypoactive Sexual Desire Disorder, FIGO2009, Oct. 2009, 1 pgs., Cape Town, South Africa. (abstract).
Revicki et al., Content Validity of the Female Sexual Function Index in Pre- and Postmenopausal Women With Hypoactive Sexual Desire Disorder, ICSM 2009, Jul. 2009, 2 pgs., Paris. (poster and abstract).
Revicki et al., Content Validity of the Female Sexual Function Index in Pre-Menopausal Women With Hypoactive Sexual Desire Disorder, ICSM 2009, Jul. 2009, 2 pgs., Paris. (poster and abstract).
Rosen et al., Criterion Validity of the Sexual Desire Domain of the Female Sexual Function Index (Fsfi): Identifying a Diagnostic Cut-Point for Differentiating Women With and Without HSDD, ICSM 2009, Jul. 2009, 2 pgs., Paris. (poster and abstract).
Rosen et al., Validation of the Fsfi Sexual Desire Domain Diagnostic Cut-Point in Predicting HSDD: Independent Replication and Confirmation, ICSM 2009, Jul. 2009, 2 pgs., Paris. (poster and abstract).
Sand et al., The Female Sexual Function Index (Fsfi): A Potential "Gold Standard" Measure for Assessing Sexual Function in Women, ICSM 2009, Jul. 2009, 2 pgs., Paris. (poster and abstract).
Jayne, Results From the Dahlia (511.70) Trial: A Prospective Study of Flibanserin for the Treatment of Hypoactive Sexual Desire Disorder in North American Premenopausal Women, SMSNA 2009, Nov. 2009, 3 pgs,, San Diego, USA (oral presentation).
Jayne et al., Results From the Dahlia (511.70) Trial: A Prospective Study of Flibanserin for the Treatment of Hypoactive Sexual Desire Disorder in North American Premenopausal Women, SMSNA 2009, Nov. 2009, 2 pgs., San Diego, USA (abstract and poster).
Sand et al., Efficacy of Flibanserin in North American Premenopausal Women With Hypoactive Sexual Desire Disorder: Results From the Daisy Trial, SMSNA 2009, Nov. 2009, 2 pgs., San Diego, USA. (poster and abstract).
Sand, Efficacy of Flibanserin in North American Premenopausal Women With Hypoactive Sexual Desire Disorder: Results From the Daisy Trial, SMSNA 2009, Nov. 2009, 2 pgs., San Diego, USA. (oral presentation).
Sand et al., The Female Sexual Function Index (Fsfi) is a Potential "Gold Standard" Measure for Assessing Sexual Function in Pre- and Post-Menopausal Women: A Systematic Review, SMSNA 2009, Nov. 2009, 2 pgs., San Diego, USA. (poster and abstract).

Sand et al., Efficacy of Flibanserin 100 Mg Qhs as a Potential Treatment for Hypoactive Sexual Desire Disorder in North American Premenopausal Women, SMSNA 2009, Nov. 2009, 2 pgs., San Diego, USA. (poster and abstract).

Sand, Efficacy of Flibanserin 100 Mg Qhs as a Potential Treatment for Hypoactive Sexual Desire Disorder in North American Premenopausal Women, SMSNA 2009, Nov. 2009, 2 pgs., San Diego, USA. (oral presentation).

Holstege et al., Differences in Brain Activity in Premenopausal Women With Hypoactive Sexual Desire Disorder (HSDD) Compared to Women Without Sexual Dysfunction, SMSNA 2009, Nov. 2009, 2 pgs., San Diego, USA (abstract only).

Holstege et al., Brain activation and de-activation caused by erotic movies is lower in HSDD—than in non-HSDD volunteers, SMSNA, 2009, 4 pgs (poster & oral presentation).

Sand et al., Pooled Clinical Trail Analysis of Flibanserin Safety and Tolerability in Premenopausal Women with Hypoactive Sexual Desire Disorder, SMSNA, 2009, 2 pgs. (poster and abstract).

Sand, Pooled Clinical Trail Analysis of Flibanserin Safety and Tolerability in Premenopausal Women with Hypoactive Sexual Desire Disorder, SMSNA, 2009, 2 pgs. (oral presentation).

Sand et al., Effacacy of Flibanserin in North American Premenopausal Women with Hypoactive Sexual Desire Disorder: Results from the Violet Trial, SMSNA, 2009, 3 pgs. (poster and abstract).

Sand, Effacacy of Flibanserin in North American Premenopausal Women with Hypoactive Sexual Desire Disorder: Results from the Violet Trial, SMSNA, 2009, 2 pgs. (oral presentation).

Meston, The Female Sexual Function Index (FSFI) is a Potential "Gold Standard" Measure for Assessing Sexual Function in Pre- and post-menopausal Women: a Systematic Review, SMSNA, 2009, 3 pgs. (oral presentation).

Goldfischer, Efficacy and Safety of Flibanserin in a Randomized Withdrawal Study of Premenopausal Women With Hypoactive Sexual Desire Disorder, WAS, 2009, 12 pgs. (oral presentation).

Goldfischer et al., Efficacy and Safety of Flibanserin in a Randomized Withdrawal Study of Premenopausal Women With Hypoactive Sexual Desire Disorder, WAS, 2009, 1 pgs. (abst.).

Clayton et al., Baseline Characteristics of Patients Enrolled in Three Phase III North American Trials of Flibanserin in Premenopausaul Women with Hypoactive Sexual Desire Disorder, WAS, 2009, 2 pgs. (poster and abstract).

Clayton, Baseline Characteristics of Patients Enrolled in Three Phase III North American Trials of Flibanserin in Premenopausaul Women with Hypoactive Sexual Desire Disorder, WAS, 2009, 4 pgs. (oral presentation).

Derogatis et al., Content Validity of the Female Sexual Distress Scale-Revised in Women With Hypoactive Sexual Desire Disorder, WAS, 2009, 1 pg. (abstract only).

Dennerstein et al., Attitudes Toward and Frequency of Partner Interactions Among Women Reporting Decreased Sexual Desire, J. Sex Med., 2009, 6:1668-1673.

Goldstein et al., National Differences in Patient-Clinician Communication Regarding Hypoactive Sexual Desire Disorder, J. Sex Med., 2009, 6:1349-1357.

Johannes et al., Distressing Sexual Problems in United States Women Revisited: Prevalence After Accounting for Depression, J. Clin. Psych., 2009, 70(12):1698-1706.

Pfaus, Pathways of Sexual Desire, J. Sex Med., 2009, 6:1506-1533.

Rosen et al., Correlates of Sexually Related Personal Distress in Women with Low Sexual Desire, J. Sex Med., 2009, 6:1549-1560.

Lewis-D' Agostino et al., Validating the Sexual Interest and Desire Inventory (SIDI-F) in North American Women, American College of Obstetrics and Gynecologists (ACOG) annual meeting, 2007, 1 pg. (poster).

Shifren et al., Help-Seeking Behavior of Women with Self-Reported Distressing Sexual Problems, J. of Women's Health, 2009, 18(4):461-468.

Wunderlich et al., Validity of Sexual Distress Scales vs Electronic Diary in Women with Decreased Sexual Desire, American College of Obstetrics and Gynecologists (ACOG) annual meeting, 2007, 1 pg. (poster).

Clayton et al., Using e-Diaries to Measure Sexual Desire in Women with Hypoactive Sexual Desire Disorder, European Society for Sexual Medicine (ESSM) annual meeting, 2007, 2 pgs. (abstract).

Van Lunsen et al., Validation of the Sexual Interest and Desire Inventory-Female (SIDI-F) in European Women, European Society for Sexual Medicine (ESSM) annual meeting, 2007, 1 pg. (abstract).

Clayton et al., Using e-Diaries to Measure Sexual Desire in Women with Hypoactive Sexual Desire Disorder, International Society for the Study of Womens Sexual Health (ISSWSH) annual meeting, 2007, 2 pgs. (abstract).

Van Lundsen, Validation of the Sexual Interest and Desire Inventory-Female (SIDI-F) in European women, ISSWSH, 2007, 2 pgs. (abstract).

Goldfischer et al., The ROSE Study: Placebo-controlled Randomized Withdrawal Trial of Flibanserin for Hypoactive Sexual Desire Disorder in Premenopausal Women, Sexual Medicine Society of North America (SMSNA) annual meeting, 2007, 1 pg. (abstract).

Krychman et al., The ROSE Study: Placebo-controlled Randomized Withdrawal Trial of Flibanserin for Hypoactive Sexual Desire Disorder in Premenopausal Women, European Board and College of Obstetrics and Gynaecology (EBCOG) annual meeting, 2008, 6 pgs. (poster and oral presentation).

Clayton et al., Baseline Characteristics of Patients Enrolled in Three Phase III North American Trials of Flibanserin in Premenopausal Women With Hypoactive Sexual Desire Disorder, FIGO 2009, Oct. 2009, 1 pg., Cape Town, South Africa. (abstract).

Scandroglio et al., Ex Vivo binding of Flibanserin to Serotonin-5-HT1A and 5-HT2A Receptors, Pharm. Res., 2001, 43(2):179-183.

D'Aquila et al., Anti-anhedonic actions of the novel serotonergic agent flibanserin, a potential rapidly-acting antidepressant, Euro. J. Pharm., 1997, 340:121-132.

Flik et al., Assessment of serotonin and catecholamine levels in the female rat brain following acute and chronic administration with flibanserin, a potential novel treatment for hypoactive sexual desire disorder: An in vivo microdialysis study, presented at Neuroscience 2009, Feb. 3, 2010, http://www.abstractsonline.com/Plan/AbstractPrintView.aspx9mID=2285&sKey=65206 . . . , 2 pgs.

Banfi et al., Benzimidazolone Derivatives: a new class of putative antidepressant agents, 13th Int. Symp. On Medicinal Chemistry, Sep. 19-23, 1994, pg. 102. (abstract).

Borsini et la., BIMT 17, a 5-Ht1A receptor agonist/5-HT2A receptor antagonist, directly activates portsynaptic 5-HT inhibitory responses in the rat cerebral cortex, Naunyn-Schmiedeberg's Arch Pharm., 1995, 352:283-290.

Boehringer Ingelheim, Flibanserin BIMT-17, Drugs of the Future, 1999, 24(1):91.

Podhorna et al., Flibanserin has anxiolytic effects without locomotor side effects in the infant rat ultrasonic vocalization model of anxiety, Workshop on Depression Anxiety Spectrum Disorders: from Neurobiology to Novel Pharm. Treatmts, Int. Acad. for Biomed. and Drug Res., Abstract-Book, Milan, Sep. 6-7, 2000, 1 pg.

Vaccarino et al., Flibanserin, a 5-HT1A agonist/5-HT2A antagonist, decreases sucrose intake in operant and non-operant paradigms in rats, Soc. Neurosci. Abstr., 2000, 26:394:Abstr 144.9, 30th Ann Mtg. of Soc. for Neurosci, New Orleans, Nov. 4-9, 1000, 1 pg.

Borsini et al., Further characterisation of potential antidepressant action of flibanserin, Psychopharm., 2001, 159:64-69.

Rueter et al., In Vivo Electrophysiological Assessment of the Agonistic Properties of Flibanserin at Pre- and Postsynaptic 5-HT1A Receptors in the Rat Brain, Synapse, 1998, 29:392-405.

Cervo et al., Involvement of 5-HT1A receptors in flibanserin discriminative stimulus in female rats, Neurosci 2009, Feb. 3, 2010, http://www.abstractsonline com/Plan/AbstratPrintView.aspx?mID=2285&sKey=65206 . . . , 2pgs.

Cervo et al., Involvement of 5-HT1A receptors in flibanserin discriminative stimulus in female rats, Dept. CNS Diseases, Prog. No. 465.20, 2009 Neurosci., Oct. 19, 2009, 1 pg. (poster).

Ferger et al., Neurochemical characterization of Flibanserin a phase III drug for treatment of hypoactive sexual desire disorder (HSDD) in women, Neurosci 2009, Feb. 3, 2010, http://www.abstractsonline.com/Plan/AbstractPrintView.aspx?mIK=2285&sKey=65206 . . . , 2pgs.

Flik et al., Assessment of serotonin and catecholamine levels in the female rat brain following acute and chronic administration with flibanserin, a potential novel treatment for hypoactive sexual desire disorder: An in vivo microdialysis study, SFN, 2009, 1 pg. (poster).

Ferger et al., Neurochemical characterization of Flibanserin a phase III drug for treatment of hypoactive sexual desire disorder (HSDD) in women, SFN, 2009, 1 pg. (poster).

Evans et al., The Effects of Flibanserin on Amphetamine Withdrawal-Induced hypolocomotion in Rats, Soc. Neurosci Abstr., Nov. 7-12, 1998, 24:2133:Abstr 848.5, 28th Ann. Mtg. of the Soc. for Neurosci, Los Angeles, 1 pg.

Advisory Action dated Dec. 27, 2005, U.S. Appl. No. 10/272,603, filed Oct. 16, 2002 now US Pat. No. 7151103, issued Dec. 19, 2006, 3 pgs.

Examiner's Interview dated Jun. 23, 2006, U.S. Appl. No. 10/272,603, filed Oct. 16, 2002 now US Pat. No. 7151103, issued Dec. 19, 2006, 2 pgs.

Examiner's Interview dated Oct. 20, 2005, U.S. Appl. No. 10/272,603, filed Oct. 16, 2002 now US Pat. No. 7151103, issued Dec. 19, 2006, 1 pg.

Final Office Action dated Jun. 2, 2005, U.S. Appl. No. 10/272,603, filed Oct. 16, 2002 now US Pat. No. 7151103, issued Dec. 19, 2006, 9 pgs.

Notice of Allowance dated Jun. 23, 2006, U.S. Appl. No. 10/272,603, filed Oct. 16, 2002 now US Pat. No. 7151103, issued Dec. 19, 2006, 7 pgs.

Notice of Appeal/Amendment dated Nov. 8, 2005, U.S. Appl. No. 10/272,603, filed Oct. 16, 2002 now US Pat. No. 7151103, issued Dec. 19, 2006, 9 pgs.

Office Action dated Oct. 14, 2004, U.S. Appl. No. 10/272,603, filed Oct. 16, 2002 now US Pat. No. 7151103, issued Dec. 19, 2006, 8 pgs.

RCE/Supp. Amendment dated Jun. 8, 2006, U.S. Appl. No. 10/272,603, filed Oct. 16, 2002 now US Pat. No. 7151103, issued Dec. 19, 2006, 29 pgs.

Reply dated Feb. 14, 2005, U.S. Appl. No. 10/272,603, filed Oct. 16, 2002 now US Pat. No. 7151103, issued Dec. 19, 2006, 20 pgs.

Examiner's Search Strategy dated Jun. 20, 2006, U.S. Appl. No. 10/272,603, filed Oct. 16, 2002 now US Pat. No. 7151103, issued Dec. 19, 2006, 2 pgs.

Examiner's Search Strategy dated Jun. 21, 2006, U.S. Appl. No. 10/272,603, filed Oct. 16, 2002 now US Pat. No. 7151103, issued Dec. 19, 2006, 20 pgs.

Examiner's Search Strategy dated Sep. 22, 2004, U.S. Appl. No. 10/272,603, filed Oct. 16, 2002 now US Pat. No. 7151103, issued Dec. 19, 2006, 83 pgs.

Examiner's Search Strategy dated Sep. 28, 2004, U.S. Appl. No. 10/272,603, filed Oct. 16, 2002 now US Pat. No. 7151103, issued Dec. 19, 2006, 117 pgs.

Examiner's Search Strategy dated Sep. 29, 2004, U.S. Appl. No. 10/272,603, filed Oct. 16, 2002 now US Pat. No. 7151103, issued Dec. 19, 2006, 1 pg.

Examiner's Search Strategy dated Oct. 14, 2004, U.S. Appl. No. 10/272,603, filed Oct. 16, 2002 now US Pat. No. 7151103, issued Dec. 19, 2006, 3pgs.

Final Office Action dated Oct. 5, 2005, U.S. Appl. No. 10/210,474, filed Aug. 1, 2002 now US Pat. No. 7183410, issued Feb. 27, 2007, 6 pgs.

Notice of Allowance dated Jan. 30, 2006, U.S. Appl. No. 10/210,474, filed Aug. 1, 2002 now US Pat. No. 7183410, issued Feb. 27, 2007, 7 pgs.

Notice of Allowance dated Jul. 12, 2006, U.S. Appl. No. 10/210,474, filed Aug. 1, 2002 now US Pat. No. 7183410, issued Feb. 27, 2007, 7 pgs.

Office Action dated Mar. 16, 2005, U.S. Appl. No. 10/210,474, filed Aug. 1, 2002 now US Pat. No. 7183410, issued Feb. 27, 2007, 9 pgs.

Office Action dated Jul. 26, 2004, U.S. Appl. No. 10/210,474, filed Aug. 1, 2002 now US Pat. No. 7183410, issued Feb. 27, 2007, 7 pgs.

Response to Final Office Action dated Dec. 15, 2005, U.S. Appl. No. 10/210,474, filed Aug. 1, 2002 now US Pat. No. 7183410, issued Feb. 27, 2007, 9 pgs.

Reply dated Jan. 26, 2005, U.S. Appl. No. 10/210,474, filed Aug. 1, 2002 now US Pat. No. 7183410, issued Feb. 27, 2007, 24 pgs.

Amendment dated Jul. 11, 2005, U.S. Appl. No. 10/210,474, filed Aug. 1, 2002 now US Pat. No. 7183410, issued Feb. 27, 2007, 13 pgs.

Examiner's Search Strategy dated Mar. 10, 2005, U.S. Appl. No. 10/210,474, filed Aug. 1, 2002 now US Pat. No. 7183410, issued Feb. 27, 2007, 36 pgs.

Examiner's Search Strategy dated Sep. 30, 2005, U.S. Appl. No. 10/210,474, filed Aug. 1, 2002 now US Pat. No. 7183410, issued Feb. 27, 2007, 6 pgs.

Reply with Amendment dated Mar. 8, 2005, U.S. Appl. No. 10/210,474, filed Aug. 1, 2002 now US Pat. No. 7183410, issued Feb. 27, 2007, 10 pgs.

Supplemental Amendment dated Jan. 19, 2006, U.S. Appl. No. 10/210,474, filed Aug. 1, 2002 now US Pat. No. 7183410, issued Feb. 27, 2007, 6 pgs.

Examiner's Interview dated Nov. 19, 2007, U.S. Appl. No. 11/546,303, filed Oct. 12, 2006, 3 pgs.

Final Office Action dated Sep. 14, 2007, U.S. Appl. No. 11/546,303, filed Oct. 12, 2006, 4 pgs.

Office Action dated Jan. 5, 2007, U.S. Appl. No. 11/546,303, filed Oct. 12, 2006, 7 pgs.

Response dated Jul. 5, 2007, U.S. Appl. No. 11/546,303, filed Oct. 12, 2006, 6 pgs.

Examiner's Search Strategy dated Mar. 10, 2005, U.S. Appl. No. 11/546,303, filed Oct. 12, 2006, 36 pgs.

Examiner's Interview Summ. Dated Jan. 17, 2008, U.S. Appl. No. 11/546,304, filed Oct. 12, 2006 now US Pat No. 7420057 issued Sep. 2, 2008, 3 pgs.

Notice of Allowance dated Apr. 30, 2008, U.S. Appl. No. 11/546,304, filed Oct. 12, 2006 now US Pat No. 7420057 issued Sep. 2, 2008, 8 pgs.

Office Action dated Jan. 3, 2007, U.S. Appl. No. 11/546,304, filed Oct. 12, 2006 now US Pat No. 7420057 issued Sep. 2, 2008, 7 pgs.

Office Action dated Jul. 18, 2007, U.S. Appl. No. 11/546,304, filed Oct. 12, 2006 now US Pat No. 7420057 issued Sep. 2, 2008, 4 pgs.

Response dated Jan. 17, 2008, U.S. Appl. No. 11/546,304, filed Oct. 12, 2006 now US Pat No. 7420057 issued Sep. 2, 2008, 24 pgs.

Response dated Apr. 3, 2007, U.S. Appl. No. 11/546,304, filed Oct. 12, 2006 now US Pat No. 7420057 issued Sep. 2, 2008, 7 pgs.

Supp. Response dated Mar. 19, 2008, U.S. Appl. No. 11/546,304, filed Oct. 12, 2006 now US Pat No. 7420057 issued Sep. 2, 2008, 13 pgs.

Supp. Response dated Mar. 24, 2008, U.S. Appl. No. 11/546,304, filed Oct. 12, 2006 now US Pat No. 7420057 issued Sep. 2, 2008, 14 pgs.

2nd Supp. Response dated Apr. 23, 2008, U.S. Appl. No. 11/546,304, filed Oct. 12, 2006 now US Pat No. 7420057 issued Sep. 2, 2008, 14 pgs.

Final Office Action dated Apr. 23, 2007, U.S. Appl. No. 11/079,070, filed Mar. 14, 2005, 11 pgs.

Notice of Allowance dated Sep. 14, 2007, U.S. Appl. No. 11/079,070, filed Mar. 14, 2005, 6 pgs.

Office Action dated Jan. 11, 2008, U.S. Appl. No. 11/079,070, filed Mar. 14, 2005, 8 pgs.

Office Action dated Sep. 13, 2006, U.S. Appl. No. 11/079,070, filed Mar. 14, 2005, 5 pgs.

Response to Final Office Action dated Jul. 23, 2007, U.S. Appl. No. 11/079,070, filed Mar. 14, 2005, 7 pgs.

RCE dated Nov. 2, 2007, U.S. Appl. No. 11/079,070, filed Mar. 14, 2005, 4 pgs.

Response dated Jan. 16, 2007, U.S. Appl. No. 11/079,070, filed Mar. 14, 2005, 8 pgs.

Examiner Search Strategy dated Jan. 3, 2008, U.S. Appl. No. 11/079,070, filed Mar. 14, 2005, 20 pgs.

Examiner's Search Strategy dated Jul. 21, 2006, U.S. Appl. No. 11/079,070, filed Mar. 14, 2005, 106 pgs.

Advisory Action dated Jul. 2, 2009, U.S. Appl. No. 11/278,551, filed Apr. 4, 2006, 3 pgs.

Final Office Action dated Apr. 13, 2009, U.S. Appl. No. 11/278,551, filed Apr. 4, 2006, 9 pgs.

Office Action dated Jun. 1, 2007, U.S. Appl. No. 11/278,551, filed Apr. 4, 2006, 9 pgs.

Office Action dated Jul. 6, 2006, U.S. Appl. No. 11/278,551, filed Apr. 4, 2006, 8 pgs.
Office Action dated Jul. 9, 2008, U.S. Appl. No. 11/278,551, filed Apr. 4, 2006, 12 pgs.
Office Action dated Dec. 28, 2009, U.S. Appl. No. 11/278,551, filed Apr. 4, 2006, 9 pgs.
Responsive Amendment to Final Office Action, dated Jun. 12, 2009, U.S. Appl. No. 11/278,551, filed Apr. 4, 2006, 63 pgs.
RCE and Responsive Amendment to Final Office Action, dated Oct. 7, 2009, U.S. Appl. No. 11/278,551, filed Apr. 4, 2006, 14 pgs.
Response dated Jan. 9, 2009, U.S. Appl. No. 11/278,551, filed Apr. 4, 2006, 64 pgs.
Response dated Nov. 30, 2007, U.S. Appl. No. 11/278,551, filed Apr. 4, 2006, 25 pgs.
Response dated Dec. 19, 2006, U.S. Appl. No. 11/278,551, filed Apr. 4, 2006, 4 pgs.
Examiner's Search Strategy dated Apr. 13, 2009, U.S. Appl. No. 11/278,551, filed Apr. 4, 2006, 2 pgs.
Examiner's Search Strategy dated Jun. 1, 2007, U.S. Appl. No. 11/278,551, filed Apr. 4, 2006, 10 pgs.
Examiner's Search Strategy dated Jun. 26, 2006, U.S. Appl. No. 11/278,551, filed Apr. 4, 2006, 19 pgs.
Examiner's Search Strategy dated Jul. 9, 2008, U.S. Appl. No. 11/278,551, filed Apr. 4, 2006, 6 pgs.
Examiner's Search Strategy dated Dec. 28, 2009, U.S. Appl. No. 11/278,551, filed Apr. 4, 2006, 3 pgs.
Final Office Action dated Sep. 12, 2008, U.S. Appl. No. 11/381,590, filed Apr. 4, 2006, 10 pgs.
Office Action dated Apr. 3, 2007, U.S. Appl. No. 11/381,590, filed Apr. 4, 2006, 8 pgs.
Office Action dated Dec. 27, 2007, U.S. Appl. No. 11/381,590, filed Apr. 4, 2006, 8 pgs.
Response dated Jun. 26, 2008, U.S. Appl. No. 11/381,590, filed Apr. 4, 2006, 7 pgs.
Amendment and Reply dated Oct. 3, 2007, U.S. Appl. No. 11/381,590, filed Apr. 4, 2006, 8 pgs.
Examiner's Search Strategy dated Mar. 30, 2007, U.S. Appl. No. 11/381,590, filed Apr. 4, 2006, 48 pgs.
Office Action dated Mar. 23, 2009, U.S. Appl. No. 11/383,796, filed May 17, 2006; 11 pgs.
Examiner's Search Strategy dated Mar. 23, 2009, U.S. Appl. No. 11/383,796, filed May 17, 2006; 2 pgs.
Office Action dated Mar. 19, 2009, U.S. Appl. No. 11/383,793, filed May 17, 2006, 12 pgs.
Examiner's Search Strategy dated Mar. 19, 2009, U.S. Appl. No. 11/383,793, filed May 17, 2006, 3 pgs.
Advisory Action dated Feb. 10, 2009, U.S. Appl. No. 11/381,130, filed May 2, 2006, 3 pgs.
Final Office Action dated Jul. 18, 2008, U.S. Appl. No. 11/381,130, filed May 2, 2006, 17pgs.
Office Action dated Oct. 9, 2007, U.S. Appl. No. 11/381,130, filed May 2, 2006, 13 pgs.
Response to Final Office Action dated Jan. 21, 2009, U.S. Appl. No. 11/381,130, filed May 2, 2006, 13 pgs.
Response dated Apr. 9, 2008, U.S. Appl. No. 11/381,130, filed May 2, 2006, 36 pgs.
Office Action dated Jun. 1, 2009, U.S. Appl. No. 11/364,306, filed Feb. 28, 2006, 18 pgs.
Examiner's Search Strategy dated Jun. 1, 2009, U.S. Appl. No. 11/364,306, 3 pgs.
Final Office Action dated Sep. 4, 2008, U.S. Appl. No. 11/364,153, filed Feb. 28, 2006, 12 pgs.
Office Action dated Nov. 29, 2007, U.S. Appl. No. 11/364,153, filed Feb. 28, 2006, 11 pgs.
Response dated May 29, 2008, U.S. Appl. No. 11/364,153, filed Feb. 28, 2006, 62 pgs.
Office Action dated Apr. 29, 2009, U.S. Appl. No. 11/364,785, filed Feb. 28, 2006, 23 pgs.
Examiner's Search Strategy dated Apr. 29, 2009, U.S. Appl. No. 11/364,785, filed Feb. 28, 2006, 19 pgs.
Office Action dated Jan. 14, 2010, U.S. Appl. No. 12/091,848, filed Apr. 28, 2008, 5 pgs.
Examiner's Search Strategy dated Jan. 14, 2010, U.S. Appl. No. 12/091,848, filed Apr. 28, 2008, 47 pgs.
Office Action dated Apr. 9, 2009, U.S. Appl. No. 12/170,884, filed Jul. 10, 2008, 10 pgs.
Response dated Oct. 9, 2009, U.S. Appl. No. 12/170,884, filed Jul. 10, 2008, 3 pgs.
Examiner's Search Strategy dated Feb. 19, 2010, U.S. Appl. No. 12/170,884, filed Jul. 10, 2008, 26 pgs.
Examiner's Interview Summary dated Feb. 19, 2010, U.S. Appl. No. 12/170,884, filed Jul. 10, 2008, 4 pgs.
Notice of Allowance dated Feb. 19, 2010, U.S. Appl. No. 12/170,884, filed Jul. 10, 2008, 5 pgs.
Office Action dated Mar. 5, 2009, U.S. Appl. No. 11/740,959, filed Apr. 27, 2007, 30 pgs.
Response dated Sep. 3, 2009, U.S. Appl. No. 11/740,959, filed Apr. 27, 2007, 12 pgs.
Examiner's Search Strategy dated Mar. 5, 2009, U.S. Appl. No. 11/740,959, filed Apr. 27, 2007, 12 pgs.
Final Office Action dated Jan. 20, 2010; U.S. Appl. No. 11/740,959, filed Apr. 27, 2007, 33 pgs.
Examiner's Search Strategy dated Jan. 20, 2010, U.S. Appl. No. 11/740,959, filed Apr. 27, 2007, 6 pgs.
Office Action dated Apr. 13, 2009, U.S. Appl. No. 11/097,939, filed Apr. 4, 2005, 12 pgs.
Amendment and Response dated Sep. 14, 2009, U.S. Appl. No. 11/097,939, filed Apr. 4, 2005, 8 pgs.
Examiner's Search Strategy dated Apr. 13, 2009, U.S. Appl. No. 11/097,939, filed Apr. 4, 2005, 3 pgs.
Final Office Action dated Feb. 17, 2010, U.S. Appl. No. 11/097,939, filed Apr. 4, 2005, 16 pgs.
Examiner's Search Strategy dated Feb. 17, 2010, U.S. Appl. No. 11/097,939, filed Apr. 4, 2005, 2 pgs.
Office Action dated Mar. 19, 2009, U.S. Appl. No. 11/554,855, filed Oct. 31, 2006, 11 pgs.
Response dated Aug. 19, 2009, U.S. Appl. No. 11/554,855, filed Oct. 31, 2006, 7 pgs.
Examiner's Search Strategy dated Mar. 19, 2009, U.S. Appl. No. 11/554,855, filed Oct. 31, 2006, 3 pgs.
Office Action dated Dec. 4, 2009, U.S. Appl. No. 11/554,855, filed Oct. 31, 2006, 15 pgs.
Examiner's Search Strategy dated Dec. 4, 2009, U.S. Appl. No. 11/554,855, filed Oct. 31, 2006, 3 pgs.
Office Action dated Mar. 19, 2009, U.S. Appl. No. 11/745,515, filed May 8, 2007, 11 pgs.
Office Action dated Dec. 4, 2009, U.S. Appl. No. 11/745,515, filed May 8, 2007, 16 pgs.
Examiner's Search Strategy dated Mar. 19, 2009, U.S. Appl. No. 11/745,515, filed May 8, 2007, 3 pgs.
Response dated Aug. 19, 2009, U.S. Appl. No. 11/745,515, filed May 8, 2007, 8 pgs.
Examiner's Search Strategy dated Dec. 4, 2009, U.S. Appl. No. 11/745,515, filed May 8, 2007, 3 pgs.
Office Action dated Oct. 11, 2005, U.S. Appl. No. 10/882,613, filed Jul. 1, 2004, 7 pgs.
Examiner's Search Strategy dated Oct. 2, 2005, U.S. Appl. No. 10/882,613, filed Jul. 1, 2004, 17 pgs.
Advisory Action dated Mar. 16, 2007, U.S. Appl. No. 10/444,892, filed May 22, 2003, 2 pgs.
Advisory Action dated Mar. 29, 2007, U.S. Appl. No. 10/444,892, filed May 22, 2003, 3 pgs.
Examiner's Interview Summ. Dated Oct. 4, 2007, U.S. Appl. No. 10/444,892, filed May 22, 2003, 2 pgs.
Final Office Action dated Aug. 29, 2006, U.S. Appl. No. 10/444,892, filed May 22, 2003, 7 pgs.
Office Action dated Mar. 1, 2006, U.S. Appl. No. 10/444,892, filed May 22, 2003, 5 pgs.
Amendment After Final dated Feb. 28, 2007, U.S. Appl. No. 10/444,892, filed May 22, 2003, 8 pgs.
Amendment dated Jun. 27, 2006, U.S. Appl. No. 10/444,892, filed May 22, 2003, 5 pgs.
Office Action dated Jul. 2, 2007, U.S. Appl. No. 11/110,449, filed Apr. 20, 2005, 11 pgs.

Examiner's Search Strategy dated Jun. 20, 2007, U.S. Appl. No. 11/110,449, filed Apr. 20, 2005, 7 pgs.
Office Action dated Jun. 29, 2009, U.S. Appl. No. 11/960,957, filed Oct. 20, 2007, 12 pgs.
Response dated Dec. 29, 2009, U.S. Appl. No. 11/960,957, filed Oct. 20, 2007, 10 pgs.
Examiner's Search Strategy dated Jun. 29, 2009, U.S. Appl. No. 11/960,957, filed Oct. 20, 2007, 1 pgs.
Notice of Non-Compliant Amendment dated Mar. 10, 2010, U.S. Appl. No. 11/960,957, filed Oct. 20, 2007, 2 pgs.
Amendment and Response to Notice of Non-Compliant Amendment dated Apr. 9, 2010, U.S. Appl. No. 11/960,957, filed Oct. 20, 2007, 5 pgs.
Office Action dated Jan. 26, 2007, U.S. Appl. No. 11/178,716, filed Jul. 11, 2005, 8 pgs.
Office Action dated Apr. 14, 2006, U.S. Appl. No. 11/178,716, filed Jul. 11, 2005, 8 pgs.
Amendment dated Jul. 25, 2006, U.S. Appl. No. 11/178,716, filed Jul. 11, 2005, 5 pgs.
Examiner's Search Strategy dated Jan. 21, 2007, U.S. Appl. No. 11/178,716, filed Jul. 11, 2005, 1 pg.
Examiner's Search Strategy dated Mar. 30, 2006, U.S. Appl. No. 11/178,716, filed Jul. 11, 2005, 15 pgs.
Examiner's Search Strategy dated Apr. 11, 2006, U.S. Appl. No. 11/178,716, filed Jul. 11, 2005, 1 pg.
Final Office Action dated May 18, 2007, U.S. Appl. No. 11/218,107, filed Sep. 1, 2005, 11 pgs.
Office Action dated Aug. 15, 2006, U.S. Appl. No. 11/218,107, filed Sep. 1, 2005, 8 pgs.
Response dated Feb. 14, 2007, U.S. Appl. No. 11/218,107, filed Sep. 1, 2005, 4 pgs.
Examiner's Search Strategy dated Jun. 30, 2006, U.S. Appl. No. 11/218,107, filed Sep. 1, 2005, 8 pgs.
Examiner's Search Strategy dated Aug. 11, 2006, U.S. Appl. No. 11/218,107, filed Sep. 1, 2005, 2 pgs.
Office Action dated Aug. 26, 2008, U.S. Appl. No. 11/940,655, filed Nov. 15, 2007, 7 pgs.
Office Action dated Sep. 28, 2009, U.S. Appl. No. 11/997,567, filed Mar. 21, 2008, 7 pgs.
Examiner's Search Strategy dated Sep. 28, 2009, U.S. Appl. No. 11/997,567, filed Mar. 21, 2008, 43 pgs.
Response dated Feb. 19, 2010, U.S. Appl. No. 11/997,567, filed Mar. 21, 2008, 10 pgs.
Office Action dated Jan. 25, 2010, U.S. Appl. No. 11/837,957, filed Aug. 13, 2007, 11 pgs.
Examiner's Search Strategy dated Jan. 25, 2010, U.S. Appl. No. 11/837,957, 6 pgs.
Examiner's Interview Summ. dated Oct. 2, 2009, U.S. Appl. No. 11/837,959, filed Aug. 13, 2007, 2 pgs.
Office Action dated Jul. 20, 2009, U.S. Appl. No. 11/837,959, filed Aug. 13, 2007, 8 pgs.
Examiner's Search Strategy dated Jul. 20, 2009, U.S. Appl. No. 11/837,959, filed Aug. 13, 2007, 5 pgs.
Final Office Action dated Mar. 25, 2010, U.S. Appl. No. 11/837,959, filed Aug. 13, 2007, 12 pgs.
Response dated Jan. 20, 2010, U.S. Appl. No. 11/837,959, filed Aug. 13, 2007, 11 pgs.
Ferger et al., Flibanserin, a drug intended for treatment of hypoactive sexual desire disorder in pre-menopausal women, affects spontaneous motor activity and brain neurochemistry in female rates, Naunyn Schmiedebergs Arch Pharmacol., Apr. 27, 2010, pp. 1-17 (epub ahead of print).
Aubert et al., Comparison of Flibanserin With the 5-Htla Agonist (+)-8-Oh-Dpat in Affecting Interactions Between Male-Female Marmoset Pairs, J. Sex Med., May 2010, 7(s3): 118. (abstract).
Aubert et al., Initial PET Assessment of Flibanserin-induced Neural Changes in Female Marmoset Monkeys, J. Sex Med., May 2010, 7(s3):131. (abstract).
Aubert et al., Chronic Treatment of Female Marmoset Monkeys with (+)-8-Oh-Dpat or Flibanserin Differentially Alters Response of the Hypothalamic-Pituitary-Adrenal Axis to Restraint and Acute Serotonergic Challenge, J. Sex Med., May 2010, 7(s3):131. (abstract).
Gelez et al., Chronic Flibanserin Treatment Increases Solicitations in the Female Rat, J. Sex Med., May 2010, 7(s3):118. (abstract).
Allers et al., Acute and Repeated Flibanserin Administration in Female Rats Modulates Monoamines Differentially Across Brain Areas: A Microdialysis Study, J. Sex Med., Feb. 2010, 33 pgs. (Epub ahead of print).
Goldfischer et al., Efficacy of Continued Flibanserin Treatment on Sexual Desire, Satisfying Sexual Events and Sexual Functioning in Premenopausal Women With HSDD: Results From the Researching Outcomes on Sustained Efficacy (ROSE) Study, International Society for the Study of Womens Sexual Health (ISSWSH) annual meeting, 2008, 17 pgs. (oral presentation).
Final Office Action dated May 21, 2010, U.S. Appl. No. 11/997,567, filed Mar. 21, 2008, 7 pgs.
Final Office Action dated May 27, 2010, U.S. Appl. No. 11/278,551, filed Apr. 4, 2006, 8 pgs.
Examiner's Search Strategy dated May 27, 2010, U.S. Appl. No. 11/278,551, filed Apr. 4, 2006, 3 pgs.
Response dated Jun. 4, 2010, U.S. Appl. No. 11/554,855, filed Oct. 31, 2006, 10 pgs.
Response dated Jun. 4, 2010, U.S. Appl. No. 11/745,515, filed May 8, 2007, 8 pgs.
Response dated Jun. 24, 2010 U.S. Appl. No. 12/091,848, filed Apr. 28, 2008, 5 pgs.
Restriction Requirement dated May 24, 2004 U.S. Appl. No. 10/210,474, filed Aug. 1, 2002 now US Pat. No. 7183410, issued Feb. 27, 2007, 6 pgs.
Response to Restriction Requirement dated Jun. 9, 2004 U.S. Appl. No. 10/210,474, filed Aug. 1, 2002 now US Pat. No. 7183410, issued Feb. 27, 2007, 2 pgs.
Restriction Requirement dated Aug. 20, 2008, U.S. Appl. No. 11/097,939, filed Apr. 4, 2005, 8 pgs.
Response to Restriction Requirement dated Feb. 12, 2009, U.S. Appl. No. 11/097,939, filed Apr. 4, 2005, 2 pgs.
Restriction Requirement dated Feb. 8, 2007, U.S. Appl. No. 11/110,449, filed Apr. 20, 2005, 8 pgs.
Response to Restriction Requirement dated Jun. 7, 2007, U.S. Appl. No. 11/110,449, filed Apr. 20, 2005, 2 pgs.
Restriction Requirement dated Dec. 23, 2008, U.S. Appl. No. 11/187,422, filed Jul. 22, 2005, 11 pgs.
Restriction Requirement dated May 23, 2007, U.S. Appl. No. 11/364,153, filed Feb. 28, 2006, 7 pgs.
Response to Restriction Requirement dated Sep. 24, 2007, U.S. Appl. No. 11/364,153, filed Feb. 28, 2006, 2 pgs.
Restriction Requirement dated Dec. 18, 2006, U.S. Appl. No. 11/381,590, filed Apr. 4, 2006, 7 pgs.
Response to Restriction Requirement dated Mar. 9, 2007, U.S. Appl. No. 11/381,590, filed Apr. 4, 2006, 2 pgs.
Restriction Requirment dated Aug. 18, 2008; U.S. Appl. No. 11/740,959, filed Apr. 27, 2007, 9 pgs.
Response to Restriction Requirment dated Nov. 18, 2008; U.S. Appl. No. 11/740,959, filed Apr. 27, 2007, 6 pgs.
Restriction Requirement dated Aug. 21, 2009, U.S. Appl. No. 11/837,957, filed Aug. 13, 2007, 7 pgs.
Response to Restriction Requirement dated Sep. 21, 2009, U.S. Appl. No. 11/837,957, filed Aug. 13, 2007, 2 pgs.
Restriction Requirement dated Jun. 21, 2010, U.S. Appl. No. 11/956,949, filed Dec. 14, 2007, 7 pgs.
Restriction Requirement dated Feb. 5, 2009, U.S. Appl. No. 11/960,957, filed Oct. 20, 2007, 8 pgs.
Response to Restriction Requirement dated Mar. 4, 2009, U.S. Appl. No. 11/960,957, filed Oct. 20, 2007, 2 pgs.
Restriction Requirement dated Jun. 30, 2009, U.S. Appl. No. 11/997,567, filed Mar. 21, 2008, 7 pgs.
Response to Restriction Requirement dated Jul. 23, 2009, U.S. Appl. No. 11/997,567, filed Mar. 21, 2008, 2 pgs.
Restriction Requirement dated Oct. 7, 2009, U.S. Appl. No. 12/091,848, filed Apr. 28, 2008, 5 pgs.
Response to Restriction Requirement dated Nov. 9, 2009, U.S. Appl. No. 12/091,848, filed Apr. 28, 2008, 9 pgs.
Restriction Requirement dated May 4, 2010, U.S. Appl. No. 12/279,589, filed Sep. 26, 2008, 9 pgs.

Notice of Non-Compliant Amendment dated Jun. 22, 2010 U.S. Appl. No. 12/091,848, filed Apr. 28, 2008, 2 pgs.
Response to Notice of Non-Compliant Amendment dated Jun. 23, 2010 U.S. Appl. No. 12/091,848, filed Apr. 28, 2008, 6 pgs.
RCE dated May 19, 2010, U.S. Appl. No. 12/170,884, filed Jul. 10, 2008, 3 pgs.
Examiner's Interview dated Apr. 15, 2009, U.S. Appl. No. 11/524,268, filed Sep. 21, 2006, 4pgs.
Examiner's Interview dated Oct. 23, 2007, U.S. Appl. No. 11/524,268, filed Sep. 21, 2006, 1 pg.
Notice of Allowance dated Jan. 11, 2010, U.S. Appl. No. 11/524,268, filed Sep. 21, 2006, 7 pgs.
Office Action dated Feb. 11, 2008, U.S. Appl. No. 11/524,268, filed Sep. 21, 2006, 15 pgs.
Office Action dated May 2, 2007, U.S. Appl. No. 11/524,268, filed Sep. 21, 2006, 10 pgs.
Office Action dated Dec. 1, 2008, U.S. Appl. No. 11/524,268, filed Sep. 21, 2006, 16 pgs.
Amendment dated Jun. 1, 2009, U.S. Appl. No. 11/524,268, filed Sep. 21, 2006, 64 pgs.
Response dated Aug. 11, 2008, U.S. Appl. No. 11/524,268, filed Sep. 21, 2006, 15 pgs.
Response dated Nov. 2, 2007, U.S. Appl. No. 11/524,268, filed Sep. 21, 2006, 32 pgs.
Examiner's Search Strategy dated Jan. 11, 2010, U.S. Appl. No. 11/524,268, filed Sep. 21, 2006, 5 pgs.
Examiner's Search Strategy dated Dec. 1, 2008, U.S. Appl. No. 11/524,268, filed Sep. 21, 2006, 4 pgs.
RCE dated Apr. 9, 2010, U.S. Appl. No. 11/524,268, filed Sep. 21, 2006, 2 pgs.
U.S. Appl. No. 13/131,926, filed May 31, 2011, Mazurek et al.
Berge et al., Pharmaceutical Salts, J Pharm Sci., 1977, 66(1):1-19.
Eriksson, Serotonin reuptake inhibitors for the treatment of premenstrual dysphoria, Intl. Clin. Psychopharm, 1999, 14Supp2:S27-S33.
Kumar et al., An Overview of Automated Systems Relevant in Pharmaceutical Salt Screening; Drug Discovery Today, 2007, 12(23-24):1046-1053.
Stahl et al., Handbook of Pharmaceutical Salts: Selection and Use, Helvetica Chim. Acta, 2002, pp. 1-7.
Steiner et al., Seretonin re-uptake inhibitors in the treatment of premenstrual dysphoria: Current status of knowledge, 1997, 1:241-247.
Notice of Allowance dated Feb. 16, 2011; U.S. Appl. No. 12/091,848, filed Apr. 28, 2008, 8 pgs.
Advisory Action dated Feb. 17, 2011; U.S. Appl. No. 11/837,957, filed Aug. 13, 2007, 3 pgs.
Notice of Appeal dated Feb. 22, 2011; U.S. Appl. No. 11/745,515, filed May 8, 2007, 1 pgs.
Notice of Appeal dated Feb. 22, 2011; U.S. Appl. No. 11/554,855, filed Oct. 31, 2006, 1 pgs.
Advisory Action dated Mar. 2, 2011; U.S. Appl. No. 11/745,515, filed May 8, 2007, 3 pgs.
Advisory Action dated Mar. 2, 2011; U.S. Appl. No. 11/554,855, filed Oct. 31, 2006, 3 pgs.
RCE dated Mar. 7, 2011; U.S. Appl. No. 11/837,957, filed Aug. 13, 2007, 2 pgs.
Response to Final Office Action dated Mar. 7, 2011; U.S. Appl. No. 11/837,957, filed Aug. 13, 2007, 9 pgs.
Response to Office Action dated Mar. 14, 2011; U.S. Appl. No. 11/097,939, filed Apr. 4, 2005, 20 pgs.
Interview Summary dated Mar. 15, 2011; U.S. Appl. No. 11/097,939, filed Apr. 4, 2005, 4 pgs.
Interview Summary dated Apr. 6, 2011; U.S. Appl. No. 11/997,567, filed Mar. 21, 2008, 3 pgs.
Response/Amendment dated Apr. 12, 2011; U.S. Appl. No. 11/997,567, filed Mar. 21, 2008, 9 pgs.
Final Office Action dated Apr. 19, 2011; U.S. Appl. No. 11/278,551, filed Apr. 4, 2006, 9 pgs.
Response to Office Action dated May 2, 2011; U.S. Appl. No. 12/390,665, filed Feb. 23, 2009, 11 pgs.
Office Action dated May 27, 2011, U.S. Appl. No. 12/170,884, filed Jul. 10, 2008, 6 pgs.
Office Action dated May 31, 2011; U.S. Appl. No. 11/097,939, filed Apr. 4, 2005, 15 pgs.
Final Office Action dated Jun. 16, 2011; U.S. Appl. No. 11/956,949, filed Dec. 14, 2007, 7 pgs.
Final Office Action dated Jun. 23, 2011; U.S. Appl. No. 11/997,567, filed Mar. 21, 2008, 7 pgs.
Restriction Requirement dated Jun. 29, 2011, U.S. Appl. No. 12/306,945, filed Feb. 9, 2009, 7 pgs.
U.S. Appl. No. 12/987,388, filed Jan. 10, 2011, Pyke.
Anderson et al., Guidelines for choice of selective serotonin reuptake inhibitor in depressive illness, Adv. Psychia. Treatment, 2001, 7:170-180.
Anonymous, Gel significantly increases sexual-activity in surgically menopausal women, Online, Nov. 1, 2004, XP002455243, Retrieved from the Internet: URL:http/www.news-medical.net/print_article.asp?id=5960>[retrieved on Oct. 17, 2007] 8 pgs.
Anonymous: "Hormone Patch May Provide Some Increase in Sexual Desire in Menopausal Women" Jul. 25, 2005; URL:http://pubs.ama-assn.org/media/2005a/0725.dtl, 2 pgs.
Freeman et al., Differential Response to Antidepressants in Women With Premenstrual Syndrome/Premenstrual Dysphoric Disorder, Arch Gen Phych, 1999, 56:932-939.
Yekimov, Sex toys and devices in sexual dysfunction therapy, www.mosmedclinic.ru/conf_library/2002/2/130/, 2002, 6 pgs.
Mutschler et al., The Effect of Drugs: Antidepressive Agents, Manual of Pharmacology and Toxicology, 2001, 8th Ed, pp. 171-172, Scientific Publishing Company PLC, Stuttgart.
Richelson, Pharmacology of Antidepressants, Mayo Clin Proc., 2001, 76:511-527.
Werneke et al., Antidepressants and sexual dysfuntion, Acta Psychia. Scand, 2005, 114:384-397.
Final Office Action dated Jul. 9, 2010; U.S. Appl. No. 11/960,957, filed Dec. 20, 2007, 9 pgs.
Response to Final Office Action dated Jul. 20, 2010; U.S. Appl. No. 11/740,959, filed Apr. 27, 2007, 14 pgs.
Response to Office Action dated Jul. 26, 2010; U.S. Appl. No. 11/837,957, filed Aug. 13, 2007, 11 pgs.
Restriction Requirement dated Oct. 4, 2005; U.S. Appl. No. 10/444,892, filed May 22, 2003, 7 pgs.
Response to Restriction Requirement dated Dec. 1, 2005; U.S. Appl. No. 10/444,892, filed May 22, 2003, 2 pgs.
RCE dated Jul. 20, 2010; U.S. Appl. No. 11/740,959, filed Apr. 27, 2007, 3pgs.
Response to Final Office Action dated Aug. 17, 2010; U.S. Appl. No. 11/097,939, filed Apr. 4, 2005, 22 pgs.
RCE dated Aug. 17, 2010; U.S. Appl. No. 11/097,939, filed Apr. 4, 2005, 3 pgs.
RCE dated Sep. 27, 2010, U.S. Appl. No. 11/837,959, filed Aug. 13, 2007, 2 pg.
Response to Final Office Action dated Sep. 27, 2010, U.S. Appl. No. 11/837,959, filed Aug. 13, 2007, 20 pgs.
Response to Final Office Action dated Sep. 27, 2010 U.S. Appl. No. 11/278,551, filed Apr. 4, 2006, 8 pgs.
Interview Summary dated Jul. 19, 2010; U.S. Appl. No. 11/740,959, filed Apr. 27, 2007, 3pgs.
Final Office Action dated Aug. 20, 2010 U.S. Appl. No. 11/745,515, filed May 8, 2007, 7 pgs.
Final Office Action dated Aug. 30, 2010 U.S. Appl. No. 11/554,855, filed Oct. 31, 2006, 10 pgs.
Notice of Missing Requirements dated Aug. 24, 2010 U.S. Appl. No. 12/675,231, filed Feb. 25, 2010, 2 pgs.
Interview Summary dated Aug. 25, 2010 U.S. Appl. No. 11/278,551, filed Apr. 4, 2006, 3 pgs.
Office Action dated Sep. 14, 2010; U.S. Appl. No. 11/097,939, filed Apr. 4, 2005, 18 pgs.
Interview Summary dated Sep. 15, 2010, U.S. Appl. No. 11/837,959, filed Aug. 13, 2007, 4 pg.
Notice of Allowance dated Sep. 20, 2010 U.S. Appl. No. 12/091,848, filed Apr. 28, 2008, 7 pgs.
Final Office Action dated Oct. 6, 2010; U.S. Appl. No. 11/837,957, filed Aug. 13, 2007, 10 pgs.
Response to Final Office Action dated Oct. 12, 2010; U.S. Appl. No. 11/960,957, filed Dec. 20, 2007, 16 pgs.
Interview Summary dated Oct. 19, 2010; U.S. Appl. No. 11/997,567, filed Mar. 21, 2008, 3 pgs.

Response to Final Office Action dated Oct. 21, 2010; U.S. Appl. No. 11/997,567, filed Mar. 21, 2008, 8 pgs.
RCE dated Oct. 21, 2010; U.S. Appl. No. 11/997,567, filed Mar. 21, 2008, 2 pgs.
Interview Substance dated Oct. 21, 2010; U.S. Appl. No. 11/997,567, filed Mar. 21, 2008, 1 pg.
Office Action dated Oct. 26, 2010, U.S. Appl. No. 11/278,551, filed Apr. 4, 2006, 10 pgs.
Office Action dated Nov. 5, 2010; U.S. Appl. No. 11/956,949, filed Dec. 14, 2007, 10 pgs.
Advisory Action dated Nov. 8, 2010; U.S. Appl. No. 11/960,957, filed Dec. 20, 2007, 3 pgs.
Acknowledgment of Priority Document dated Nov. 4, 2010; U.S. Appl. No. 12/091,848, filed Apr. 28, 2008, 1 pg.
Office Action dated Nov. 12, 2010; U.S. Appl. No. 11/997,567, filed Mar. 21, 2008, 7 pgs.
Notice of Allowance dated Nov. 15, 2010; U.S. Appl. No. 12/091,848, filed Apr. 28, 2008, 4 pgs.
RCE dated Dec. 20, 2010; U.S. Appl. No. 12/091,848, filed Apr. 28, 2008, 3 pgs.
Office Action dated Dec. 30, 2010; U.S. Appl. No. 12/390,665, filed Feb. 23, 2009, 9 pgs.
Response to Final Office Action dated Jan. 20, 2011; U.S. Appl. No. 11/745,515, filed May 8, 2007, 7 pgs.
Response to Final Office Action dated Jan. 20, 2011; U.S. Appl. No. 11/554,855, filed Oct. 31, 2006, 9 pgs.
Response to Office Action dated Jan. 28, 2011, U.S. Appl. No. 11/278,551, filed Apr. 4, 2006, 7 pgs.
Response to Final Office Action dated Feb. 7, 2011; U.S. Appl. No. 11/837,957, filed Aug. 13, 2007, 9 pgs.
FDA (U.S. Food and Drug Administration); Reproductive Health Drugs Advisory Committee Meeting Announcement; URL: http://www.fda.gov/AdvisoryCommittees /Calendar/ucm210886.htm; Jun. 18, 2010; 1 pg.
Background Document for Meeting of Advisory Committee for Reproductive Health Drugs (Jun. 8, 2010); NDA 22-526 Flibanserin; Boehringer Ingelheim; May 20, 2010; 80 pgs.
Briefing Document; Flibanserin (BIMT 17 BS); Boehringer Ingelheim; May 14, 2010; 248 pgs.
FDA (U.S. Food and Drug Administration); Reproductive Health Drugs Advisory Committee Meeting; Draft Agenda; Jun. 18, 2010; 1 pg.
FDA (U.S. Food and Drug Administration); Reproductive Health Drugs Advisory Committee Meeting; Draft Questions to the Committee; Jun. 18, 2010; 1 pg.
FDA (U.S. Food and Drug Administration); Reproductive Health Drugs Advisory Committee Meeting; Draft Meeting Roster; Jun. 18, 2010; 2 pgs.
Advisory Committee for Reproductive Health Drugs—2010 Members; Jun. 2010; 2 pgs.
FDA (U.S. Food and Drug Administration); Reproductive Health Drugs Advisory Committee Meeting; Agenda; Jun. 18, 2010; 2 pgs.
FDA (U.S. Food and Drug Administration); Reproductive Health Drugs Advisory Committee Meeting; Questions to the Committee; Jun. 18, 2010; 1 pgs.
FDA (U.S. Food and Drug Administration); Reproductive Health Drugs Advisory Committee Meeting; Meeting Roster; Jun. 18, 2010; 2 pgs.
(Slides) Division of Reproductive and Urologic Drug Products Advisory Committee Meeting; Flibanserin (NDA-22526); Boehringer Ingelheim; Jun. 18, 2010; 110 pgs.
Press Release May 19, 2010; women with hypoactive sexual desire disorder (HSDD) report that fibanserin increased their sexual desire and reduced associated distress; http://www.boehringer-ingelheim.com/news/news releases/press releases/2010/19 May 2010; 4 pgs.
Press Release Jun. 17, 2010; Key Facts on HSDD and Flibanserin; http://us.boehringer-ingelheim.com/news events/press releases/press release archive/2010; 2 pgs.
Press Release Jun. 18, 2010; Boehringer Ingelheim comments on Jun. 18th FDA Advisory Committee Meeting; http://us.boehringer-ingelheim.com/news events/press releases; press release archive/2010; 2 pgs.

FDA (U.S. Food and Drug Administration); Transcript of Advisory Committee for Reproductive Health Drugs; Jun. 18, 2010; 293 pgs.
U.S. Appl. No. 08/039,002, filed Mar. 25, 1993, Bietti.
U.S. Appl. No. 11/956,949, filed Dec. 14, 2007, Lewis-D'Agostino, et al.
U.S. Appl. No. 12/390,665, filed Feb. 23, 2009, Wunderlich, et al.
U.S. Appl. No. 12/532,269, filed Dec. 14, 2009, Boeck, et al.
U.S. Appl. No. 12/675,231, filed Feb. 25, 2010, Hanes, et al.
Anonymous, Hormone Patch may Provide Some Increase in Sexual Desire in Menopausal Women, Jul. 25, 2005, URL:http://pubs.ama-assn.org/media/2005a/0725.dtl.
Bechard, et al., Int. J. Pharm., 1992, 87:133-139.
Braiman, Psychosexual disorders of young adulthood, Clin Obstetrics and Gynecology, 1970, 13(3):734-745.
Byrn, et al., Hydrates and Solvates, Solid State Chemistry & Drugs, 1999, Chpt. 11, pp. 233-247.
Buhrich, et al., Can fetishism occur in transexuals?, Arch Sex Behav, 1977, 6(3):223-235.
Butts, The relationship between sexual addiction and sexual dysfunction, J. Health Care Underserved, 1992, 3(1):128-35; discussion 136-7.
Buvat, et al., Role of hormones in sexual dysfunction, homosexuality, transsexualism, and paraphilia related disorders. Diagnostic and therapeutic consequences, Contracept Fertil Sex, 1996, 24(11):834-846—only English abstract.
Bymaster, et al., Fluoxetine, but not other selective serotonin uptake inhibitors, increases norepinephrine and dopamine extracellular levels in prefrontal cortex, Psychopharmacology, 2002, 160:353-361.
Chiao, et al., Remington Pharm 19th Ed., Panamerican Spain, 1988, pp. 2535-2537.
Cooper, et al., A female sex offender with multiple paraphilias: a psychologic, physiol ogic (laboratory sexual arousal) and endocrine case study, Can J Psychiatry, 1990, 35(4):334-7.
Grau, et al., Risk Factors, Outcome, and Treatment in Subtypes of Ischemic Stroke: The German Stroke Data Bank, Stroke, 2001; 32:2559-2566.
Guarraci, et al: Coffee, Tea and Me: Moderate doses of caffeine affect sexual behavior in female rats, Pharma Biochem and Behavior, Nov. 2005, 82(3):522-530. ISSN: 0091-3057 Elsevier, US, abstract.
Kafka, A Monoamine Hypothesis for the Pathophysiology of Paraphilic Disorders, Archives of Sex Behav, 1997, 26(4):343-58.
Marshall, et al., Unified Approach to the Analysis of Genetic Variation in Serotonergic Pathways, Am J. Med. Genetics Neurophychiatric Genetics, 1999, 88:621-627.
Moser, Lust, lack of desire and paraphilias: some thoughts and possible connections, Marital Ther, 1992, 18(1):65-9.
Otsuka, et al., Chem. Pharm. Bull., 1999, 47(6):852.856.
Pharmacopia, 1995, p. 1843.
Schwartz, et al., Conceptual factors in the treatment of paraphilias: a preliminary rep., Maritial Ther, 1983, 9(2):3-18.
Semkova, et al., Neuroprotective effect of 5-HT1A receptor agonist, Bayx3702, demonstrated in vitro and in vivo, Euro J Pharm, 1998, 359:251-260.
Singhal, et al., Advanced Drug Delivery Reviews, 2004, 56:335-347.
Soederberg, et al., Leptin is a Risk Marker for First-Ever Hemorrhagic Stroke in a Population-Based Cohort, Stroke, Jl of the Am Heart Assoc., 1999; 30:328-337.
Stedman's Medical Dictionary definition "Anxiety", 28th Ed., 2006, p. 114, Lippincott Williams & Wilkins, Baltimore MD.
Thrombolytic Therapy: MedlinePlus Medical Encyclopedia, http:/www.nlm.nih.gov/medlineplus/ency/article/007089.htm, accessed Dec. 17, 2009, pp. 1-4.
Vippagunta, Adv. Drug Del. Rev., 2001, 48:3-26.
Welsh, et al., Effect of Lactacidosis on Pyridine Nucleotide Stability During Ischemia in Mouse Brain, J Neurochemistry, 1987, 49(3):846-851.
Zverina, et al., The occurrence of atypical sexual experience among various female groups, Arch Sex Behav, 1987, 16(4):321-6.
International Search Report PCT/EP 02/11103-WO 03035072-, mailed Jan. 14, 2003.

* cited by examiner step b)

Step c)

step d)

step e)

step f)

Step d)

step e)

step f)

step b)

Step c)

step d)

step e)

CONTROLLED RELEASE SYSTEM AND METHOD FOR MANUFACTURING THE SAME

This application claims the benefit of priority to EP 06 017 754, filed Aug. 25, 2006, the contents of which are incorporated herein by reference in its entirety.

FIELD OF THE INVENTION

The present invention is directed to a controlled release system, particularly for oral administration, of active substances with pH-dependent solubility characteristics and a method for the production thereof.

BACKGROUND OF THE INVENTION

As commonly known, controlled release of active substance(s) allows to simplify the patient's administration scheme by reducing the amount of recommended daily intakes, improves patient's compliance, attenuates adverse events, e.g. related to high plasma peaks and improves the bioavailability of the active substance(s). Pharmaceutical controlled release preparations regulate the release of the incorporated active substance(s) over time and comprise formulations e.g. with a prolonged, a sustained, a delayed, a slow or an extended release, so they accomplish therapeutic or convenience objectives not offered by conventional dosage forms such as solutions or promptly dissolving immediate release dosage forms.

There exists always a need to improve the known release systems in order to improve the effectivity of the contained active substances.

Many oral controlled release dosage forms are designed to deliver the doses of a drug at a regulated rate so as to achieve zero-order release kinetics. Irrespective of the type of dosage form, drug solubility and hence absorption depends to a large extent upon the constant changing environmental conditions within the gastrointestinal tract. Many drugs are weak acids or weak bases, or the salts thereof. Therefore, the pH value plays a significant role in the dissolution rate of weakly acidic or weakly basic compounds. It follows therefore that an oral release solid dosage form e.g. containing a weakly basic drug may potentially lead to bioavailability problems. As the drug enters the small intestine, the pH rises to pH 5.5 or higher. In this environment the solubility of a weakly basic drug often decreases greatly and this might translate to a markedly decreased release and absorption in vivo. Therefore, it exists a need to overcome said deficiencies.

In prior art a number of approaches is described which provides a controlled release system. A variety of patent applications relate to pharmaceutical compositions which focus on the fact that the active substance is contained in the core:

For example EP 0 436 370 A1 and U.S. Pat. No. 5,395,628 describe a controlled release pharmaceutical preparation comprising (a) a core containing a pharmaceutically active substance and an organic acid, and (b) a coating film formed on the surface of the core by aqueous coating of a water-insoluble and slightly water-permeable acrylic polymer containing a trimethylammonium-ethyl group.

Furthermore, WO 00/19984 and U.S. Pat. No. 6,878,387 B1 relate to a pharmaceutical preparation consisting of (a) a core containing an active substance, optionally an excipient and common pharmaceutical additives in addition to the salt of an inorganic acid whose proportion in the weight of the core ranges from 2.5 to 97% by weight and (b) an outer film coating consisting of one or more (meth)acrylate copolymers and optionally common pharmaceutical adjuvants, wherein 40 to 100% by weight of the (meth)acrylate copolymers consist of 93 to 98% by weight of radically polymerized $C_1$- to $C_4$-alkylesters of acrylic or methacrylic acid and 7 to 2% by weight of (meth)acrylate monomers with a quaternary ammonium group in the alkyl radical. Preferably the polymers are selected from Eudragit® RS or Eudragit® RL.

However, the systems containing the active substance in the core have disadvantages because the effectivity is not always reliable and the control of dissolving and release of the active substance is not in each and every case sufficient satisfying. Additionally, numerous active substances display a more or less marked tendency to hydrolytic decomposition in the presence of acids and traces of water. In individual cases there may even be a direct chemical reaction between the active substance and organic acids, e.g. ester formation. Therefore, the pharmaceutical preparation does not remain stable when stored.

Furthermore, in prior art controlled release pellets as shown in FIG. 1. are known wherein anions of salts in the core (1) thereof interact via an intermediate layer (2) (modulating layer) with cationic groups of polymers in the outmost coating layer (4) (controlled release layer). Such a composition is described to influence the release of coated pharmaceutical forms during in vitro release. The modulating layer (2) is a neutral polymer layer such as Eudragit® NE. The modulating layer (2) is layered with a drug layer (3) and further coated with controlled release methacrylate polymer having quaternary ammonium ions such as Eudragit® RL/Eudragit® RS as outmost layer (4). According to the supposed release mechanism the ions of core (1) interact with the controlled release layer (4) leading to alterations in hydration of the outmost layer (4) which causes a change in the permeability of said outest layer (4). In other words using the properties of the ion exchanger Eudragit® RS or RL in the outmost layer (4) allows for the change of the permeability of said outest layer in order to control the solubility of the drug. Such controlled release pellets are commercially available under the trademark EUDRAMODE™ by Degussa, Pharma Polymers, Darmstadt.

However, the above controlled release pellets are only tested in vitro and the mechanism based on the above-described ionic interactions resulting in a change of the permeability of the outest layer is very complicated and does not allow a reliable control of the release system. Further the effectivity of an in vivo system is not clarified.

Finally, US 2005/0095293 A1 relates to a pharmaceutical composition with a bioavailability of an active substance which is substantially independent of the gastric pH, for oral administration of active substances with pH-dependent solubilities and a dose number of more than 1 at a pH>5, comprising a plurality of pellets synthesised in each case from a) a core material, b) an optional insulating layer, c) an active substance layer and d) an optional coating, wherein the core material consists of one or more pharmaceutically acceptable organic acid(s) with a water solubility of more than 1 g/250 ml at 20° C., optionally with the addition of binders or other technological adjuvants.

However, the release characteristics of said system of prior art are not always satisfying.

It is therefore an object of the present invention to provide an improved controlled release pharmaceutical system which avoids the disadvantages of the prior art and which allows for a reliable control of the dissolution and release of the pharmaceutically active substance. Furthermore, it shall be possible to adjust a release profile of the active substance which is virtually independent from the pH values of the environmental medium. Furthermore a method of manufacturing the system shall be provided.

DESCRIPTION OF THE INVENTION

Surprisingly, it has been found that a specific build-up of a release system makes it possible to readily control and adjust the desired release profile, the formulation principles allow a release profile which is independent from the pH value.

Therefore, the present invention provides a pharmaceutical controlled release system for administration, particularly oral administration, of active substances with pH-dependent solubilities, comprising
a) a core material containing or consisting of one or more pharmaceutically acceptable pH modifiers;
b) optionally an insulating layer,
c) a first layer, particularly for protection of the layer(s) beneath and/or for further controlling of the release of the pH-modifier, containing or consisting of one or more pharmaceutically acceptable water-insoluble polymers;
d) a second layer containing or consisting of at least one active substance having a pH-dependent solubility;
e) a third layer, which preferably represents a further controlled release layer, containing or consisting of one or more pharmaceutically acceptable polymers having anionic or no ionic groups; and
f) optionally a fourth layer, for example in form of a secondary controlled release outer coating, preferably for controlling release in the stomach or a non-functional coating.

It is therefore provided a controlled release system, particularly for oral administration, of one or more active substances with pH-dependent solubility characteristics which guarantees largely pH-independent bioavailability of the active substance.

In the frame of the present invention the term "controlled release" should be understood in contrast to an immediate release, the active ingredient is gradually, continuously liberated over time, sometimes slower or faster, but independent from the pH value. In particular, the term indicates that the system does not release the full dose of the active ingredient immediately after oral dosing and that the formulation allows a reduction of peak plasma concentration and/or in dosage frequency. The controlled release is a pH-controlled release either triggered by the pH of the absorption side and/or the pH-modifier of the core, whichever applies first.

A "system" should be understood in its broadest meaning comprising any type of formulation, preparation or pharmaceutical dosage form providing a number of layers as required according to the present invention. The controlled release system may be in form of pellets, tablets, matrix tablet, mini-tablest, micro capsules or granules. The system may be administered directly or filled in another form such as a capsule or compressed into tablets together with suitable fillers.

The structure, composition and build-up of the combination of layers make it possible to provide an improved control of the release system avoiding the disadvantages of prior art.

Since the pH modifier is spatially separated from the active substance in the formulation of the controlled release system of the present invention it remains stable when stored, undesirable interactions between pH modifier and active substance are prevented. Only after the oral administration of the controlled release system of the present invention the pH modifier does dissolve and produces a micro environment in which the active substance can dissolve.

In the following the optional and obligatory layers will be described in detail.
a) Core Material The core material contains at least one pH modifier. The pH modifier is not limited according to the present invention but any known chemical substance capable of providing a modified pH value may be used. Usually the pH modifier may be selected from one or more organic acids and/or organic bases and/or buffers or mixtures thereof. The pH modifier is selected to control the solubility of the active substance, i.e. the type(s) of pH modifier selected and the amount of pH modifier adjusted has an impact on or triggers the release of the active substance. Therefore, the choice of the pH modifier strongly depends from the active substance(s) to be used. The pH modifier controls the pH to be adjusted for the active substance(s); in contrast to prior art the pH modifier of the present invention has no influence on the permeability of any outer layer.

The organic acids, bases or buffers are not limited according to the frame of the present invention but any acid, base or buffer usable in pharmaceuticals may be employed. Therefore, the pH modifier is selected from the group consisting of one or more pharmacologically acceptable organic acids, one or more pharmaceutically acceptable bases, one or more pharmaceutically acceptable buffers, derivatives and mixtures thereof.

The term "one or more" or "at least one" as used in the present invention stands for 1, 2, 3, 4, 5, 6, 7, 8, 9, 10 compounds or even more. Preferred embodiments comprise 1, 2 or 3 such compounds. More preferred embodiments comprise 1 or 2 such compounds and even more preferred are embodiments comprising one of such compounds.

The pH modifier may be in solid or liquid form. The pH modifier is not necessarily used in the form of a solid or mixture of solids but it may be employed in form of a liquid or mixtures of liquids, for example, by firstly adhering or coating the pH modifier onto a carrier or carrier particles and then forming the core containing the pH modifier. For instance, the adhering or coating can be carried out by a conventional coating method which is usually used in the preparation of pharmaceutical preparations, such as fluidized bed coating, pan coating, or the like. The inert carrier may include particles of a carrier substance, such as sucrose, lactose, starches, crystalline cellulose, calcium phosphates, silicium dioxide and derivatives thereof, and the like.

The pharmaceutically acceptable organic acids and/or bases to be contained in the core may be preferably selected from the group consisting of acetic acid, adipic acid, ascorbic acid, I-alanine, arginine, asparagines, aspartic acid, benzenesulphonic acid (besylate), benzoic acid, p-bromophenylsulphonic acid, camphorsulphonic acid, carbonic acid, gamma-carboxyglutamic acid, citric acid, cysteine, ethanesulphonic acid, fumaric acid, particularly cis-fumaric acid and/or trans-fumaric acid, gluconic acid, glutamic acid, glutaric acid, I-glutamine, hydrobromic acid, hydrochloric acid, hydroiodic acid, isethionic acid, isoleucine, lactic acid, I-leucine, lysine, maleic acid, malic acid, malonic acid, mandelic acid, methanesulphonic acid (mesylate), methionine, mucinic acid, nitric acid, ornithine, oxalic acid, pamoic acid, pantothenic acid, phosphoric acid, serine, sorbic acid, succinic acid, sulphuric acid, tartaric acid, p-toluenesulphonic acid, tyrosine glutamic acid, valine and derivatives and mixtures thereof. The above listing is not intended to be of limitative character, the skilled person is familiar with further examples.

Particularly preferred organic acids are acetic acid, ascorbic acid, tartaric acid, glutaric acid, malic acid, fumaric acid, citric acid, lactic acid, adipic acid and succinic acid or combinations thereof.

As derivatives e.g. the hydrates or the salts of the acids may be used such as alkali and earth alkali salts or ammonium salts. The preferred type depends on the intended use of the controlled release system. Particularly preferred are salts of weak organic acids such as succinic acid, fumaric acid, malic acid, tartaric acid, glutaric acid, citric acid, formic acid, acetic acid, adipic acid, ascorbic acid, maleic acid, or lactic acid. Particularly suitable salts are sodium succinate, sodium citrate, and sodium acetate.

The buffer is preferably selected from one or more pharmaceutically acceptable or compatible buffers or buffering agents for example McIlvaine buffers (for example citric acid phosphate buffer, pH 2.2-7.0), ammonia solution, calcium carbonate, tribasic calcium phosphate, citric acid monohydrate, dibasic sodium or potassium phosphate (for example pH 5.0-8.0), diethanolamine, malic acid, monobasic sodium phosphate, monoethanolamine, monosodium glutamate, phosphoric acid, potassium citrate, sodium acetate, sodium bicarbonate, sodium borate, sodium citrate dihydrate, sodium hydroxide, sodium lactate, triethanolamine and derivatives and mixtures thereof.

The core material used is preferably a pharmaceutically acceptable pH modifier to which 0 to 50% by weight, preferably 0.1 to 25% by weight, more preferably 1 to 10% by weight, even more preferably 2 to 8% by weight, and most preferably 3 to 6% by weight of a suitable binder is optionally added.

The content of the pharmaceutically acceptable pH modifier(s) is usually between 30 and 100% in the core material. However, it is also possible to use pure (100%) pH modifier as the starting material, then it may be advantageous to use a sufficiently narrow range of particle sizes.

It should be noted that the ranges of values given herein expressly include all the numerical values, both whole numbers and fractions, within the ranges as specified. The numerals given are always the percent by weight values. Percent by weight value means the percentage with respect to an individual part of the dosage form like the core or the coating.

As binder, it is possible to use any binder usually employed in pharmaceuticals. Exemplarily mentioned are naturally occurring or partially or totally synthetic polymers selected from among acacia, agar, gum arabic, alginic acid, carbomers, carrageenan, ceratonia, chitosan, confectionar's sugar, copovidone, povidone, cottonseed oil, dextrate, dextrin, dextrose, polydextrose, maltodextrin, maltose, cellulose and derivatives thereof such as microcrystalline cellulose, methylcelluloses, hydroxypropyl methyl celluloses, ethylcelluloses, hydroxyethyl celluloses, hydroxyethyl methylcelluloses, hydroxypropyl celluloses, carboxymethylcelluloses, carmellose sodium, hypromelloses (cellulose hydroxypropyl methylether), cellulose acetate phthalate, starch and derivatives thereof, such as pregelatinized starch, hydroxypropylstarch, corn starch, gelatin, glyceryl behenate, guar gum, hydrogenated vegetable oils, inulin, lactose, glucose, magnesium aluminium silicate, poloxamer, polycarbophils, polyethylene oxide, polyvinylpyrrolidone, copolymers of N-vinylpyrrolidone and vinyl acetate, polymethacrylates, alginates such as sodium alginate, stearic acid, sucrose, sunflower oil, zein as well as derivatives and mixtures thereof.

The term "derivatives" according to the present invention is meant to include any compound derived from the mentioned compounds as basic system, for example by substitution with one or more functional groups. This belongs to the general knowledge of the skilled person.

Particularly preferred binders are gum arabic, hydroxypropyl celluloses, hydroxypropyl methylcelluloses, methylcelluloses, hydroxyethyl celluloses, carboxymethylcelluloses, carmellose sodium, povidone, corn starch, polyvinylpyrrolidone, the copolymers of N-vinylpyrrolidone and vinyl acetate, or combinations of these polymers. The above listing is not intended to be of limitative character, the skilled person is familiar with further examples.

As a matter of course also other additives, excipients, carriers, technological adjuvants suitable in pharmaceutical formulations may be present such as lubricants, glidants, agents to improve flowability, granulating agents, anti-caking agents, agglomeration inhibitors, pore formers, anti-adherents, anti-tacking agent, anti-sticking agent, flavors, aromatiziers, dyes or colorants, preservatives, plasticizers, diluents, wetting agents, sweeteners, disintegrants, tonicity agents, chelating agents, stabilizers, solubilizers, antioxidants, fillers, pigments and the like. These pharmaceutically acceptable formulating agents are e.g. present in order to promote the manufacture, compressibility, appearance and/or taste of the preparation. Other conventional additives known in the art can also be included. The above listing is not intended to be of limitative character, the skilled person is familiar with further examples.

The core material which may be spherical, has preferably an average diameter of 0.1-5 mm, more preferably 0.2-2 mm and most preferably 0.4-1.5 mm. Actually, the core to be coated may be in any suitable form such as crystals, microparticulates, beads, tablets, capsules, pills, pellets, granules, or fine granules. The core can be manufactured by techniques generally known in the art such as direct pressing, extrusion and followed by forming to preferably rounded shape, moist or dry granulation or direct pelleting, for example on plates or rotor pelletizers, or by binding of powders, such as powder layering on spherules (nonpareils). The core which is free of active substance can be homogeneous or can have a layered structure or any other build-up known by those skilled in the art.

b) optional insulating mobility decreasing layer

To coat the core material before the application of the further layer(s) with an insulating/mobility decreasing layer based on a water-soluble, pharmaceutically acceptable polymer may be advantageous for two reasons:

I) To increase the durability of the finished core product material.

II) To decrease the mobility of the pH modifier and control interactions between the pH modifier and the following layer (first layer), especially if the first layer contains Eudragit® RS.

Examples of such water-soluble polymers include gum arabic or a partially or totally synthetic polymer selected from the alkyl celluloses and derivatives thereof such as methylcelluloses, hydroxyalkyl celluloses and derivatives thereof such as hydroxyethyl celluloses, hydroxypropyl celluloses, hydroxyalkyl alkylcelluloses and derivatives thereof such as the hydroxypropylmethyl celluloses, carboxyalkyl-celluloses such as carboxymethylcelluloses, polyvinylpyrrolidones, copolymers of N-vinylpyrrolidone and vinyl acetate or combinations of said polymers and derivatives and mixtures thereof. Gum arabic or a hydroxyalkyl alkylcellulose such as hydroxypropyl methylcellulose is preferably used. If desired, the coating with the water-soluble, pharmaceutically acceptable polymer may be carried out with the addition of excipients, preferably one or more suitable plasticizers, one or more separating agents and/or one or more pigments.

Exemplarily mentioned plasticizers are citrates such as acetyltributyl citrate, acetyltriethyl citrate, tributyl citrate, triethyl citrate, benzyl benzoate, castor oil, phthalates such as dibutyl phthalate, diethyl phthalate, dimethyl phthalate, dimeticon, fractionated coconut oil, chlorbutanol, dextrin, sebacate such as dibutyl sebacate, glycerine, glycerine derivatives such as glycerine monostearate, glycerol triacetate (triacetin), acetylated monoglyceride, mannitol, mineral oil, lanolin alcohols, palimitic acid, 2-pyrrolidone, sorbitol, stearic acid, triethanolamin, polyethyleneglycols (all types at different molecular weights of PEGs), and propylene glycol, and derivatives and mixtures thereof. Preferred plasticizers which may be used are acetylated monoglyceride, acetyltributyl citrate, acetyltriethyl citrate, dibutyl phthalate, dibutyl sebacate, diethyl phthalate, dimethyl phthalate, tributyl citrate, triethyl citrate, polyethylene glycols (all types at different molecular weights of PEGs), and propylene glycol. Particularly preferred are triethyl citrate, tributyl citrate, polyethyleneglycols (all types at different molecular weights of PEGs), and propylene glycol.

Exemplarily mentioned separating agents are talc, silicic acid and glycerol monostearate.

Examples of pigments which are especially useful are titanium dioxide, iron oxide pigments, and some of the aluminium lakes as well as pigment black, pigment white, pigment yellow, sunset yellow, sunset yellow lake, quinoline yellow lake and the like.

Other additives, excipients, carriers, technological adjuvants, if desired, may be present.

The application quantity of the optional (first) insulating layer based on the specific surface area of the starting core is for case I): in the range from 0.05 to 5.0 mg/cm$^2$, preferably 0.1 to 3.0 mg/cm$^2$, more preferably 0.15 to 2.5 mg/cm$^2$, particularly 0.2 to 2.0 mg/cm$^2$ and more particularly 0.2 to 1.5 mg/cm$^2$, for case II): in the range from 0.1 to 30.0 mg/cm$^2$, preferably 0.2 to 20 mg/cm$^2$, more preferably 0.5 to 15 mg/cm$^2$, particularly 0.7 to 12 mg/cm$^2$ and more particularly 1 to 10 mg/cm$^2$.

c) First Layer

The first layer is provided directly on the core or on the optional insulating layer or another intermediate layer being applied on the core or the insulating layer and preferably serves as a control layer in order to support the controlled release desired. In addition, the first layer may also serve as a protective layer of the layer(s) beneath, particularly the core material. The first layer is based on a water-insoluble polymer. The water-insoluble polymer is not limited according to the present invention. Any type of pharmaceutically acceptable water-insoluble polymer may be used. The term "water-insoluble" may be understood that the compound has a solubility in water which is below 0.1 mg/ml at room temperature.

Preferably the water-insoluble polymer contained in the first layer is selected from the group consisting of an acrylic and/or methacrylic polymer which may contain a low content of quaternary ammonium groups in the alkyl moiety such as trimethylammonium-groups, alkylcelluloses such as ethylcelluloses, methylcelluloses, cellulose acetate, and polyvinyl acetate and derivates and mixtures thereof.

Preferably, the water-insoluble polymer may comprise polymers or copolymers of acrylic acid, methyl acrylate, ethyl acrylate, methacrylic acid, methyl methacrylate, ethyl methacrylate and the like which may contain quaternary ammonium groups such as ammonio (meth)acrylate copolymers. Preferred examples are copolymers of ethyl acrylate, methyl methacrylate and trimethylammonioethyl methacrylate chloride. Such an acrylic polymer is available under the name Eudragit® RS which is a water-insoluble copolymer (poly(ethyl acrylate, methyl methacrylate, trimethylammonioethyl methacrylate chloride) 1:2:0.1, manufactured by Rhöm Pharma, Germany) e.g. in form of organic-based polymeric solutions or aqueous-based polymeric dispersions thereof which may be used for coating, for example Eudragit® RS 30D. Another acrylic polymer may be Eudragit® RL which consists of the same components as Eudragit® RS but has a different molar ratio (Eudragit® RL: poly(ethylacrylate, methyl methacrylate, trimethylammonioethyl methacrylate chloride; 1:2:0.2) e.g. in form of organic-based polymeric solutions or aqueous-based polymeric dispersions thereof, for example Eudragit® RL 30D. The presence of quaternary ammonium groups appears to take advantage of ionic interactions for the release of the active substance. This interaction can be additionally altered in an advantageous way exchanging the originally counter cation (chloride) of Eudragit® RS or RL against anions which display a higher attraction towards the quaternary ammonium group than chloride (R. Grützmann, Thesis 2005, University of Tübingen, Germany, "Zum Mechanismus der Anionenwirkung auf die Permeabilität kationischer Polymethacrylatüberzüge"). This effect can be used in an advantageous way at any step poly(ethyl acrylate, methyl methacrylate, trimethylammonioethyl methacrylate chloride) is used in this invention without being mentioned again. Not being bound by any theory it is assumed that an ion induced transport may occur wherein ionic interactions between solved anions released from the core and the cationic quaternary ammonium ions of the first layer take place. The release rate depends among other things from the anion species and the ratio of anions/cations present.

Also preferably used are, for example, poly(ethyl acrylate, methyl methacrylate) 2:1 (Eudragit® NE) e.g. in form of aqueous-based polymeric dispersions thereof, for example Eudragit® NE 30D, Kollicoat® EMM 30D; and ethylcelluloses e.g. in form of organic-based polymeric solutions or aqueous-based polymeric dispersions thereof, for example, ethylcellulose N10, N20 or N45, Aquacoate® ECD, and Surelease®.

Furthermore preferably mentioned are cellulose acetate e.g. in form of organic-based polymeric solutions thereof and/or polyvinyl acetate e.g. in form of aqueous-based polymeric dispersions thereof, for example Kollicoat® SR 30D.

The mentioned polymers may be used alone or in combination of two or more polymers. The selection of the water-insoluble (co-)polymer or mixtures of (co)polymers have an influence on the release of the active substance in order to establish the desired release profile. Although the active substance has a pH-dependent solubility it is possible to adjust a release profile which is independent from the pH value resulting in an improved bioavailability. Depending on the active substance used and the further structure of the release system the profiles may be further adjusted. For example, if the viscosity of the water-insoluble polymer used is enhanced, the retardation of the release of the active substance may be increased (for example the viscosity is enhanced from ethylcellulose N10->N20->N40).

Other additives including but not limited to, plasticizers, glidants, anti-tacking agents, surfactants, pigments and other coloring agents and/or pore formers may be present in an amount up to 70% of the entire layer, depending on the polymer used which belongs to the general knowledge of the skilled person. Preferably one or more plasticizers are present, particularly those as already described. Preferably used plasticizers are selected from the group consisting of acetylated monoglyceride, acetyltributyl citrate, acetyltriethyl citrate, castor oil, dibutyl phthalate, dibutyl sebacate, diethyl phthalate, dimethyl phthalate, fractionated coconut oil, glycerin, glycerine triacetate (triacetin), tributyl citrate, triethyl citrate, polyethylene glycols (all types at different molecular weights of PEGs), and propylene glycol.

Therefore, the first layer may be obtained using organic-based polymeric solutions or aqueous-based polymeric solutions or dispersions to be sprayed onto the starter core, which preferably contain or consist of one or more water-insoluble polymer as above-described and preferably excipients, e.g. with or without plasticizer(s), with or without anti-tacking agent(s), with or without pore-former(s) and/or solvent(s) and/or vehicle(s).

An anti-tacking agent, anti-sticking agent or glidant or agent to improve flowability can be used to improve powder flow properties prior to and during the manufacturing process and to reduce caking. A lubricant and agglomeration inhibitor can be used to enhance release of the dosage form from the apparatus on which it is formed, for example by preventing adherence to the surface of an upper punch ("picking") or lower punch ("sticking"). Among this group of excipients may be exemplarily mentioned boric acid, calcium silicate, cellulose, particularly powdered cellulose, colloidal silicon dioxide (e.g. Aerosil®, Cab-O-Sil®), DL-leucine, magnesium silicate, magnesium trisilicate, talc, silicon dioxide, starch, tribasic calcium phosphate, glyceryl behenate (e.g. Compritol® 888), magnesium oxide, mineral oil, poloxamer, polyvinyl alcohol, hydrogenated oils such as hydrogenated vegetable oils (e.g. Sterotex®), hydrogenated castor oil, kaolin, (light) mineral oil, canola oil, triglycerides, such as medium-chain triglycerides, myristic acid, palmitic acid, polyethylene glycols (all types at different molecular weights of PEGs), benzoate such as sodium or potassium benzoate, sodium chloride, sodium lauryl sulfate, magnesium lauryl sulphate, sodium acetate, sodium benzoate, sodium fumarate, sodium oleate, sodium stearyl fumarate, talc, stearic acid and salts including magnesium, calcium, sodium and zinc stearate, glycerol monostearate, glyceryl palmitostearate, macrogol, like macrogol 400 or 6000, polyoxyl-40-stearate, waxes and the like.

Possible surfactants are lecithin, polysorbate 80, sodium lauryl sulfate, poloxamers, polyethylene glycol, sucrose fatty acid esters, polyoxyethylene hardened castor oil, polyoxyethylene fatty acid ester, polyoxyethylene glycol, polyoxyethylene sorbitan fatty acid ester, alkylbenzene sulfonate, sulfosuccinate ester salts, hydroxypropylcellulose, ammonium lauryl sulfate, and other alkyl sulfate salts, sodium laureth sulfate, cetyl trimethylammonium bromide (CTAB), hexadecyl trimethyl ammonium bromide, and other alkyltrimethylammonium salts, cetyl pyridinium chloride, polyethoxylated tallow amine (POEA) benzalkonium chloride, dodecyl betaine, dodecyl dimethylamine oxide, cocamidopropyl betaine, coco ampho glycinate, alkyl polyglucosides, including octyl glucoside and decyl maltoside, cetyl alcohol, oleyl alcohol and cocamide or mixtures thereof.

The application quantity of the of the surfactants based on the whole amount of the first layer is in the range from 0 to 10% by weight, preferably from 0.5 to 5.0% by weight, and more preferably from 1 to 3% by weight.

Possible pore formers are methylcellulose, hydroxypropyl methylcelluloses, hydroxypropyl cellulose, hydroxyethyl cellulose, povidone (e.g. Kollidon 17), Eudragit® E (Poly (butyl methacrylate, (2-dimethylaminoethyl)methacrylate, methyl methacrylate) 1:2:1), alginic acid and salts thereof including calcium, potassium, propylene glycol, and sodium alginate, gelatin, povidone, and polyvinyl alcohol.

The application quantity of the first layer based on the specific surface area of the starting core is in the range from 0.1 to 15 mg/cm$^2$, preferably 0.5 to 12 mg/cm$^2$, more preferably 1.0 to 10 mg/cm$^2$, particularly 1.5 to 8.0 mg/cm$^2$ and more particularly 2.0 to 6.0 mg/cm$^2$.

In a preferred embodiment of the present invention the first layer comprises a polymer selected from the group consisting of Eudragit® RS, Eudragit® RL, Eudragit® NE, ethylcellulose (N10, N20 or N45) and/or mixtures thereof in an amount of 2.0 to 4.5 mg/cm$^2$ (calculated as dry matter of the polymer or polymer mixture), a plasticizer from the group consisting of acetyltributyl citrate, acetyltriethyl citrate, dibutyl phthalate, dibutyl sebacate, diethyl phthalate, dymethyl phthalate, glycerin triacetate (triacetin), tributyl citrate, triethyl citrate, polyethylene glycols in an amount 10 to 30% (w/w, based on the dry polymer/polymer-mixture matter of the layer) and an anti-tacking agent, anti-sticking agent or glidant from the group consisting of glycerol monostearate, talc or polyethylene glycol in an amount of 0 to 20% (w/w, based on the dry polymer/polymer-mixture matter of the layer).

It is also possible to control the release of the active substance based on the quantity of the applied layer. For example if the application amount is increased, the retardation effect will be increased. However, increased layer thickness is not desired due to increasing costs and increasing weight of the application form. Further the ratio active substance/excipients will be unfavourable resulting in a poor compliance of the patient. As a result, it is a better way to control release by the composition and structure of the layers used.

d) Second Layer

The second layer contains at least one active substance having a pH-dependent solubility. The term "active substance" for the purposes of this invention refers to any pharmacologically effective compound which (as such or in the form of the pharmaceutically acceptable salts or derivatives thereof) having a pH-dependent solubility. That is the solubility of said active substance changes due to a change in the pH value.

For example the active substance may be a weak base which in the range from pH 1 to pH 7.5 exhibits pH-dependent solubility characteristics, i.e. with greater solubility under acidic conditions and lesser solubility under basic conditions. In these active substances, in fact, the bioavailability may be dependent on the pH in the gastrointestinal tract when, for example, administered orally. This dependency is avoided according to the present invention.

The pharmaceuticals used within the meaning of the invention are intended for oral administration in the human or animal body in order to cure, alleviate, prevent or detect diseases, injuries, body damage or pathological conditions; to allow the nature, condition or functions of the body or mental conditions to be discerned; to replace active principles or body fluids generated by the human or animal body; to combat, eliminate or render harmless pathogens, parasites or substances foreign to the body; or to influence the nature, condition or functions of the body, mental conditions or any kind of disorders.

According to the present invention the active substance is not limited, there can be used all active principles that have a pH-dependent solubility.

The pH-dependent solubility characteristics of the active substance may mean that the active substance intended for extended release may be released from the preparation at the low pH value of 1 of the stomach, however, significantly decreases in release at pH values exceeding pH 5.5 in the small intestine due to poor solubility, depending on the dose, when for example administered orally in solid preparations of conventional composition, the active substance is only totally dissolved in the patient's stomach if the liquid present in the stomach has a pH low enough. If the pH in the stomach is elevated (this may be the result of normal physiological variability, illness or co-medication with pharmaceutical compositions that raise the gastric pH), the active substance may not dissolve totally.

The controlled release system of the present invention is preferably useful for such compounds for which the saturation solubility varies by the factor of 5 or more within the pH-range of 1 to 8 (measured in 0.1 n HCl or Mc Ilvaine buffer at room temperature, see Table 1)

TABLE 1

Composition of citric acid/phosphate/(McIlvaine)-buffer

| pH of buffer | citric acid × $H_2O$ | $Na_2HPO_4$ × $2H_2O$ | demineralized $H_2O$ ad |
|---|---|---|---|
| pH 2.2 | 2.076 g | 0.043 g | 100 ml |
| pH 3.0 | 1.687 g | 0.701 g | 100 ml |
| pH 4.0 | 1.303 g | 1.353 g | 100 ml |
| pH 5.0 | 1.029 g | 1.816 g | 100 ml |
| pH 6.0 | 0.786 g | 2.229 g | 100 ml |
| pH 7.0 | 0.399 g | 2.884 g | 100 ml |
| pH 7.8 | 0.097 g | 3.396 g | 100 ml |

Scientific Tables Geigy, Volume Hematology and Human Genetics pg 60 ff, 8$^{th}$ edition, Basle, 1979, 4$^{th}$ reprint 1985

The pharmaceutically active substance to be contained in the second layer includes any medicament which can be administered by oral route. Without being limitative the following illustrative examples are given: agents affecting digestive organs, agents for liver diseases, agents against sexual disorders, analgesics, antiallergics, antiarrhythmics, antibiotics, antipyretics, analgesics and anti-inflammatory agents, antidiabetics, antihistamines, antidotes, antiepileptics, antihypertensives, antihypotensives, anticoagulants, antimycotics, antiphlogistics, antilipaemics, antithrombotic, antitussive and antiemetic agents, anti-tumor agents, autonomic agents, beta receptor blockers, calcium antagonists and ACE inhibitors, agents for the treatment of CNS disorders, affective disorders, sexual disorders, cardiovascular disorders, broncholytics/antiasthmatics, cardiacs, cardiotonics, chemotherapeutics, cholinergics, corticosteroids (internal), dermatics, diuretics, enzyme inhibitors, enzyme preparations and transport proteins, expectorants, geriatrics, gout remedies, flu medicines, hormones and their inhibitors, hypnotics/sedatives, inhibitors of thrombin, local anesthetics, lipid-lowering drugs, muscle relaxants, nutrients, parathyroid hormones/calcium metabolism regulators, psychopharmaceuticals, psychotropic agents, respiratory stimulants, sex hormones and their inhibitors, spasmolytics, sympatholytics, sympathomimetics, tonics and alternatives, vitamins, vasodilators, wound medications, cytostatics and the like.

Preferred active substances are for example ethyl 3-[(2-{[4-(hexyloxycarbonylamino-imino-methyl)-phenylamino]-methyl}-1-methyl-1H-benzimidazole-5-carbonyl)-pyridin-2-yl-amino]-propionate (WO 98/37075), Lefradafiban ((3S, 5S)-5-[[4'-(N-methoxycarbonylamidino)4-biphenylyl]-oxymethyl]-3-[(methoxycarbonyl)methyl]-2-pyrrolidinone; EP 0 483 667), (R)-2-[4-(N-phenylcarbonylamidino)-phenylaminomethyl]-1-methyl-5-[1-(n-propyloxycarbonyl-methylamino)-1-(pyrrolidinocarbonyl)-ethyl]-benzimidazole (WO 01/47896), Telmisartan, DTTX 30 SE, Terbogrel, Bromhexine, Amelubant (4-((3-((4-(1-(4-hydroxyphenyl)-1-methylethyl)phenoxy)methyl)benzyl)oxy)benzenecarboximid-amid-N-ethylcarboxylate; WO 96/02497), Flibanserin (1-[2-(4-(3-trifluoromethyl-phenyl)piperazin-1-yl)ethyl]-2,3-dihydro-1H-benzimidazol-2-one; EP-A-526434;), 4-(4-(2-pyrrolylcarbonyl)-1-piperazinyl)-3-trifluoromethyl-ben-zoylguanidine (WO 00/17176), Pimobendane optionally in form the free base or acid, or in form of one of the pharmacologically acceptable acid addition salts (such as the hydrochlorides, hydrobromides, mesylates, sulphates and phosphates) and/or optionally in form of the hydrates and/or solvates thereof.

In a more preferred embodiment of the present invention the active ingredient is flibanserin, optionally in form the free base, the pharmacologically acceptable acid addition salts and/or optionally in form of the hydrates and/or solvates thereof.

The controlled release system containing flibanserin can be used for the treatment of different diseases. The indication of flibanserin may include all known indications thereof, preferably in the treatment of patients suffering from central nervous system disorders, in particular in affective disorders (e.g. depression like major depressive disorder, childhood depression, dysthymia, seasonal affective disorder, dysthymic disorder and minor depressive disorder; bipolar disorders), anxiety (incl. panic disorder with or without agoraphobia, agoraphobia without history of panic disorder, specific phobia (simple phobia), social phobia (social anxiety disorder), obsessive-compulsive disorder (OCD), post-traumatic stress disorder, acute stress disorder, generalized anxiety disorder and anxiety disorder not otherwise specified), sleep and sexual disorders (e.g. Hyposexual Desire Disorder, sexual aversion disorder, sexual arousal disorder, orgasmic disorder, sexual pain disorders like dyspareunia, vaginismus, noncoital sexual pain disorder; sexual dysfunction due to a general medical condition and substance-induced sexual dysfunction), premenstrual disorders like premenstrual dysphoria, premenstrual syndrome and premenstrual dysphoric disorder; psychosis, schizophrenia (including the disorganized type, the catatonic type, the paranoid type, the undifferentiated type, the residual type of schizophrenia, schizoaffective disorder, schizophreniform disorder, delusional disorder, brief psychotic disorder, shared psychotic disorder, psychotic disorder due to a general medical condition, substance-induced psychotic disorder, and psychotic disorder not otherwise specified), personality disorders, mental organic disorders, mental disorders in childhood, aggressiveness, age associated memory impairment, for neuroprotection, the treatment and/or prevention of neurodegenerative diseases as well as cerebral ischaemia of various origins (e.g. epilepsy, hypoglycaemia, hypoxia, anoxia, brain trauma, brain oedema, amyotropic lateral sclerosis, Huntington's disease, Alzheimer's disease, hypotension, cardiac infarct, brain pressure (elevated intracranial pressure), ischaemic and haemorrhagic stroke (stroke), global cerebral ischaemia during stoppage of the heart, diabetic polyneuropathy, tinnitus, perinatal asphyxia, cardiac hypertrophia (thickening of the heart muscle) and cardiac insufficiency (weakness of the heart muscle); anorexia nervosa (incl. binge-eating/purging type of anorexia nervosa and the restricting type of anorexia nervosa), Attention Deficit Hyperactivity Disorder (ADHD) (incl. ADHD predominantly combined type, ADHD predominantly inattentive type, and ADHD predominantly hyperactive-impulsive type), obesity (incl. exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity and central obesity), urinary incontinence (incl. overactive bladder syndrome, urgency, urge urinary incontinence, stress urinary incontinence, mixed urinary incontinence), chronic pain (incl. neuropathic pain, diabetic neuropathy, post-herpetic neuralgia (PHN), carpal tunnel syndrome (CTS), HIV neuropathy, phantom limb pain, complex regional pain syndrome (CPRS), trigeminal neuralgia/trigeminus neuralgia/tic douloureux, surgical intervention (e.g. post-operative analgesics), diabetic vasculopathy, capillary resistance or diabetic symptoms associated with insulitis, pain associated with angina, pain associated with menstruation, pain associated with cancer, dental pain, headache, migraine, trigeminal neuralgia, temporomandibular joint syndrome, myofascial pain muscular injury, fibromyalgia syndrome, bone and joint pain (osteoarthritis), rheumatoid arthritis, rheumatoid arthritis and edema resulting from trauma associated with burns, sprains or fracture bone pain due to osteoarthritis, osteoporosis, bone metastases or unknown reasons, gout, fibrositis, myofascial pain, thoracic outlet syndromes, upper back pain or lower back pain (wherein the back pain results from systematic, regional, or primary spine disease (radiculopathy), pelvic pain, cardiac chest pain, non-cardiac chest pain, spinal cord injury (SCI)-associated pain, central post-stroke pain, cancer neuropathy, AIDS pain, sickle cell pain and geriatric pain), Valvular Heart Disease (incl. valvular stenosis, valvular regurgitation, atresia of one of the valves, mitral valve prolapse). Preferably, the controlled release system containing flibanserin can be used for the treatment of sexual disorders (e.g. Hyposexual Desire Disorder, sexual aversion disorder, sexual arousal disorder, orgasmic disorder, sexual pain disorders like dyspareunia, vaginismus, noncoital sexual pain disorder; sexual dysfunction due to a general medical condition and substance-induced sexual dysfunction), more preferably Hyposexual Desire Disorder; and premenstrual disorders like premenstrual dysphoria, premenstrual syndrome and premenstrual dysphoric disorder.

Flibanserin is contained in an amount suitable for exhibiting the desired pharmacological activities of each medicament, which are known and varies in accordance with the type of medication. Flibanserin is preferably present in a pharmaceutically effective amount (0.01 mg to 200 mg, preferably from 0.1 to 100 mg or 0.1 to 50 mg), which, however, may depend from a number of factors for example the age and body weight of the patient, and the nature and stage of the disease. This is deemed to be within the capabilities of the skilled man, and the existing literature on the components can be consulted in order to arrive at the optimum dose. The dose range applicable per day is between 0.1 to 400, preferably between 1.0 to 300, more preferably between 2 to 200 mg.

The dosage forms are administered to the patient 1, 2, 3, or 4 times daily. It is preferred that the formulations of the invention are administered either three or fewer times, more preferably once or twice daily consecutively over a period of time.

Preferably, the dose is administered to a patient in the morning and the evening, more preferably once in the morning (25 or 50 mg of flibanserin) and once in the evening (25 or 50 mg of flibanserin), most preferably once in the evening only (50 or 100 mg of flibanserin) consecutively over a period of time.

The pharmaceutically active substance is contained in an amount suitable for exhibiting the desired pharmacological activities of each medicament, which are known and varies in accordance with the kinds of the medicament. The preferred active substance content is, for example, not more than 60%, preferably not more than 50% of the whole controlled release system.

Unless otherwise stated, percentages specified are always percent by weight.

In order to determine the optimum dose of the active substance, various basic conditions have to be taken into consideration such as for example the age and body weight of the patient, the nature and stage of the disease and the potency of the compound. This is deemed to be within the capabilities of the skilled man, and the existing literature on the components can be consulted in order to arrive at the optimum dose.

The active substance layer contains the active substance as well as preferably one or more binders and/or optionally one or more separating agents and/or other excipients. The term "excipients" or "additives" or "adjuvants" as understood in the present invention shall mean any known suitable auxiliary compound which may be used in pharmaceuticals in order to provide one or more functionalities to the controlled release system according to the present invention.

For example suitable binders may be those as described in connection with the core material. Preferably used are cellulose and derivatives thereof such as hydroxypropyl celluloses (e.g. Klucel EF), hydroxypropylmethyl celluloses, methylcelluloses, hydroxyethyl celluloses, carboxymethylcelluloses, cellulose acetate phthalate, polyvinylpyrrolidone (PVP), copolymers of N-vinylpyrrolidone, gelatin, shellac, hydroxypropyl methylcellulose phthalate, for example HP 55® or HP 50®, polymers and copolymers of acrylic and methacrylic acid and the esters thereof, or combinations of these polymers such as polymethacrylates, starches and derivatives thereof, sugars, vinyl acetate or combinations of these polymers and derivatives thereof. Most preferably used are hydroxypropyl cellulose or copolymers of N-vinylpyrrolidone and vinyl acetate.

The addition of suitable separating agents such as e.g. talc, magnesium stearate or silicic acid serves to prevent the particles from aggregating during the manufacturing process.

Beside binding agents and separating agents, the second layer may also incorporate various other conventional additives, excipients, carriers, technological adjuvants such as fillers, diluents, lubricants, glidants, agents to improve flowability, pore formers, anti-adherents, anti-tacking agents, flavors, preservatives, sweetening agents, disintegrants, dyes and the like. The above listing is not intended to be of limitative character, other conventional additives known in the art can also be included.

As further excipients which may be present the following non limitative groups are given
  preservatives, preferably antimicrobial preservatives such as benzalkonium chloride, benzoic acid, methyl parahydroxybenzoate, propyl parahydroxybenzoate, sodium benzoate, and sorbic acid;
  sweetening agents such as acesulfame potassium, alitame, aspartame, compressible sugar, confectioner's sugar, dextrose, erythritol, fructose, glycerin, inulin, isomalt, lactitol, liquid glucose, maltitol, maltose, mannitol, neospheridin dihydrochalcone, polydextrose, saccharin, saccharin sodium, sodium cyclamate, sorbitol, sucralose, sucrose, thaumatin, trehalose, xylitol; and
  disintegrants such as alginic acid and salts thereof including calcium, sodium, magnesium, carboxymethylcellulose calcium, carboxymethylcellulose sodium, powdered cellulose, chitosan, colloidal silicon dioxide, crospovidone, croscarmellose sodium, docusate sodium, guar gum, hydroxypropyl cellulose, particularly low-substituted hydroxypropyl cellulose, hydroxypropyl starch, magnesium aluminum silicate, methylcellulose, micocrystalline cellulose, polacrilin potassium, povidone, sodium starch glycolate, starch, particularly pregelatinized starch, and corn starch.

Suitable fillers may be selected from, for example, lactose, in particular lactose monohydrate, talc, sunflower oil, tragacanth, starches and derivatives such as pregelatinized starch or sterilizable maize, alginate such as ammonium alginate, sodium alginate, sodium chloride, calcium carbonate, dibasic calcium phosphate, calcium sulphate, dicalcium or tricalcium phosphate, magnesium carbonate, magnesium oxide, cellulose and derivatives, such as microcrystalline or silicified microcrystalline cellulose, cellulose acetate, ethylcellulose, sugars and derivatives such as confectioner's sugar, fructose, sucrose, dextrate, dextrin, sulfobutylether β-cyclodextrin, dextrose, polydextrose, trehalose, maltose, maltitol, mannitol, maltodextrin, sorbitol, inulin, xylitol, erythritol, fumaric acid, glyceryl palmitostearate, tablettose, hydrogenated vegetable oils, isomalt, kaolin, lactitol, triglycerides, particularly medium-chain triglycerides, polymethacrylate, and simethicone as well as derivatives or mixtures thereof.

It is a matter of course that an additive may have more than one functionality so that they may be categorized among more than one type of additive. For example corn starch or pregelatinized starch may impart several functions at the same time such as swelling polymer, filler, glidant, and the like. However, the skilled person knows the several functions and is able to select the additive according to the intended use thereof. The selection of additives depends from a variety of factors such as the active substance used, the desired application field, dose form and the like. Such requirements are known by the skilled person.

The application quantity of the second layer based on the specific surface area of the starting core is in the range from 0.1 to 20 mg/cm$^2$, preferably 1.0 to 18 mg/cm$^2$, more preferably 5.0 to 15 mg/cm$^2$, particularly 7.0 to 13 mg/cm$^2$, more particularly 8.0 to 12.0 mg/cm$^2$.

According to an alternative embodiment of the present invention it is also possible to provide an optional insulating layer applied on the second layer containing active substance. Said insulating layer may be provided additionally or alternatively to the first insulating layer b) described above. The second insulating layer may have the same structure and composition as already described above for the first insulating layer.

The application quantity of the optional (second) insulating layer based on the specific surface area of the starting core is in the range from 0.05 to 5.0 mg/cm$^2$, preferably 0.1 to 3.0 mg/cm$^2$, more preferably 0.15 to 2.5 mg/cm$^2$, particularly 0.2 to 2.0 mg/cm$^2$ and more particularly 0.2 to 1.5 mg/cm$^2$.

e) Third Layer

The third layer which may be a controlled release outer coating layer comprises or consists of one or more polymers having anionic or no ionic groups. This polymer is not limited according to the present invention. Any type of pharmaceutically acceptable polymer having anionic or no ionic groups may be used.

The polymer having anionic or no ionic groups contained in the third layer may be selected from polymers and/or copolymers comprising acrylic and/or methacrylic acids or derivatives thereof (having no cationic groups such as quaternary ammonium groups, particularly no trimethylammonium-ethyl groups), alkylcelluloses and derivatives thereof, such as ethylcelluloses, hydroxyalkyl celluloses and derivatives thereof, hydroxyalkyl alkylcelluloses, like hydroxypropyl methylcellulose (e.g. Hypromellose E5), and derivatives thereof such as hydroxypropylmethyl cellulose phthalates (e.g. HP 55® or HP 50®) hydroxypropyl methylcellulose acetate succinate, cellulose acetates and derivatives thereof such as cellulose acetate phthalate, cellulose acetate trimellitate, polyvinyl acetates and derivatives thereof such as polyvinyl acetate phthalate, shellac, derivatives and mixtures thereof. Particularly preferred polymers are ethylcelluloses in different grades such as varying ethoxyl content and molecular weight, e.g. in form of organic-based polymeric solutions or aqueous-based polymeric dispersions thereof, for example, ethylcellulose N10, N20 or N45, Aquacoat® ECD, Surelease®, Chitosan, Shellac, and Zein.

Also preferably used are, for example, poly(ethyl acrylate, methyl methacrylate) 2:1 (Eudragit® NE), e.g. in form of aqueous-based polymeric dispersions thereof, for example Eudragit® NE 30D, Kollicoat® EMM 30D; poly(methacrylic acid, ethylacrylate) 1:1 (Eudragit® L 100-55 or Eudragit® L 30D-55); poly(methacrylic acid, methyl methacrylate) 1:1 (Eudragit® L 100); poly(methacrylic acid, methyl methacrylate) 1:2 (Eudragit® S); hydroxypropyl methylcellulose acetate succinate, for example organic-based polymeric solutions or aqueous-based polymeric dispersions thereof; hydroxypropyl methylcellulose phthalate, for example organic-based polymeric solutions or aqueous-based polymeric dispersions thereof; cellulose acetate trimellitate, for example organic-based polymeric solutions thereof; hydroxypropyl methylcellulose phthalate, for example HP 55® or HP 50®, cellulose acetate phthalate, for example organic-based polymeric solutions or aqueous-based polymeric dispersions thereof such as Aquacoat® CPD; polyvinyl acetate phthalate, for example aqueous-based polymeric dispersions thereof such as Sureteric® and shellac, for example organic-based polymeric solutions or aqueous-based polymeric dispersions thereof.

Furthermore preferably mentioned are cellulose acetate and derivatives thereof such as organic-based polymeric solutions thereof and/or polyvinyl acetate and derivatives thereof such as aqueous-based polymeric dispersions thereof, for example Kollicoat® SR 30D.

The mentioned polymers may be used alone or in combination of two or more polymers.

Eudragit® RS, or Eudragit RL® having cationic groups are excluded to be present in the third layer.

According to a preferred embodiment the polymer(s) present in the third layer is (are) identical or different from the polymer(s) present in the first layer. For example the polymer(s) of the first and second layer may be the same.

Preferably one or more plasticizers are present in the third layer. The plasticizers may be selected from the plasticizers already described in connection with the optional insulating layer. More preferably the plasticizer is selected from the group consisting of acetylated monoglyceride, acetyltributyl citrate, acetyltriethyl citrate, dibutyl phthalate, dibutyl sebacate, diethyl phthalate, dimethyl phthalate, tributyl citrate, triethyl citrate, polyethylene glycols (all types at different molecular weights of PEGs), and propylene glycol.

Preferably one or more pore formers are present in the third layer. Possible pore formers are methylcellulose, hydroxypropyl methylcelluloses (e.g. hypromellose E5), hydroxypropyl cellulose, hydroxyethyl cellulose, Eudragit® E (Poly (butyl methacrylate, (2-dimethylaminoethyl)methacrylate, methyl methacrylate) 1:2:1), alginic acid and salts thereof including calcium, potassium, propylene glycol, and sodium alginate, gelatin, povidone (e.g. Kollidon 17), and polyvinyl alcohol.

Other additives may be used such as lubricants, antiadherents, anticaking agents, fillers and the like.

In a preferred embodiment of the present invention the third layer comprises a polymer selected from the group consisting of Eudragit® NE, ethylcellulose (N10, N20 or N45) Kollicoat® EMM 30D; poly(methacrylic acid, ethylacrylate) 1:1 (Eudragit® L 100-55 or Eudragit® L 30D-55); poly(methacrylic acid, methyl methacrylate) 1:1 (Eudragit® L 100); poly(methacrylic acid, methyl methacrylate) 1:2 (Eudragit® S); and/or mixtures thereof in an amount of 0.2 to 3.0 mg/cm$^2$ (calculated as dry matter of the polymer or polymer mixture), a pore former selected from the group consisting of methylcellulose, hydroxypropyl methylcelluloses, hydroxypropyl cellulose, hydroxyethyl cellulose, povidone (e.g. Kollidon 17) and Eudragit® E (Poly(butyl methacrylate, (2-dimethylaminoethyl)methacrylate, methyl methacrylate) 1:2:1) in an amount of 30 to 300% (w/w, based on the dry polymer/polymer-mixture matter of the layer), a plasticizer from the group consisting of acetyltributyl citrate, acetyltriethyl citrate, dibutyl phthalate, dibutyl sebacate, diethyl phthalate, dimethyl phthalate, glycerine triacetate (triacetin), tributyl citrate, triethyl citrate, polyethylenen glycols in an amount 10 to 30% (w/w, based on the dry polymer/polymer-mixture matter of the layer) and optionally an anti-tacking agent, anti-sticking agent or glidant from the group consisting of glycerol monostearate, talc or polyethylene glycol in an amount of 0 to 20% (w/w, based on the dry polymer/polymer-mixture matter of the layer).

In a further preferred embodiment of the present invention the third layer comprises a polymer selected from the group consisting of Eudragit® NE, ethylcellulose (N10, N20 or N45) Kollicoat®EMM 30D; poly(methacrylic acid, ethylacrylate) 1:1 (Eudragit® L 100-55 or Eudragit® L 30D-55); poly(methacrylic acid, methyl methacrylate) 1:1 (Eudragit® L 100); poly(methacrylic acid, methyl methacrylate) 1:2 (Eudragit® S); and/or mixtures thereof in an amount of 0.2 to 3.0 mg/cm$^2$ (calculated as dry matter of the polymer or polymer mixture), a plasticizer from the group consisting of acetyltributyl citrate, acetyltriethyl citrate, dibutyl phthalate, dibutyl sebacate, diethyl phthalate, dimethyl phthalate, glycerine triacetate (triacetin), tributyl citrate, triethyl citrate, polyethylenen glycols in an amount 10 to 30% (w/w, based on the dry polymer/polymer-mixture matter of the layer) and optionally an anti-tacking agent, anti-sticking agent or glidant from the group consisting of glycerol monostearate, talc or polyethylene glycol in an amount of 0 to 20% (w/w, based on the dry polymer/polymer-mixture matter of the layer).

Preferably, the polymers used in the third layer are selected from the group consisting of selected from the group consisting of ethylcellulose, hydroxypropyl methylcellulose phthalate, and poly(methacrylic acid, ethylacrylate) 1:1 (Eudragit® L 100-55 or Eudragit® L 30D-55); and/or mixtures thereof, more preferably from the group consisting of ethylcellulose and poly(methacrylic acid, ethylacrylate) 1:1 (Eudragit® L 100-55 or Eudragit® L 30D-55); and/or mixtures thereof.

The application quantity of the third layer based on the specific surface area of the starting core is in the range from 0.1 to 15 mg/cm$^2$, preferably 0.2 to 12 mg/cm$^2$, more preferably 0.5 to 10 mg/cm$^2$, particularly 0.7 to 8.0 mg/cm$^2$, more particularly 0.8 to 5.0 mg/cm$^2$.

f) Optional Fourth Layer

The optional fourth layer may preferably be an outer coating layer. Said optional outermost layer, which may serve to reduce any increased abrasion during packing, e.g. into capsules and/or to increase the shelf life and/or as further diffusion barrier, comprises or consists of one or more pharmaceutically conventional film-forming agents and optionally excipients, particularly preferred are plasticizers and pigments.

Suitable film-forming agents to reduce increased abrasion and/or can serve as further diffusion barrier include for example ammonium alginate, chitosan, chlorpheniramine maleate, copovidone, phthalate such as dibutyl phthalate, diethyl phthalate, dimethyl phthalate, cellulose acetate phthalate, polyvinyl acetate phthalate, dibutyl sebacate, ethyl lactate, alkylcelluloses and derivatives thereof such as ethylcelluloses, methylcelluloses, gelatin, hydroxyalkyl celluloses and derivatives thereof such as hydroxyethyl cellulose, hydroxypropyl cellulose, hydroxyalkyl alkylcellulose and derivatives thereof such as hypromelloses (hydroxypropyl methylcellulose), hydroxypropyl methylcellulose acetate succinate, hydroxypropyl methylcellulose phthalate, cellulose acetate trimellitate, cellulose acetate phthalate, maltodextrin, calcium carbonate, polydextrose, polyethylene glycols (all types at different molecular weights of PEGs), polyethylene oxide, polymers and copolymers of acrylic and methacrylic acid and the esters thereof, or combinations of these polymers such as polymethacrylates, poly(methylvinyl ether/maleic anhydride), polyvinyl acetate phthalate, triethyl citrate, vanillin, shellac, Zein, as well as derivatives and mixtures thereof.

Particularly preferred film-forming agents are hydroxypropyl cellulose, hydroxypropyl methylcellulose, methylcelluloses, polymers and copolymers of acrylic and methacrylic acid and the esters thereof, or combinations of these polymers, for example used in form of organic-based polymeric solutions or aqueous-based polymeric dispersions thereof. Also preferred polymers are poly(methacrylic acid, ethylacrylate) 1:1 (Eudragit® L 100-55 or Eudragit® L 30D-55); poly(methacrylic acid, methyl methacrylate) 1:1 (Eudragit® L 100); poly(methacrylic acid, methyl methacrylate) 1:2 (Eudragit® S); hydroxypropyl methylcellulose acetate succinate, for example organic-based polymeric solutions or aqueous-based polymeric dispersions thereof; hydroxypropyl methylcellulose phthalate, for example organic-based polymeric solutions or aqueous-based polymeric dispersions thereof; cellulose acetate trimellitate, for example organic-based polymeric solutions thereof; cellulose acetate phthalate, for example organic-based polymeric solutions or aqueous-based polymeric dispersions thereof such as Aquacoate® CPD; polyvinyl acetate phthalate, for example aqueous-based polymeric dispersions thereof such as Sureteric® and shellac, for example organic-based polymeric solutions or aqueous-based polymeric dispersions thereof.

The compounds are partly commercially available in form of organic-based solutions or dispersions or aqueous-based solutions or dispersions. It is also possible to produce such solutions or dispersions. The expressions "organic-based" and "aqueous-based" systems shall be understood to be directed to the solvents or dispergants mainly present in the liquid system to be used. Also mixtures of solvents and/or dispergants may be included.

Suitable plasticizers are already described, preferably are used inter alia triethyl citrate, tributyl citrate, triacetin or polyethyleneglycols. Preferred pigments used may be e.g. titanium dioxide or iron oxide pigments. Also fillers may be contained, possible fillers are described above. Other known additives may be present, if desired.

It is particularly preferred if the optional fourth layer is omitted in the controlled release system according to the present invention. However, the controlled release system of the invention may comprise this fourth layer as a type of non-functional coating in case intended as an abrasion protective layer or a functional coating in case the layer is intended as a diffusion barrier. The term "non-functional" in the present context means having no substantial effect on release properties of the controlled release system, and the coating serves another useful purpose. For example, such a coating can impart a distinctive appearance to the dosage form, provide protection against attrition during packaging and transportation, improve ease of swallowing, and/or have other benefits. A non-functional coating should be applied in an amount sufficient to provide complete coverage of the controlled release system. Typically an amount of about 1% to about 10%, more typically an amount of about 2% to about 5%, by weight of the controlled release system as a whole, is suitable.

In a preferred embodiment of the present invention where the fourth layer is intended to protect the drug product from abrasion the layer comprises a polymer selected from the group consisting of hydroxypropyl cellulose, hydroxypropyl methylcellulose, methylcelluloses, Eudragit® E (Poly(butyl methacrylate, (2-dimethylaminoethyl)methacrylate, methyl methacrylate) 1:2:1); and/or mixtures thereof in an amount of 0.2 to 1.5 mg/cm$^2$ (calculated as dry matter of the polymer or polymer mixture), a plasticizer from the group consisting of acetyltributyl citrate, acetyltriethyl citrate, dibutyl phthalate, dibutyl sebacate, diethyl phthalate, dimethyl phthalate, glycerine triacetate (triacetin), tributyl citrate, triethyl citrate, polyethylenen glycols in an amount 10 to 30% (w/w, based on the dry polymer/polymer-mixture matter of the layer) and an anti-tacking agent, anti-sticking agent or glidant from the group consisting of glycerol monostearate, talc or polyethylene glycol in an amount of 0 to 20% (w/w, based on the dry polymer/polymer-mixture matter of the layer).

In another preferred embodiment of the present invention where the fourth layer is intended as an additional diffusion barrier the layer comprises a polymer selected from the group consisting of Eudragit® NE, ethylcellulose (N10, N20 or N45), Kollicoat® EMM 30D, poly(methacrylic acid, ethylacrylate) 1:1 (Eudragit® L 100-55 or Eudragit® L 30D-55); poly(methacrylic acid, methyl methacrylate) 1:1 (Eudragit® L 100); poly(methacrylic acid, methyl methacrylate) 1:2 (Eudragit® S); and/or mixtures thereof in an amount of 0.5 to 2.5 mg/cm$^2$ (calculated as dry matter of the polymer or polymer mixture). Additionally the fourth layer comprises a plasticizer from the group consisting of acetyltributyl citrate, acetyltriethyl citrate, dibutyl phthalate, dibutyl sebacate, diethyl phthalate, dimethyl phthalate, glycerine triacetate (triacetin), tributyl citrate, triethyl citrate, polyethylenen glycols in an amount 10 to 30% (w/w, based on the dry polymer/polymer-mixture matter of the layer) and optionally an anti-tacking agent, anti-sticking agent or glidant from the group consisting of glycerol monostearate, talc or polyethylene glycol in an amount of 0 to 20% (w/w, based on the dry polymer/polymer-mixture matter of the layer).

In a further preferred embodiment of the present invention where the fourth layer is intended as an additional diffusion barrier the layer comprises a polymer selected from the group consisting of Eudragit® NE, ethylcellulose (N10, N20 or N45), Kollicoat® EMM 30D; poly(methacrylic acid, ethylacrylate) 1:1 (Eudragit® L 100-55 or Eudragit® L 30D-55); poly(methacrylic acid, methyl methacrylate) 1:1 (Eudragit® L 100); poly(methacrylic acid, methyl methacrylate) 1:2 (Eudragit® S); and/or mixtures thereof in an amount of 1.0 to 5.0 mg/cm$^2$ (calculated as dry matter of the polymer or polymer mixture), a pore former selected from the group consisting of methylcellulose, hydroxypropyl methylcelluloses, hydroxypropyl cellulose, hydroxyethyl cellulose, povidone (e.g. Kollidon 17) and Eudragit® E (Poly(butyl methacrylate, (2-dimethylaminoethyl)methacrylate, methyl methacrylate) 1:2:1) in an amount of 30 to 300% (w/w, based on the dry polymer/polymer-mixture matter of the layer), a plasticizer from the group consisting of acetyltributyl citrate, acetyltriethyl citrate, dibutyl phthalate, dibutyl sebacate, diethyl phthalate, dimethyl phthalate, glycerine triacetate (triacetin), tributyl citrate, triethyl citrate, polyethylenen glycols in an amount 10 to 30% (w/w, based on the dry polymer/polymer-mixture matter of the layer) and optionally an anti-tacking agent, anti-sticking agent or glidant from the group consisting of glycerol monostearate, talc or polyethylene glycol in an amount of 0 to 20% (w/w, based on the dry polymer/polymer-mixture matter of the layer).

Preferably, if the fourth layer is intended as an additional diffusion barrier, the layer comprises a polymer is selected from the group consisting of ethylcellulose, hydroxypropyl methylcellulose phthalate, and poly(methacrylic acid, ethylacrylate) 1:1 (Eudragit® L 100-55 or Eudragit® L 30D-55); and/or mixtures thereof, more preferably selected from the group consisting of hydroxypropyl methylcellulose phthalate, and poly(methacrylic acid, ethylacrylate) 1:1 (Eudragit® L 100-55 or Eudragit® L 30D-55); and/or mixtures thereof and most preferably the polymer is poly(methacrylic acid, ethylacrylate) 1:1 (Eudragit® L 100-55 or Eudragit® L 30D-55).

The application quantity of the fourth layer based on the specific surface area of the starting core is in the range from 0.1 to 15 mg/cm$^2$, preferably 0.2 to 12 mg/cm$^2$, more preferably 0.5 to 10 mg/cm$^2$, particularly 0.7 to 8.0 mg/cm$^2$, more particularly 0.8 to 5.0 mg/cm$^2$.

According to a preferred embodiment, the controlled release system of the present invention is characterized in that the application quantities for the layers present, based on the specific surface area of the starting core, are as follows:
optional (first) insulating layer:
in the range from 0.05 to 5.0 mg/cm$^2$;
first layer:
in the range from 0.1 to 15 mg/cm$^2$;
second layer:
in the range from 0.1 to 20 mg/cm$^2$;
third layer:
in the range from 0.1 to 15 mg/cm$^2$, and
optional fourth layer:
in the range from 0.1 to 15 mg/cm$^2$.

According to a more preferred embodiment, the controlled release system of the present invention is characterized in that the application quantities for the layers present, based on the specific surface area of the starting core, are as follows:
optional (first) insulating layer:
in the range from 0.1 mg/cm$^2$, to 3.0 mg/cm$^2$;
first layer:
in the range from 0.5 to 12 mg/cm$^2$;
second layer:
in the range from 1 to 18 mg/cm$^2$;
third layer:
in the range from 0.2 to 12 mg/cm$^2$, and
optional fourth layer:
in the range from 0.2 to 12 mg/cm$^2$.

According to a even more preferred embodiment, the controlled release system of the present invention is characterized in that the application quantities for the layers present, based on the specific surface area of the starting core, are as follows:
optional (first) insulating layer:
in the range from 0.15 mg/cm$^2$, to 2.5 mg/cm$^2$;
first layer:
in the range from 1 to 10 mg/cm$^2$;
second layer:
in the range from 5 to 15 mg/cm$^2$;
third layer:
in the range from 0.5 to 10 mg/cm$^2$, and
optional fourth layer:
in the range from 0.5 to 10 mg/cm$^2$.

According to a even more preferred embodiment, the controlled release system of the present invention is characterized in that the application quantities for the layers present, based on the specific surface area of the starting core, are as follows:

optional (first) insulating layer:
in the range from 0.2 mg/cm², to 2.0 mg/cm²;
first layer:
in the range from 1.5 to 8 mg/cm²;
second layer:
in the range from 7 to 13 mg/cm²;
third layer:
in the range from 0.7 to 8 mg/cm², and
optional fourth layer:
in the range from 0.7 to 8 mg/cm².

According to a most preferred embodiment, the controlled release system of the present invention is characterized in that the application quantities for the layers present, based on the specific surface area of the starting core, are as follows:

optional (first) insulating layer:
in the range from 0.2 mg/cm², to 1.5 mg/cm²;
first layer:
in the range from 2 to 6 mg/cm²;
second layer:
in the range from 8 to 12 mg/cm²;
third layer:
in the range from 0.8 to 5 mg/cm², and
optional fourth layer:
in the range from 0.8 to 5 mg/cm².

According to a further preferred embodiment, the controlled release system of the present invention is characterized in that the application quantities for the layers present, based on the specific surface area of the starting core, are as follows:

optional (first) insulating layer:
in the range from 0.05 to 30.0 mg/cm²;
first layer:
in the range from 0.1 to 15 mg/cm²;
second layer:
in the range from 0.1 to 20 mg/cm²;
third layer:
in the range from 0.1 to 15 mg/cm², and
optional fourth layer:
in the range from 0.1 to 15 mg/cm².

According to a more preferred embodiment, the controlled release system of the present invention is characterized in that the application quantities for the layers present, based on the specific surface area of the starting core, are as follows:

optional (first) insulating layer:
in the range from 0.1 mg/cm², to 20.0 mg/cm²;
first layer:
in the range from 0.5 to 12 mg/cm²;
second layer:
in the range from 1 to 18 mg/cm²;
third layer:
in the range from 0.2 to 12 mg/cm², and
optional fourth layer:
in the range from 0.2 to 12 mg/cm².

According to a even more preferred embodiment, the controlled release system of the present invention is characterized in that the application quantities for the layers present, based on the specific surface area of the starting core, are as follows:

optional (first) insulating layer:
in the range from 0.15 mg/cm², to 15 mg/cm²;
first layer:
in the range from 1 to 10 mg/cm²;
second layer:
in the range from 5 to 15 mg/cm²;
third layer:
in the range from 0.5 to 10 mg/cm², and
optional fourth layer:
in the range from 0.5 to 10 mg/cm².

According to a even more preferred embodiment, the controlled release system of the present invention is characterized in that the application quantities for the layers present, based on the specific surface area of the starting core, are as follows:

optional (first) insulating layer:
in the range from 0.2 mg/cm², to 12 mg/cm²;
first layer:
in the range from 1.5 to 8 mg/cm²;
second layer:
in the range from 7 to 13 mg/cm²;
third layer:
in the range from 0.7 to 8 mg/cm², and
optional fourth layer:
in the range from 0.7 to 8 mg/cm².

According to a most preferred embodiment, the controlled release system of the present invention is characterized in that the application quantities for the layers present, based on the specific surface area of the starting core, are as follows:

optional (first) insulating layer:
in the range from 0.2 mg/cm², to 10 mg/cm²;
first layer:
in the range from 2 to 6 mg/cm²;
second layer:
in the range from 8 to 12 mg/cm²;
third layer:
in the range from 0.8 to 5 mg/cm², and
optional fourth layer:
in the range from 0.8 to 5 mg/cm².

In a further preferred embodiment, the layers of the controlled release systems having the above described application quantities comprises, preferably consists of:

optional (first) insulating layer: 48 to 50% (w/w) hydroxypropyl methylcellulose (e.g. Pharmacoat 603), 48 to 50% (w/w) talc and 0.1 to 1.5% of anti-foaming agent (e.g. Dimeticon 350) applied in the range from 0.2 mg/cm² to 1.5 mg/cm², based on the specific surface area of the starting core;

first layer: 82 to 84% (w/w) ethylcellulose (e.g. ethylcellulose N10) and 16 to 18% (w/w) triethyl citrate applied in the range from 2 mg/cm² to 6 mg/cm², based on the specific surface area of the starting core;

second layer: 13.5-15.5% (w/w) hydroxylpropyl cellulose (e.g. Klucel EF), 72-75% (w/w) active ingredient (e.g. Flibanserin) and 11-13% (w/w) talc applied in the range from 8 mg/cm² to 12 mg/cm², based on the specific surface area of the starting core;

third layer: 46-48.5% (w/w) ethylcellulose (e.g. ethylcellulose N10), 46-48.5% (w/w) hydroxypropyl methylcellulose (e.g. hypromellose E5) and 3-5.5% (w/w) triethyl citrate applied in the range from 0.8 mg/cm² to 1.5 mg/cm², based on the specific surface area of the starting core, fourth layer: 86-88% (w/w) Eudragit® L 100-55, 8-10% (w/w) talc and 3-5% (w/w) triethyl citrate applied in the range from 0.8 mg/cm² to 5 mg/cm², based on the specific surface area of the starting core.

In a further preferred embodiment, the layers of the controlled release systems having the above described application quantities comprises, preferably consists of:
- optional (first) insulating layer: 48 to 50% (w/w) hydroxypropyl methylcellulose (e.g. Pharmacoat 603), 48 to 50% (w/w) talc and 0.1 to 1.5% of anti-foaming agent (e.g. Dimeticon 350) applied in the range from 0.2 mg/cm$^2$ to 1.5 mg/cm$^2$, based on the specific surface area of the starting core;
- first layer: 82 to 84% (w/w) ethylcellulose (e.g. ethylcellulose N10) and 16 to 18% (w/w) triethyl citrate applied in the range from 2 mg/cm$^2$ to 6 mg/cm$^2$, based on the specific surface area of the starting core;
- second layer: 13.5-15.5% (w/w) hydroxypropyl cellulose (e.g. Klucel EF), 72-75% (w/w) active ingredient (e.g. Flibanserin) and 11-13% (w/w) talc applied in the range from 8 mg/cm$^2$ to 12 mg/cm$^2$, based on the specific surface area of the starting core;
- second insulating layer: 100% (w/w) hydroxypropyl methylcellulose (e.g. hypromellose E5), applied in the range from 0.2 mg/cm$^2$ to 1.5 mg/cm$^2$, based on the specific surface area of the starting core,
- third layer: 86-88% (w/w) Eudragit® L 100-55, 8-10% (w/w) talc and 3-5% (w/w) triethyl citrate applied in the range from 0.8 mg/cm$^2$ to 5.0 mg/cm$^2$, based on the specific surface area of the starting core.

In a further preferred embodiment, the layers of the controlled release systems having the above described application quantities comprises, preferably consists of:
- optional (first) insulating layer: 48 to 50% (w/w) hydroxypropyl methylcellulose (e.g. Pharmacoat 603), 48 to 50% (w/w) talc and 0.1 to 1.5% of anti-foaming agent (e.g. Dimeticon 350) applied in the range from 0.2 mg/cm$^2$ to 1.5 mg/cm$^2$, based on the specific surface area of the starting core;
- first layer: 82 to 84% (w/w) ethylcellulose (e.g. ethylcellulose N10) and 16 to 18% (w/w) triethyl citrate applied in the range from 2 mg/cm$^2$ to 6 mg/cm$^2$, based on the specific surface area of the starting core;
- second layer: 13.5-15.5% (w/w) hydroxypropyl cellulose (e.g. Klucel EF), 72-75% (w/w) active ingredient (e.g. Flibanserin) and 11-13% (w/w) talc applied in the range from 8 mg/cm$^2$ to 12 mg/cm$^2$, based on the specific surface area of the starting core;
- third layer: 46-48.5% (w/w) ethylcellulose (e.g. ethylcellulose N10), 46-48.5% (w/w) hydroxypropyl methylcellulose (e.g. hypromellose E5) and 3-5.5% (w/w) triethyl citrate applied in the range from 0.8 mg/cm$^2$ to 1.5 mg/cm$^2$, based on the specific surface area of the starting core,
- fourth layer: 70-72% (w/w) Eudragit® L 100-55, 15-20% (w/w) hydroxypropyl methylcellulose (e.g. hypromellose E5), 8-10% (w/w) talc and 3-5% (w/w) triethyl citrate applied in the range from 0.8 mg/cm$^2$ to 5 mg/cm$^2$, based on the specific surface area of the starting core.

In a further preferred embodiment, the layers of the controlled release systems having the above described application quantities comprises, preferably consists of:
- optional (first) insulating layer: 48 to 50% (w/w) hydroxypropyl methylcellulose (e.g. Pharmacoat 603), 48 to 50% (w/w) talc and 0.1 to 1.5% of anti-foaming agent (e.g. Dimeticon 350) applied in the range from 0.2 mg/cm$^2$ to 1.5 mg/cm$^2$, based on the specific surface area of the starting core;
- first layer: 82 to 84% (w/w) ethylcellulose (e.g. ethylcellulose N10) and 16 to 18% (w/w) triethyl citrate applied in the range from 2 mg/cm$^2$ to 6 mg/cm$^2$, based on the specific surface area of the starting core;
- second layer: 13.5-15.5% (w/w) hydroxypropyl cellulose (e.g. Klucel EF), 72-75% (w/w) active ingredient (e.g. Flibanserin) and 11-13% (w/w) talc applied in the range from 8 mg/cm$^2$ to 12 mg/cm$^2$, based on the specific surface area of the starting core;
- second insulating layer: 100% (w/w) hydroxypropyl methylcellulose (e.g. hypromellose E5), applied in the range from 0.2 mg/cm$^2$ to 1.5 mg/cm$^2$, based on the specific surface area of the starting core,
- third layer: 70-72% (w/w) Eudragit® L 100-55, 15-20% (w/w) hydroxypropyl methylcellulose (e.g. hypromellose E5), 8-10% (w/w) talc and 3-5% (w/w) triethyl citrate applied in the range from 0.8 mg/cm$^2$ to 5 mg/cm$^2$, based on the specific surface area of the starting core.

In a further preferred embodiment, the layers of the controlled release systems having the above described application quantities comprises, preferably consists of:
- optional (first) insulating layer: 48 to 50% (w/w) hydroxypropyl methylcellulose (e.g. Pharmacoat 603), 48 to 50% (w/w) talc and 0.1 to 1.5% of anti-foaming agent (e.g. Dimeticon 350) applied in the range from 0.2 mg/cm$^2$ to 1.5 mg/cm$^2$, based on the specific surface area of the starting core;
- first layer: 82 to 84% (w/w) ethylcellulose (e.g. ethylcellulose N10) and 16 to 18% (w/w) triethyl citrate applied in the range from 2 mg/cm$^2$ to 6 mg/cm$^2$, based on the specific surface area of the starting core;
- second layer: 13.5-15.5% (w/w) hydroxypropyl cellulose (e.g. Klucel EF), 72-75% (w/w) active ingredient (e.g. Flibanserin) and 11-13% (w/w) talc applied in the range from 8 mg/cm$^2$ to 12 mg/cm$^2$, based on the specific surface area of the starting core;
- third layer: 46-48.5% (w/w) ethylcellulose (e.g. ethylcellulose N10), 46-48.5% (w/w) hydroxypropyl cellulose (e.g. Klucel EF) and 3-5.5% (w/w) triethyl citrate applied in the range from 0.8 mg/cm$^2$ to 1.5 mg/cm$^2$, based on the specific surface area of the starting core,
- fourth layer: 70-72% (w/w) Eudragit® L 100-55, 15-20% (w/w) hydroxypropyl cellulose (e.g. Klucel EF), 8-10% (w/w) talc and 3-5% (w/w) triethyl citrate applied in the range from 0.8 mg/cm$^2$ to 5 mg/cm$^2$, based on the specific surface area of the starting core.

In a further preferred embodiment, the layers of the controlled release systems having the above described application quantities comprises, preferably consists of:
- optional (first) insulating layer: 48 to 50% (w/w) hydroxypropyl methylcellulose (e.g. Pharmacoat 603), 48 to 50% (w/w) talc and 0.1 to 1.5% of anti-foaming agent (e.g. Dimeticon 350) applied in the range from 0.2 mg/cm$^2$ to 1.5 mg/cm$^2$, based on the specific surface area of the starting core;
- first layer: 82 to 84% (w/w) ethylcellulose (e.g. ethylcellulose N10) and 16 to 18% (w/w) triethyl citrate applied in the range from 2 mg/cm$^2$ to 6 mg/cm$^2$, based on the specific surface area of the starting core;
- second layer: 13.5-15.5% (w/w) hydroxypropyl cellulose (e.g. Klucel EF), 72-75% (w/w) active ingredient (e.g. Flibanserin) and 11-13% (w/w) talc applied in the range from 8 mg/cm$^2$ to 12 mg/cm$^2$, based on the specific surface area of the starting core;
- second insulating layer: 100% (w/w) hydroxypropyl methylcellulose (e.g. hypromellose E5), applied in the range from 0.2 mg/cm$^2$ to 1.5 mg/cm$^2$, based on the specific surface area of the starting core, third layer: 70-72% (w/w) Eudragit® L 100-55, 15-20% (w/w) hydroxypropyl cellulose (e.g. Klucel EF), 8-10% (w/w) talc and 3-5% (w/w) triethyl citrate applied in the range from 0.8 mg/cm$^2$ to 5 mg/cm$^2$, based on the specific surface area of the starting core.

In a further preferred embodiment, the layers of the controlled release systems having the above described application quantities comprises, preferably consists of:
- optional (first) insulating layer: 95 to 100% (w/w) hydroxypropyl methylcellulose (e.g. hypromellose E5) and 0 to 5% (w/w) applied in the range from 0.2 mg/cm$^2$ to 10.0 mg/cm$^2$, based on the specific surface area of the starting core;
- first layer: 62 to 86% (w/w) Eudragit RS, 5 to 20% (w/w) triethyl citrate, 5 to 10% glycerol monostearate and 4 to 8% sodium sulphate applied in the range from 2 mg/cm$^2$ to 6 mg/cm$^2$, based on the specific surface area of the starting core;
- second layer: 13.5-15.5% (w/w) hydroxylpropyl cellulose (e.g. Klucel EF), 72-75% (w/w) active ingredient (e.g. Flibanserin) and 11-13% (w/w) talc applied in the range from 8 mg/cm$^2$ to 12 mg/cm$^2$, based on the specific surface area of the starting core;
- third layer: 63-72% (w/w) hydroxypropyl methylcellulose phthalate (e.g. HP 50), 20-25% (w/w) povidone (e.g. Kollidon 17), 4-6% glycerole monostearate and 4-6% (w/w) triethyl citrate applied in the range from 0.8 mg/cm$^2$ to 5 mg/cm$^2$, based on the specific surface area of the starting core.

The controlled release system of the present invention may be prepared according to conventionally known methods. The controlled release system may be prepared by the following method described hereinafter:

The core material containing the pH modifier may for example comprise crystals of the particular pH modifier(s) used or, more advantageously, roughly spherical particles of the desired size containing a defined amount of pH modifier(s), which can be produced by methods known and established in pharmaceutical technology.

The core material may be produced, in particular, by pan methods, on pelleting plates or by extrusion/spheronisation. Then the core material thus obtained may be divided into fractions of the desired diameter by screening. Suitable core material has preferably an average diameter of 0.4 to 1.5 mm, preferably 0.6 to 0.8 mm.

Subsequently, the optional insulating layer may be applied to the core material. This can be done by conventional methods, e.g. by applying an aqueous solution or dispersion of the water-soluble, pharmaceutically acceptable polymer(s), optionally with the addition of plasticizers, separating agents and/or pigments and/or other suitable additives, in a fluidised bed, in coating pans or in a conventional layer coating apparatus. If necessary the product can then be screened again.

Thereafter, the first layer may be applied. This can be done by conventional methods, e.g. by applying a solution or dispersion (aqueous-based or organic-based) of the water-insoluble pharmaceutically acceptable polymer(s), optionally with the addition of suitable additives, in a fluidised bed, in a coating pans or in conventional layer coating apparatus. If necessary the product can then be screened again.

Then, the active substance may be applied from a solution or dispersion preferably containing binder and optionally separating agent and/or other additives. The volatile solvent or dispersant is removed during or after the process by drying. The solvents or dispersants used in the process according to the present invention may be for example water, ethanol, isopropanol, acetone or mixtures of these solvents with one another. Emulsifiers or stabilizers may be present such as cetyl alcohol, Nonoxynol 100, oleic acid, polysorbates (polyethylene sorbitan fatty acid esters), sodium hydroxide, sodium lauryl sulphate, sorbic acid and the like.

The application of active substance to the core material may be carried out by established methods known in pharmaceutical technology, e.g. in coating pans, conventional layer coating apparatus or by the fluidised bed method. Then a further screening process may be carried out.

Subsequently a further optional (second) insulation layer may be provided on the second layer. Said insulating layer is composed as already described. This insulating layer may be present additionally or alternatively to the first insulating layer.

Afterwards the third layer can be produced by methods known and established in pharmaceutical technology. This can be done by conventional methods, e.g. by applying a dispersion of the pharmaceutically acceptable polymer(s) having anionic or no ionic groups, optionally with the addition of plasticizers and/or other suitable additives, in a fluidised bed, in coating pans or in a conventional layer coating apparatus. If necessary the product can then be screened again.

To reduce any increased abrasion during transfer into capsules and/or to increase the shelf life or in order to add a further diffusion barrier, the controlled release system may finally be coated with a coating (i.e. the optional fourth layer) preferably of a conventional pharmaceutical film forming agent, plasticizer and optionally pigment. This may be done by conventional methods.

The controlled release system of the present invention can be of any suitable size and shape, for example round, oval, polygonal or pillow-shaped, and optionally bear non-functional surface markings.

When core material with an average diameter of 0.4-1.5 mm is used, the process described above produces for example pellets containing active substance, which can then be packed into capsules. To do this, a number of these units corresponding to the required dosage may be packed into capsules in a standard capsule filling machine. Suitable hard capsules include, for example, hard gelatine capsules or hard capsules of hydroxypropyl methylcellulose (HPMC). Alternatively these units may be compressed together with suitable binders into tablets which disintegrate in the stomach releasing the coated pellets.

In case tablets or capsules are provided they may be packed in bottles or blisters well known in the art. Among such blisters are such being made of polyvinylchloride or polyvinylidene chloride. Aluminum-blisters are also possible. Bottles may be made of poylpropylene or polyethylene for example. Other conventional packaging materials are possible, too.

The controlled release systems of the invention, for example present in capsules or in another suitable dosage form, can be packaged in a container, accompanied by a package insert providing pertinent information such as, for example, dosage and administration information, contraindications, precautions, drug interactions and adverse reactions.

BRIEF DESCRIPTION OF THE DRAWINGS

In the drawings

FIG. 1 shows a controlled release system of prior art wherein anions of salts are present in the core 1. Thereon a modulating layer 2 is provided which is composed of a neutral polymer layer such as Eudragit® NE. The modulating layer 2 is layered with a drug layer 3 and further coated with controlled release layer 4 of methacrylate polymer having quaternary ammonium ions such as Eudragit® RL/RS as outmost layer. The release mechanism is based on the ion exchanger Eudragit® RS in the outmost layer 4 which changes the permeability and thus controls the solubility of the drug.

Figure 1:
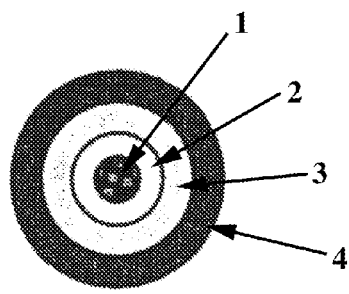
FIG. 1 shows a sectional schematic and enlarged view of a controlled release system of the prior art.

In contrast to prior art as illustrated in FIG. 1 the function of the controlled release system of the present invention is not based on the change of the permeability of the outmost layer but mainly on ionic interactions between the core and, for example, the first layer and third layer. According to the present invention the outmost layer has no cationic groups such as quaternary ammonium groups so that the mechanism of release is totally different. Furthermore, the controlled release system of the present invention does function in vitro and in vivo.

Figure 2:
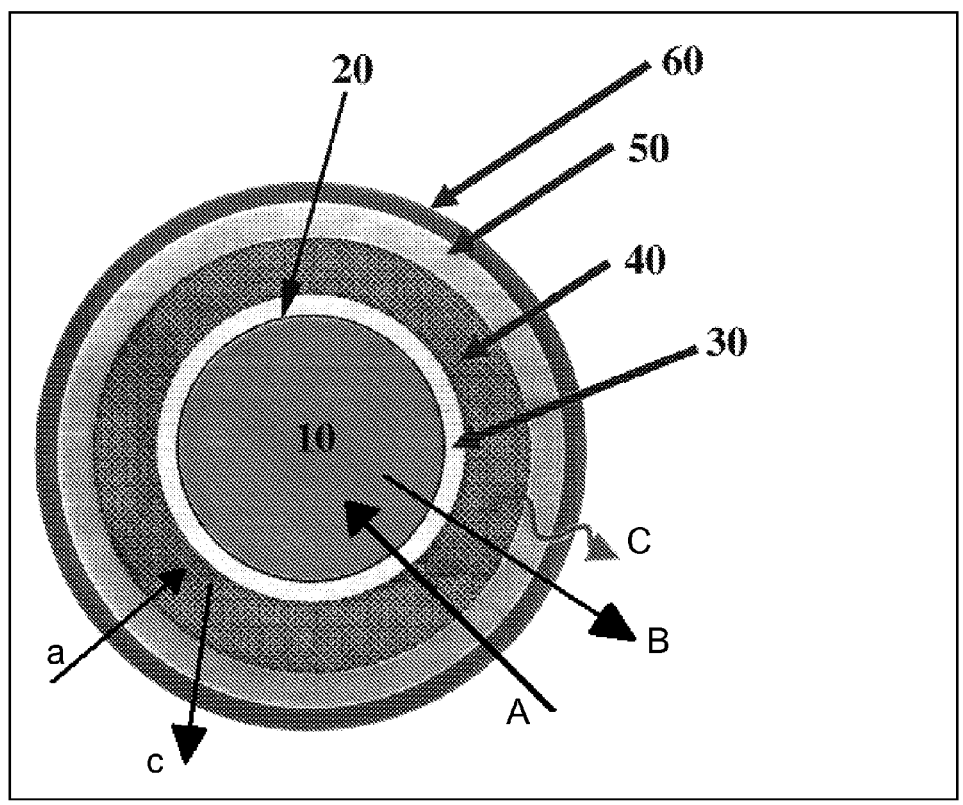
FIG. 2 shows a sectional schematic and enlarged view of a preferred embodiment of the controlled release system according to the present invention.

FIG. 2 shows a sectional schematic and enlarged view of a preferred embodiment of a controlled release system according to the present invention. The preferably bead-shaped/spherical core portion 10 contains or consists of one or more pharmaceutically acceptable organic acids and/or bases and/or buffers and optionally suitable excipients. This is optionally followed by a layer which separates the core 10 from the subsequent layers, the so-called insulating layer 20. The insulating layer 20 in turn, or the core material 10 in the absence of an insulating layer 20, is surrounded by a first layer 30 containing or consisting of one or more water-insoluble polymers and optional excipients, on which is applied the active substance layer 40, which are both preferably also spherical, which itself be surrounded by the third layer 50 containing or consisting of one or more polymers having no cationic groups in the molecules and optional excipients, on which one or more coatings 60 may be provided to increase the abrasion resistance and shelf life of the controlled release system of the present invention or to control the release of the active ingredient at low pH-values (e.g. pH 1).

Further, the release of the controlled release system of the present invention is schematically represented in FIG. 2 by the gastric liquid (pH about 1), for example the fluid penetrates into the formulation (a) dissolving the active substance which for example might be a weak base. The release rate of the active substance is then controlled by the fourth layer (60) Moving into the small intestine the pH raises towards 6, thus for this example the fourth layer would be dissolved. The enteric liquid will penetrate the core hence, the dissolved pH modifier penetrates layer 1 (30) enhancing dissolution of the active substance at controlled pH (B), Finally, the third layer controls drug release.

FIGS. 3 to 15 will be described in detail in the Examples.

The advantages of the present invention are manifold:

The invention shows well controlled release of the pharmaceutically active substance(s), i.e. the controlled release system according to the present invention exhibit improved bioavailability of the active substance(s) contained therein due to a release profile being almost pH-independent.

Furthermore, the pH modifier(s) in the core is separated from the active substance core which provides a number of advantages:

A desired controlled release system which can inhibit the dissolution and release of the active substance for a predetermined period of time can be obtained and the release of the active substance after the initiation of dissolving can be reliably achieved, the desired level in blood of the active substance for a long period of time can be realized. Undesirable interactions between pH modifier(s) and active substance(s) in spite of the use of pH modifier(s) to improve the solubility may be prevented. The controlled release system of the present invention remains sufficiently stable when stored. Only after the administration of the formulation system does the pH modifier(s) dissolve and produce a micro climate in which the active substance can dissolve.

The invention described will now be illustrated by the Examples which follow various other embodiments and will become apparent to the skilled person from the present specification. However, it is expressly pointed out that the Examples and description are intended solely as an illustration and should not be regarded as restricting the invention.

In the following the invention is exemplified by formulations for pellets. However, the present invention is not limited to pellets, but other dosage forms are possible. The active ingredient for each formulation given is each of the compounds mentioned above. Each of the examples shall be combined with each of the listed compounds. This means each of the examples given below shall count for each of the compounds listed above. The preferred active substances as defined above, define the preferred formulations.

The information given will allow the skilled person in the art to manufacture the desired dosage form of any of the aforementioned active ingredients with the therapeutically necessary dosage.

Each of the dosage forms may have a total weight of 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg or even more or less.

EXAMPLES

Example 1

In the following a preferable process to manufacture the controlled release system of the present invention is exemplarily described. However, the process steps are not intended to be of limitative character at all.

The preparation of the controlled release system of the present invention in the following Example usually takes place over 6 steps:

step a): preparation of core material containing pH modifier;
step b): preparation of the first layer;
step c): preparation of the second layer containing active substance;
step d): preparation of the third layer;
step e): preparation of the fourth layer; and
step f): packing into capsules.

The steps will be described in the following in detail:
Step a)
Preparation of Core Material Containing pH Modifier
a1) 1 part by weight of gum arabic is dissolved with stirring in 4 parts by weight of purified water at 50° C. 5 parts by weight of tartaric acid are then dissolved in this solution with stirring.

8.3 parts by weight of tartaric acid crystals with an average particle size of 0.4 to 0.6 mm are placed in a suitable coating apparatus fitted with an air inlet and exhaust and the container is set rotating. At an air inlet temperature of 60°-80° C. The tartaric acid crystals are sprayed with the solution of tartaric acid-gum arabic in intermittent operation and sprinkled with a total of 6.7 parts by weight of powdered tartaric acid, so as to produce roughly spherical particles.

The spherical tartaric acid core material is then dried in the rotating container at an air inlet temperature of 60°-80° C.

The core material is fractionated using a tumbler screening machine with perforated plates having nominal mesh sizes of 0.6 and 0.8 mm. The product fraction of between 0.6 and 0.8 mm is used in subsequent processing.

a2) Isolation of the Core Material Containing Tartaric Acid 0.5 parts of hypromellose are dissolved in 10.1 parts of 96% ethanol. Further 0.5 parts of talc together with 0.01 parts of polydimethylsiloxane are dispersed into the hypromellose/ethanol solution with stirring. This insulating dispersion is sprayed onto the tartaric acid cores (a1) in a fluidised bed processing plant, 21 parts by weight of tartaric acid-containing core material are sprayed with the hypromellose/talc dispersion at an air entry temperature of 35°-40° C. by the under-bed spraying method. The isolated tartaric acid-containing core material is then dried in the circulating air dryer at 40° C. for 8 hours. To remove lumps the dried isolated tartaric acid-containing core material is screened through a screen with a nominal mesh size of 1.0 mm. The fraction of material (particle size less than 1 mm) is further processed.

The other steps b) to f) are illustrated in flow diagrams shown in FIGS. 3 to 7.

Step b)

Preparation of the First Layer

Figure 3:
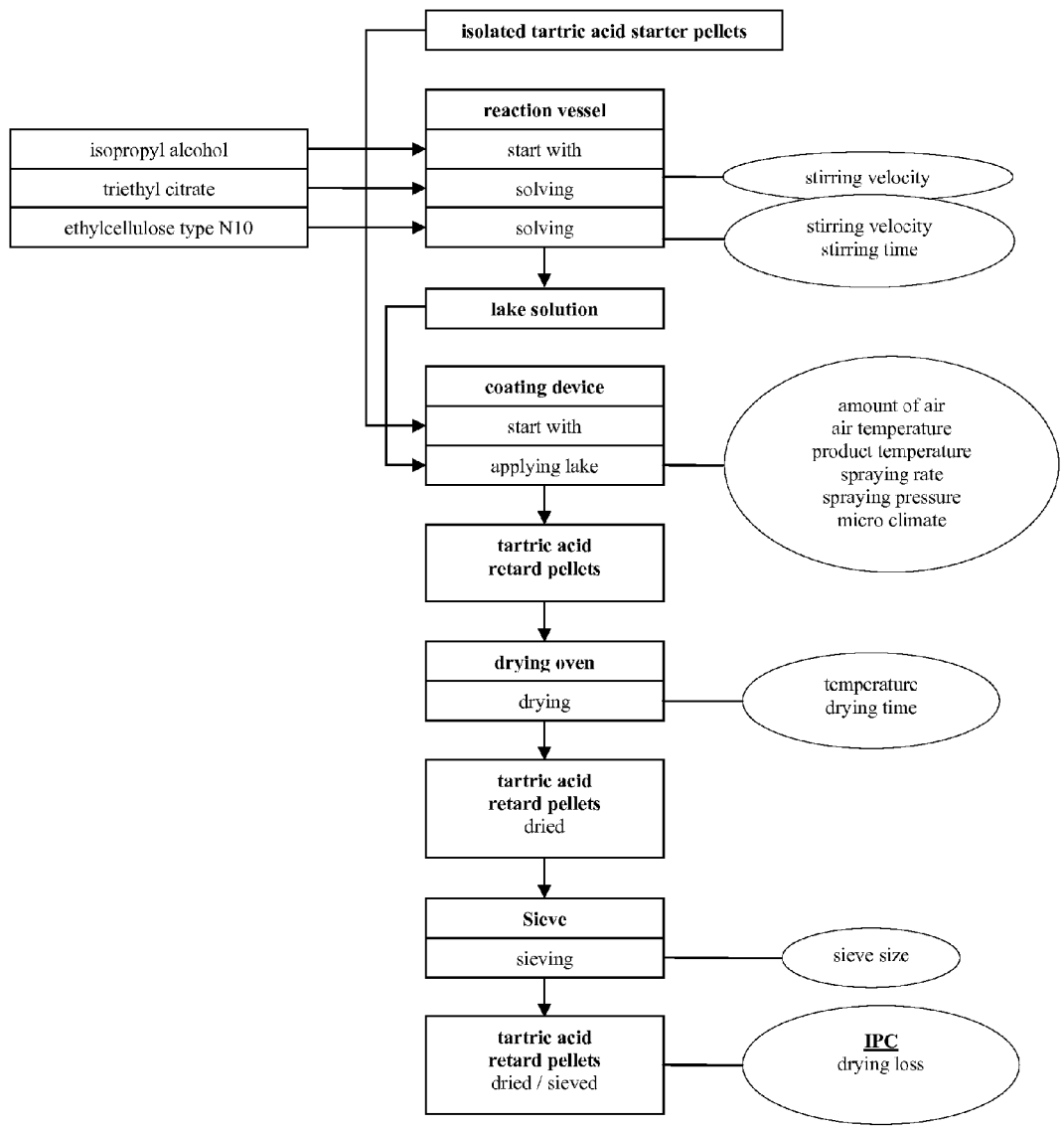
FIGS. 3 to 14 represent flow diagrams illustrating a preferred method for the manufacturing of the controlled release system according to the present invention.

As illustrated in FIG. 3 it may be started with a core material prepared as described above, for example a core material containing tartaric acid, the first layer was subsequently prepared as follows:

1. Preparation of the Lake Solution

Isopropyl alcohol (4730.00 g) was charged in a suitable reaction vessel and then triethyl citrate (45.00 g) and ethylcellulose type N10 (225.00 g) were added in portions and dispersed in this solution with stirring. The solution was stirred at room temperature overnight. It was obtained a lake solution.

2. Spraying of the Obtained Lake Solution

Then the obtained lake solution was sprayed onto 1500 g of tartaric starter pellets (insulated). To this purpose the pellets were placed in a suitable coating apparatus fitted with an air inlet and exhaust. At an air inlet temperature of about 45° C. the tartaric pellets were sprayed with the lake solution in continuous operation so as to produce roughly spherical particles. The following conditions were used:

| | |
|---|---|
| inlet air quantity | 100 m³/h |
| spraying rate | 2-18 g/min |
| spray pressure | 0.6 bar, |
| micro climate | 0.2 bar |
| nozzle diameter | 1.2 mm |
| spray time | about 7 h |
| product temperature | 30-40° C. |

The virtually spherical product obtained was then dried in a suitable drying device at 40° C. for 12 hours. The product was fractionated using a suitable screening machine with perforated plates having nominal mesh sizes of 1.0 mm.

Step c)

Preparation of the Second Layer Containing the Active Substance

1. Preparation of the Lake Solution

Figure 4:
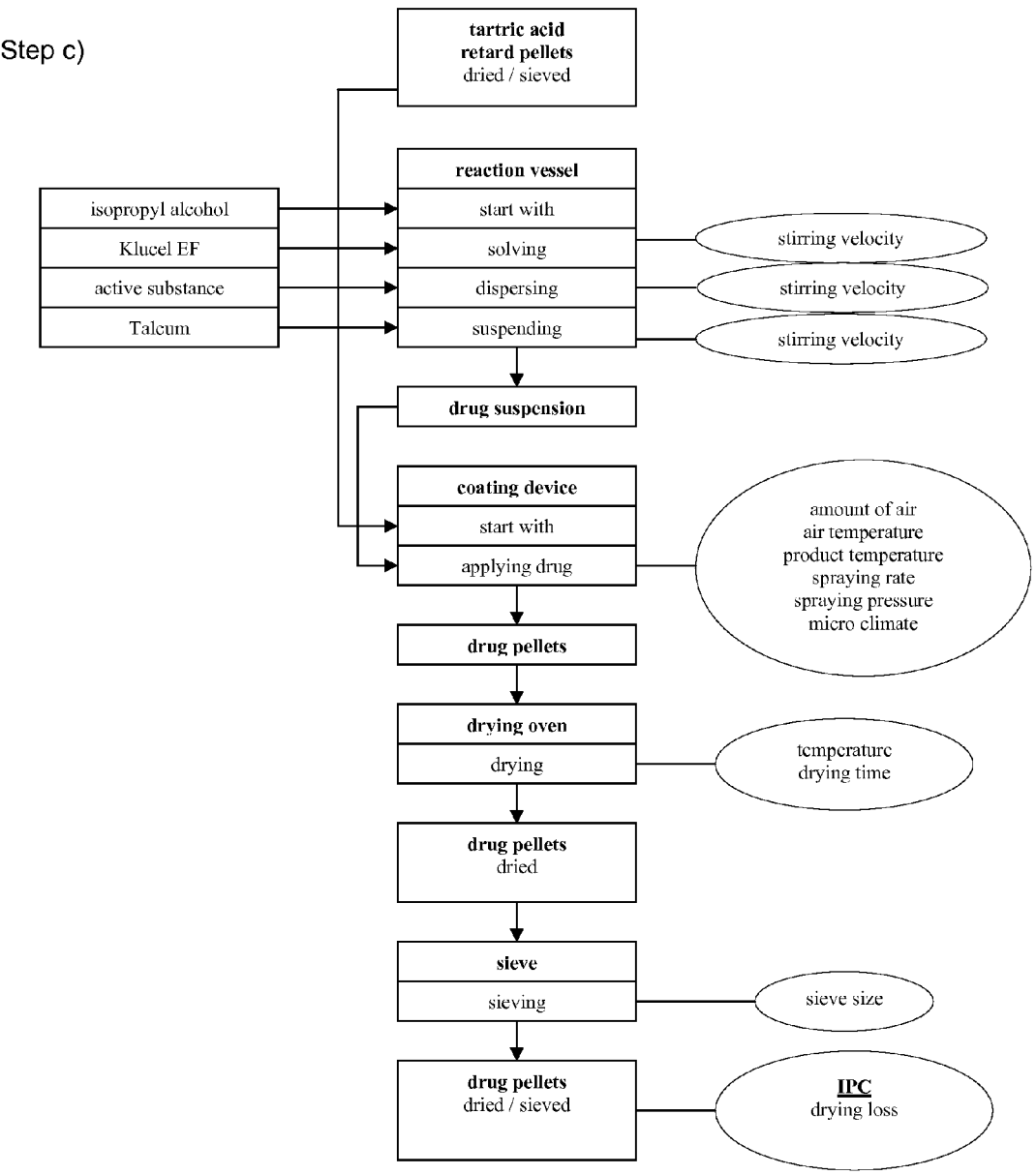

As illustrated in FIG. 4 isopropyl alcohol (1360.00 g) was charged in a suitable reaction vessel and then Klucel EF (binder; 50.00 g), an active substance (250.00 g) added in portions and talc (40.00 g) were dispersed in this solution with stirring. The solution was stirred at room temperature overnight. It was obtained a lake solution.

2. Spraying of the Obtained Lake Solution

Then the lake solution was sprayed onto 778 g of the product obtained in step b). To this purpose the product was placed in a suitable coating apparatus fitted with an air inlet and exhaust. At an air inlet temperature of about 25° C. the product was sprayed with the lake solution in continuous operation and sprinkled so as to produce roughly spherical particles. The following conditions were used:

| | |
|---|---|
| inlet air quantity | 100 m³/h |
| spraying rate | 1-10 g/min |
| spray pressure | 0.6 bar, |
| micro climate | 0.2 bar |
| nozzle diameter | 1.2 mm |
| spray time | about 5 h |
| product temperature | 20-25° C. |

The virtually spherical product obtained was then dried in a suitable drying device at 40° C. for 12 hours. The product was fractionated using a suitable screening machine with perforated plates having nominal mesh sizes of 1.25 mm.

Step d)

Preparation of the Third Layer

1. Preparation of the Lake Solution

Figure 5:
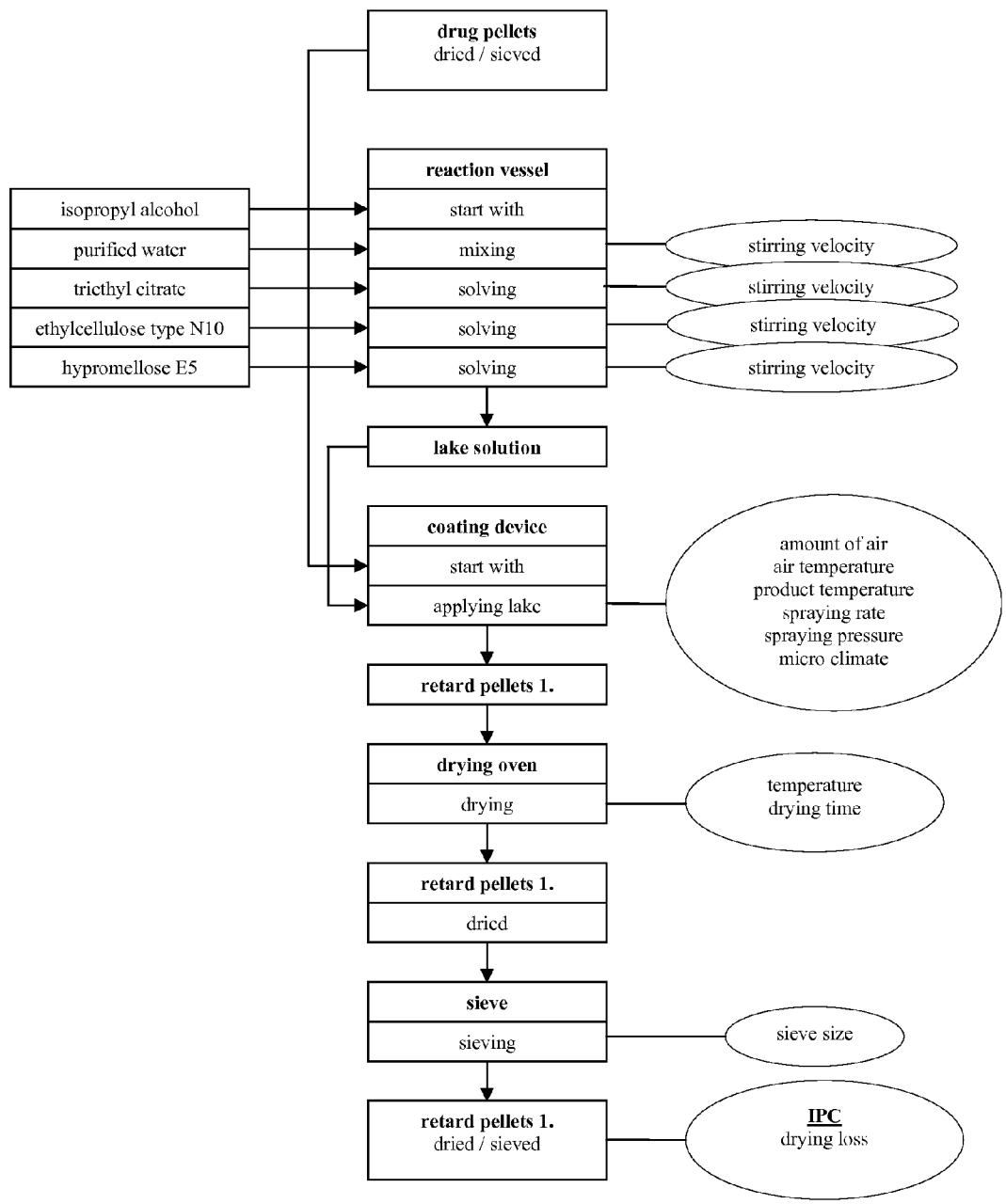

As illustrated in FIG. 5 isopropyl alcohol (421.70 g) was charged in a suitable reaction vessel and then purified water (74.42 g), triethyl citrate (1.65 g), ethylcellulose type N10 (16.50 g) and hypromellose (Methocel E5, 16.50 g) were added in portions and dispersed in this solution with stirring. The solution was stirred at room temperature overnight. It was obtained a lake solution.

2. Spraying of the Obtained Lake Solution

Then the lake solution was sprayed onto 1100 g of the product obtained in step c). To this purpose the pellets were placed in a suitable coating apparatus fitted with an air inlet and exhaust. At an air inlet temperature of about 35° C. the product was sprayed with the lake solution in continuous operation and sprinkled so as to produce roughly spherical particles. The following conditions were used:

| | |
|---|---|
| inlet air quantity | 70 m³/h |
| spraying rate | 2-6 g/min |
| spray pressure | 0.6 bar, |
| micro climate | 0.2 bar |
| nozzle diameter | 1.2 mm |
| spray time | about 4 h |
| product temperature | 30-35° C. |

The virtually spherical product obtained was then dried in a suitable drying device at 40° C. for 12 hours. The product was fractionated using a suitable screening machine with perforated plates having nominal mesh sizes of 1.25 mm.

Step e)
Preparation of the Fourth Layer
1. Preparation of the Lake Solution

Figure 6:
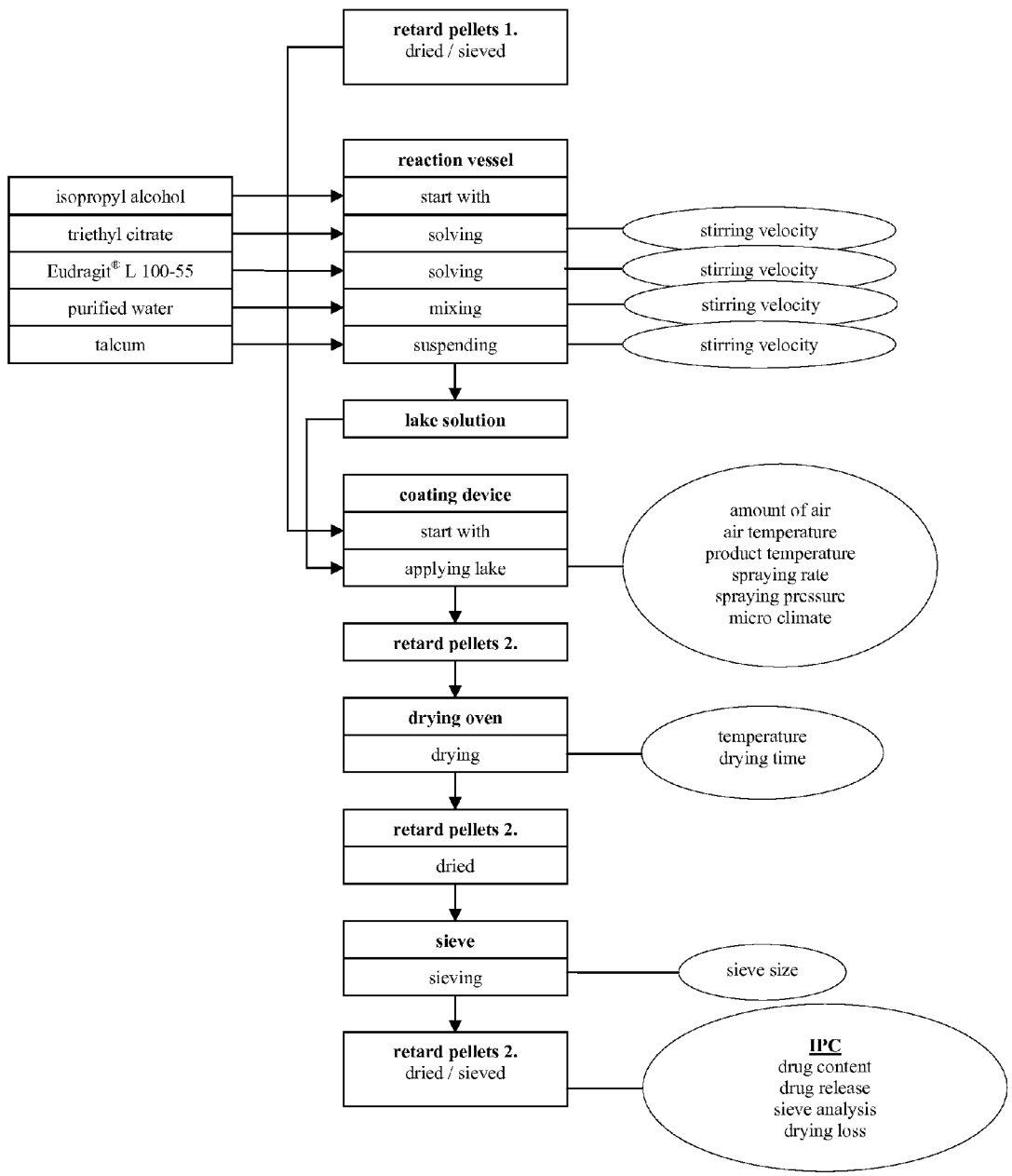

As illustrated in FIG. 6 isopropyl alcohol (341.36 g) was charged in a suitable reaction vessel and then triethyl citrate (1.25 g), Eudragit® L 100-55 (25.00 g) and purified water (46.550 g) were added in portions and dispersed in this solution with stirring. The solution was stirred at room temperature overnight. It was obtained a lake solution.

2. Spraying of the Obtained Lake Solution

Then talc (2.50 g) was suspended into the lake solution which was subsequently sprayed onto 1000.0 g of the product obtained in step d). To this purpose the pellets were placed in a suitable coating apparatus fitted with an air inlet and exhaust. At an air inlet temperature of about 35° C. the product was sprayed with the lake solution in continuous operation and sprinkled so as to produce roughly spherical particles. The following conditions were used:

| | |
|---|---|
| inlet air quantity | 70 m$^3$/h |
| spraying rate | 2-6 g/min |
| spray pressure | 0.6 bar, |
| micro climate | 0.2 bar |
| nozzle diameter | 1.2 mm |
| spray time | about 3 h |
| product temperature | 30-35° C. |

The virtually spherical product obtained was then dried in a suitable drying device at 25° C. for 12 hours. The product was fractionated using a suitable screening machine with perforated plates having nominal mesh sizes of 1.25 mm.

Step f)
Packing into Capsules

Figure 7:
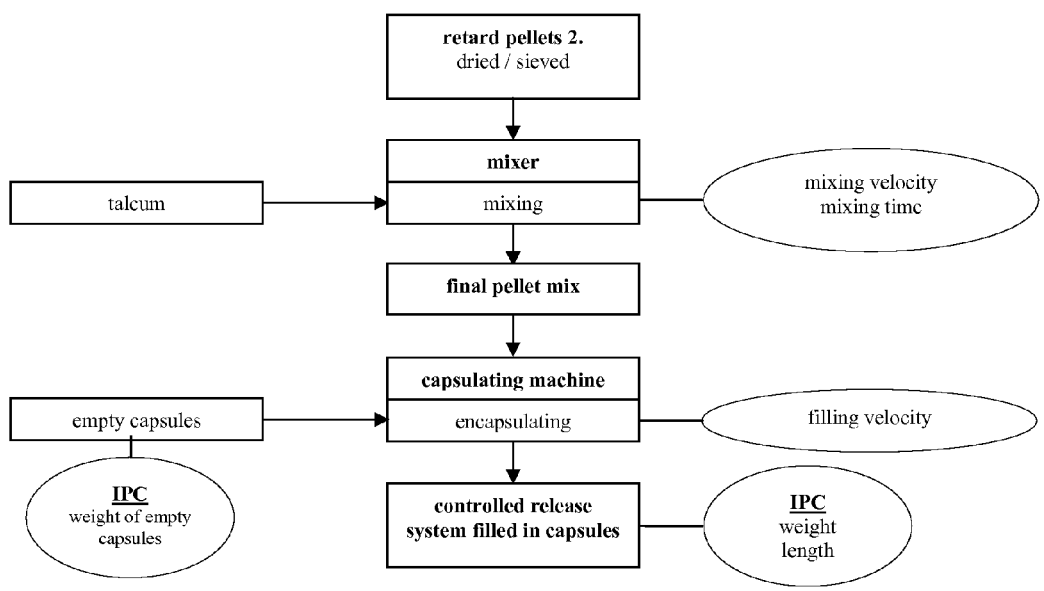

As illustrated in FIG. 7 a quantity of pellets containing active substance was mixed with talc to obtain the final mixture which was subsequently packed into size capsules such as hard gelatine capsules size 0 using a capsule filling machine.

During or after any step usual Internal Process Controls (IPC) were employed.

Example 2

The preparation of the controlled release system of the present invention in the following Example usually takes place over 6 steps:
step a): preparation of core material containing pH modifier;
step b): preparation of the first layer;
step c): preparation of the second layer containing active substance;
step d): preparation of an insulating layer;
step e): preparation of the third layer; and
step f): packing into capsules.

The same process steps a), b) and c) were performed as described above in Example 1. Then the process was continued as follows:

Step d)
Insulating Layer
1. Preparation of the Lake Solution

Figure 8:
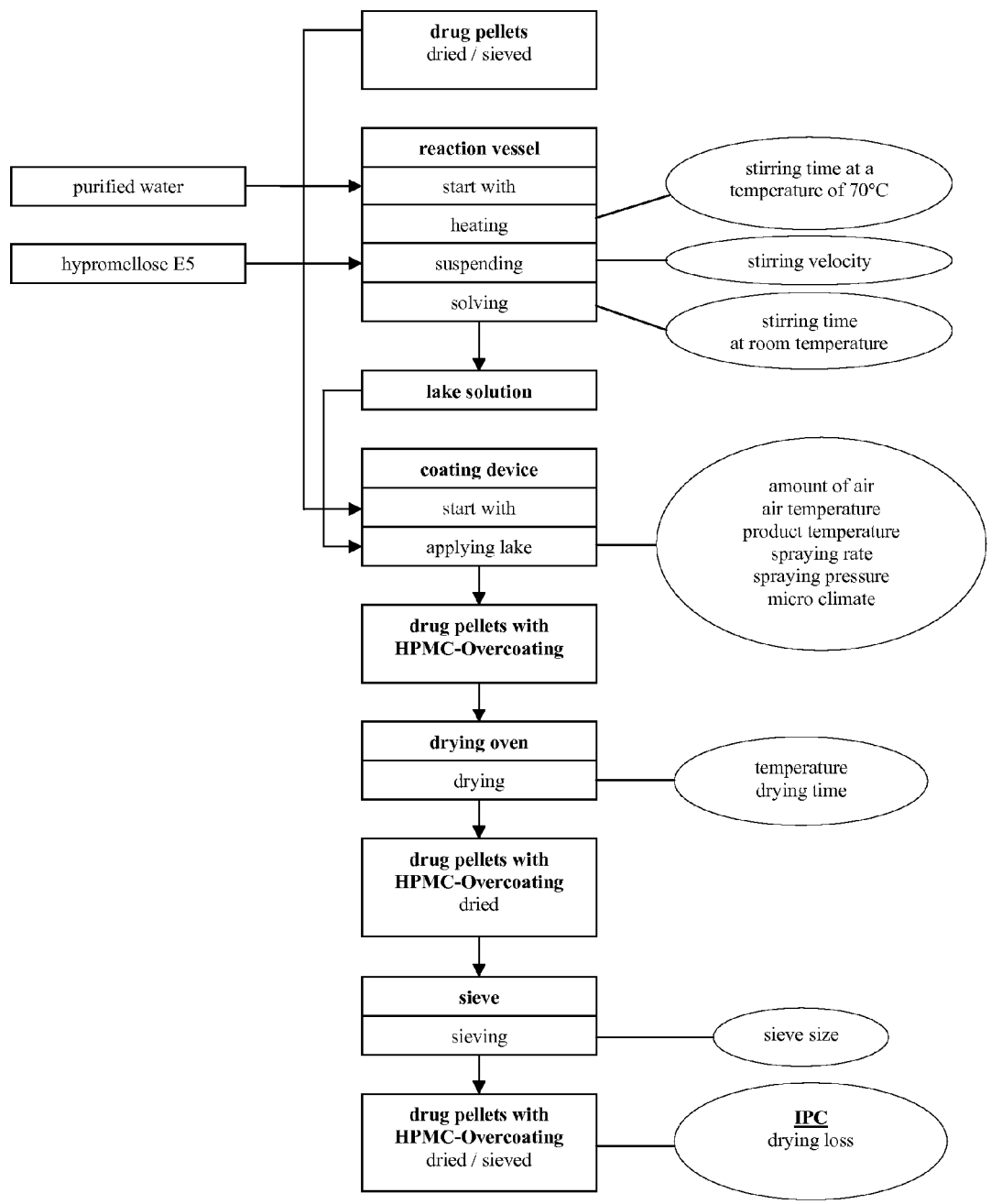

As illustrated in FIG. 8 purified water (466.88 g) was charged in a suitable reaction vessel and then hypromellose (Methocel E5) (22.00 g) at a temperature of 70 to 75° C. added in portions and dispersed in this solution with stirring. The solution was cooled and stirred at room temperature overnight. It was obtained a lake solution.

2. Spraying of the Obtained Lake Solution

Then the lake solution was sprayed onto 1100.0 g of the product obtained in step c). To this purpose the pellets were placed in a suitable coating apparatus fitted with an air inlet and exhaust. At an air inlet temperature of about 40° C. the product was sprayed with the lake solution in continuous operation and sprinkled so as to produce roughly spherical particles. The following conditions were used:

| | |
|---|---|
| inlet air quantity | 70 m$^3$/h |
| spraying rate | 1-6 g/min |
| spray pressure | 0.6 bar, |
| micro climate | 0.2 bar |
| nozzle diameter | 1.2 mm |
| spray time | about 3 h |
| product temperature | 30-35° C. |

The virtually spherical product obtained was then dried in a suitable drying device at 40° C. for 12 hours. The product was fractionated using a suitable screening machine with perforated plates having nominal mesh sizes of 1.25 mm.

Step e)
Preparation of the Third Layer
1. Preparation of the Lake Solution

Figure 9:
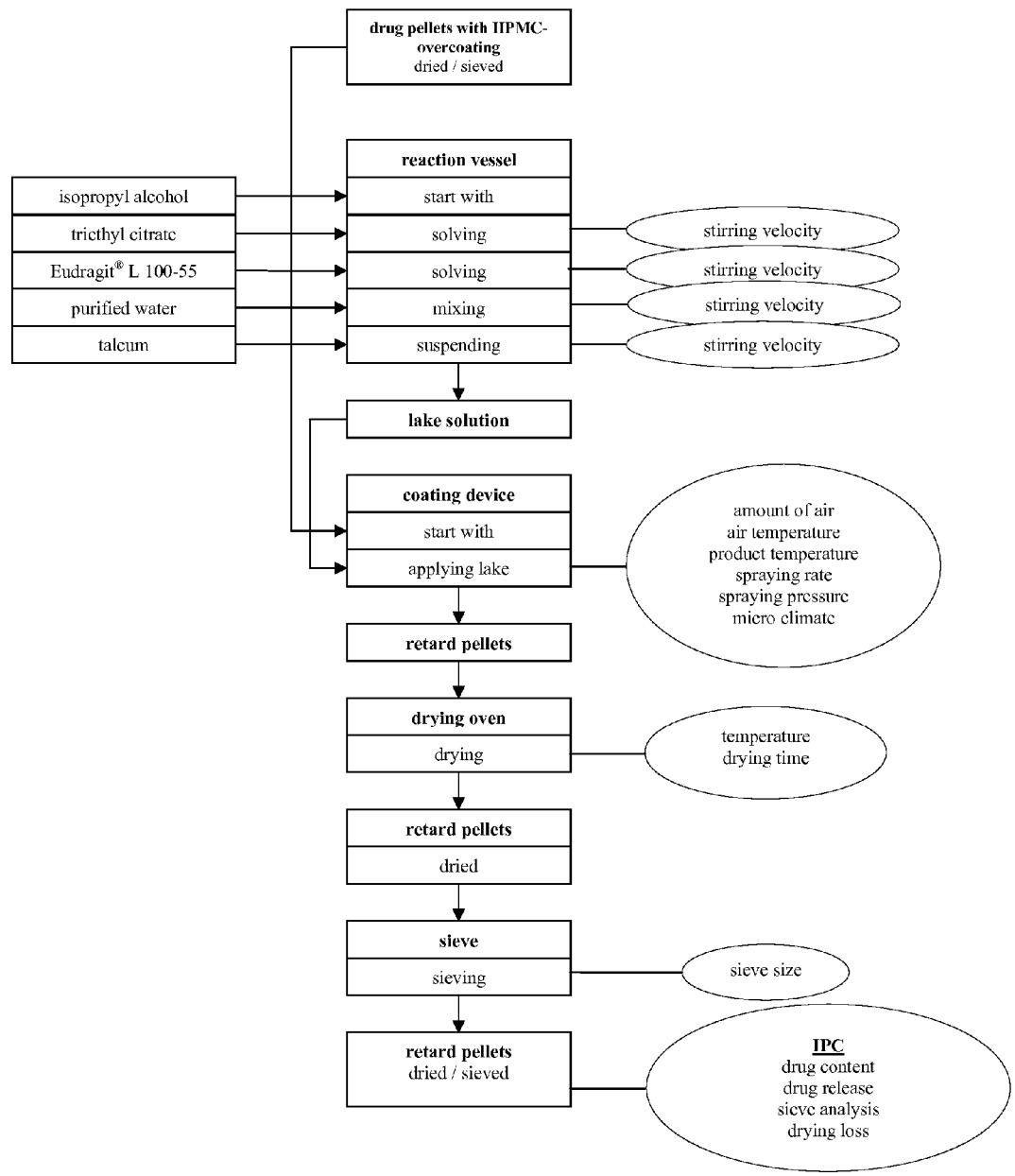

As illustrated in FIG. 9 isopropyl alcohol (341.36 g) was charged in a suitable reaction vessel and then triethyl citrate (1.25 g), Eudragit® L 100-55 (25.00 g) and purified water (46.55 g) were added in portions and dispersed in this solution with stirring. The solution was stirred at room temperature overnight. It was obtained a lake solution.

2. Spraying of the Obtained Lake Solution

Then talc (2.50 g) was suspended into the lake solution which was subsequently sprayed onto 1000.0 g of the product obtained in step d). To this purpose the pellets were placed in a suitable coating apparatus fitted with an air inlet and exhaust. At an air inlet temperature of about 35° C. the product was sprayed with the lake solution in continuous operation and sprinkled so as to produce roughly spherical particles. The following conditions were used:

| | |
|---|---|
| inlet air quantity | 70 m$^3$/h |
| spraying rate | 2-6 g/min |
| spray pressure | 0.6 bar, |
| micro climate | 0.2 bar |
| nozzle diameter | 1.2 mm |
| spray time | about 3 h |
| product temperature | 30-35° C. |

The virtually spherical product obtained was then dried in a suitable drying device at 25° C. for 12 hours. The product was fractionated using a suitable screening machine with perforated plates having nominal mesh sizes of 1.25 mm.

Step f)
Packing into Capsules

Figure 10:
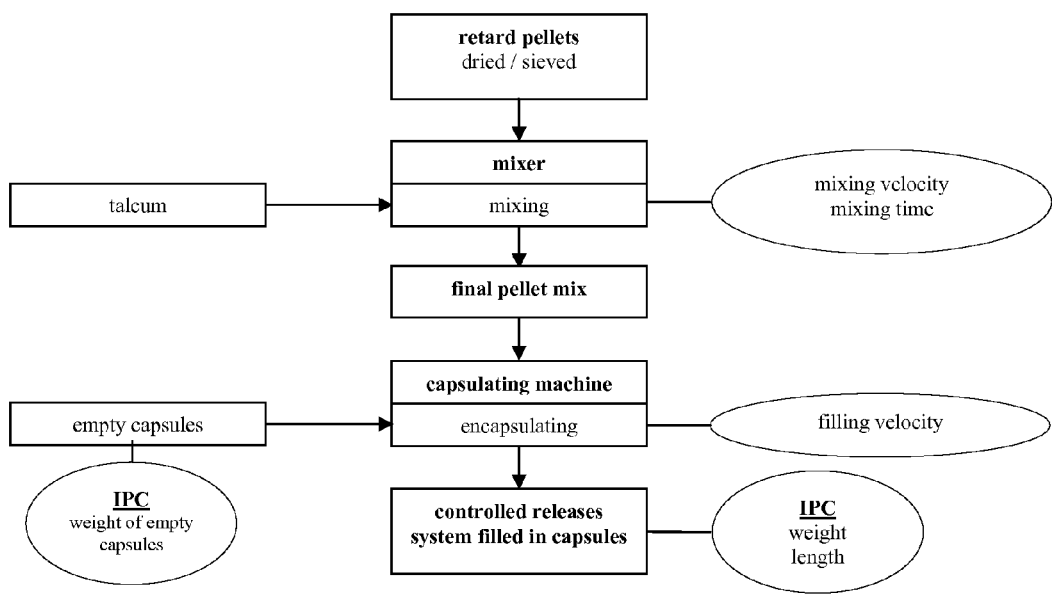

As illustrated in FIG. 10 a quantity of pellets containing active substance was mixed with talc to obtain the final mixture which was subsequently packed into size capsules such as hard gelatine capsules size 0 using a capsule filling machine.

During or after any step usual Internal Process Controls (IPC) were employed.

Example 3

In the following a preferable process to manufacture the controlled release system of the present invention is exemplarily described. However, the process steps are not intended to be of limitative character at all.

The preparation of the controlled release system of the present invention in the following Example usually takes place over 6 steps:
step a): preparation of core material containing pH modifier;
step b): preparation of the first layer;
step c): preparation of the second layer containing active substance;
step d): preparation of the third layer;
step e): packing into capsules.

The steps will be described in the following in detail:

Step a)
Preparation of Core Material Containing pH Modifier
a1) 1 part by weight of gum arabic is dissolved with stirring in 4 parts by weight of purified water at 50° C. 5 parts by weight of tartaric acid are then dissolved in this solution with stirring.

8.3 parts by weight of tartaric acid crystals with an average particle size of 0.4 to 0.6 mm are placed in a suitable coating apparatus fitted with an air inlet and exhaust and the container is set rotating. At an air inlet temperature of 60°-80° C. The tartaric acid crystals are sprayed with the solution of tartaric acid-gum arabic in intermittent operation and sprinkled with a total of 6.7 parts by weight of powdered tartaric acid, so as to produce roughly spherical particles.

The spherical tartaric acid core material is then dried in the rotating container at an air inlet temperature of 60°-80° C.

The core material is fractionated using a tumbler screening machine with perforated plates having nominal mesh sizes of 0.6 and 0.8 mm. The product fraction of between 0.6 and 0.8 mm is used in subsequent processing.

a2) Isolation of the Core Material Containing Tartaric Acid
1 part of hypromellose is dispersed in 9 parts of water at 90° C. and further dissolved with stirring cooling the dispersion to 20° C. This insulating solution is sprayed onto the tartaric acid cores (a1) in a fluidised bed processing plant, 1 part by weight of tartaric acid-containing core material is sprayed with the hypromellose solution at an air entry temperature of 45°-49° C. by the Wurster spraying method. The isolated tartaric acid-containing core material is then dried in the circulating air dryer at 40° C. for 12 hours. To remove lumps the dried isolated tartaric acid-containing core material is screened through a screen with a nominal mesh size of 1.0 mm. The fraction of material (particle size less than 1 mm) is further processed.

The other steps b) to e) are illustrated in flow diagrams shown in FIGS. 11 to 14.

Figure 11:
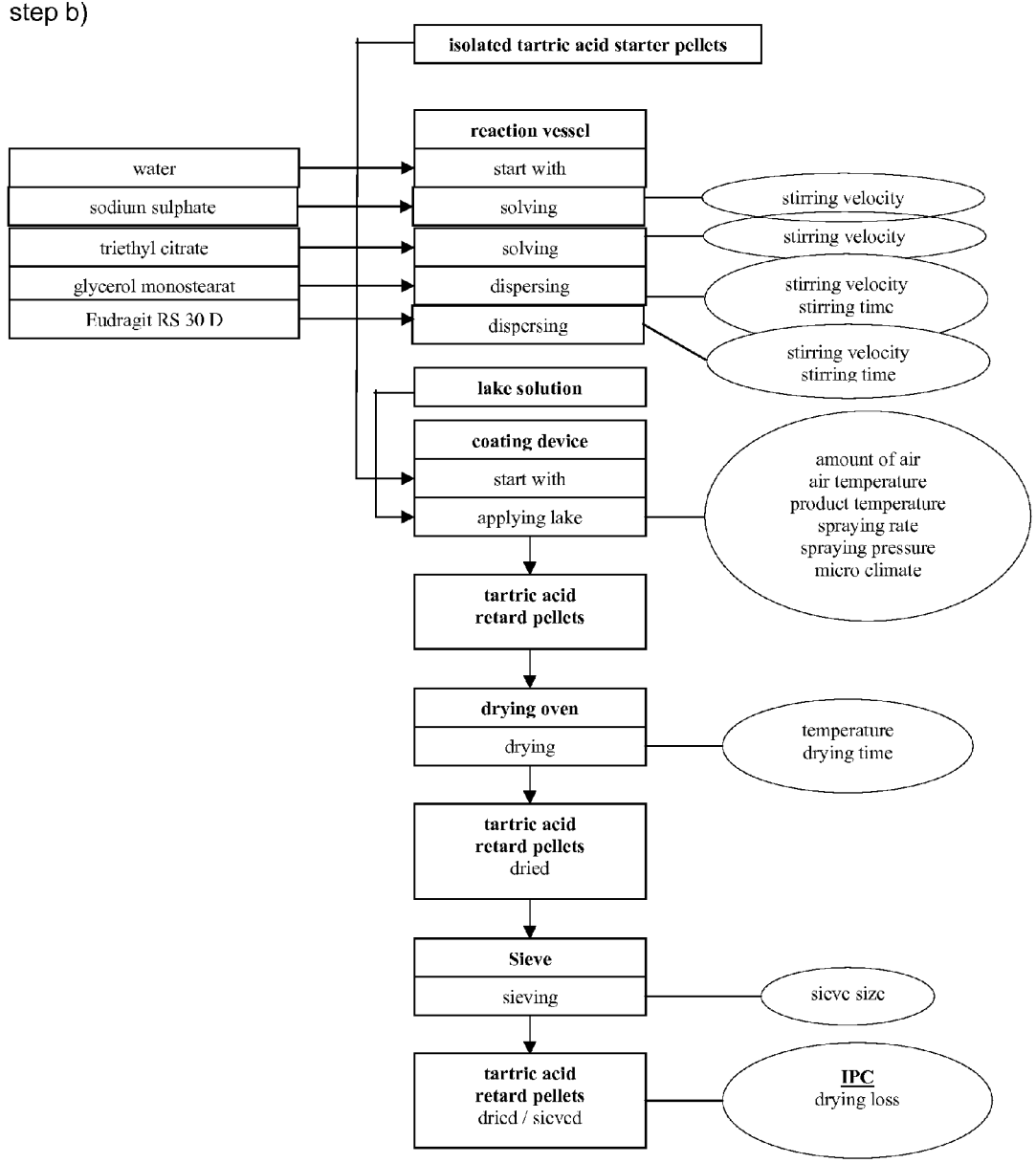

Step b)
Preparation of the First Layer
As illustrated in FIG. 11 it may be started with a core material prepared as described above, for example a core material containing tartaric acid, the first layer was subsequently prepared as follows:

1. Preparation of the Lake Solution
Purified water (1385.71 g) was charged in a suitable reaction vessel and then triethyl citrate (10.00 g), glycerol monostearate (10.00 g), sodium sulphate (8.83) and Eudragit RS 30 D (666.67 g) were added in portions and dispersed in this solution with stirring. The solution was stirred at room temperature overnight. It was obtained a lake solution.

2. Spraying of the Obtained Lake Solution
Then the obtained lake solution was sprayed onto 1000 g of tartaric starter pellets (insulated). To this purpose the pellets were placed in a suitable coating apparatus fitted with an air inlet and exhaust. At an air inlet temperature of about 40-48° C. the tartaric pellets were sprayed with the lake solution in continuous operation so as to produce roughly spherical particles. The following conditions were used:

| | |
|---|---|
| inlet air quantity | 90 m$^3$/h |
| spraying rate | 2-10 g/min |
| spray pressure | 1.2 bar, |
| nozzle diameter | 1.0 mm |
| spray time | about 7 h |
| product temperature | 30-35° C. |

The virtually spherical product obtained was then dried in a suitable drying device at 40° C. for 24 hours. The product was fractionated using a suitable screening machine with perforated plates having nominal mesh sizes of 1.0 mm.

Step c)
Preparation of the Second Layer Containing the Active Substance

Figure 12:
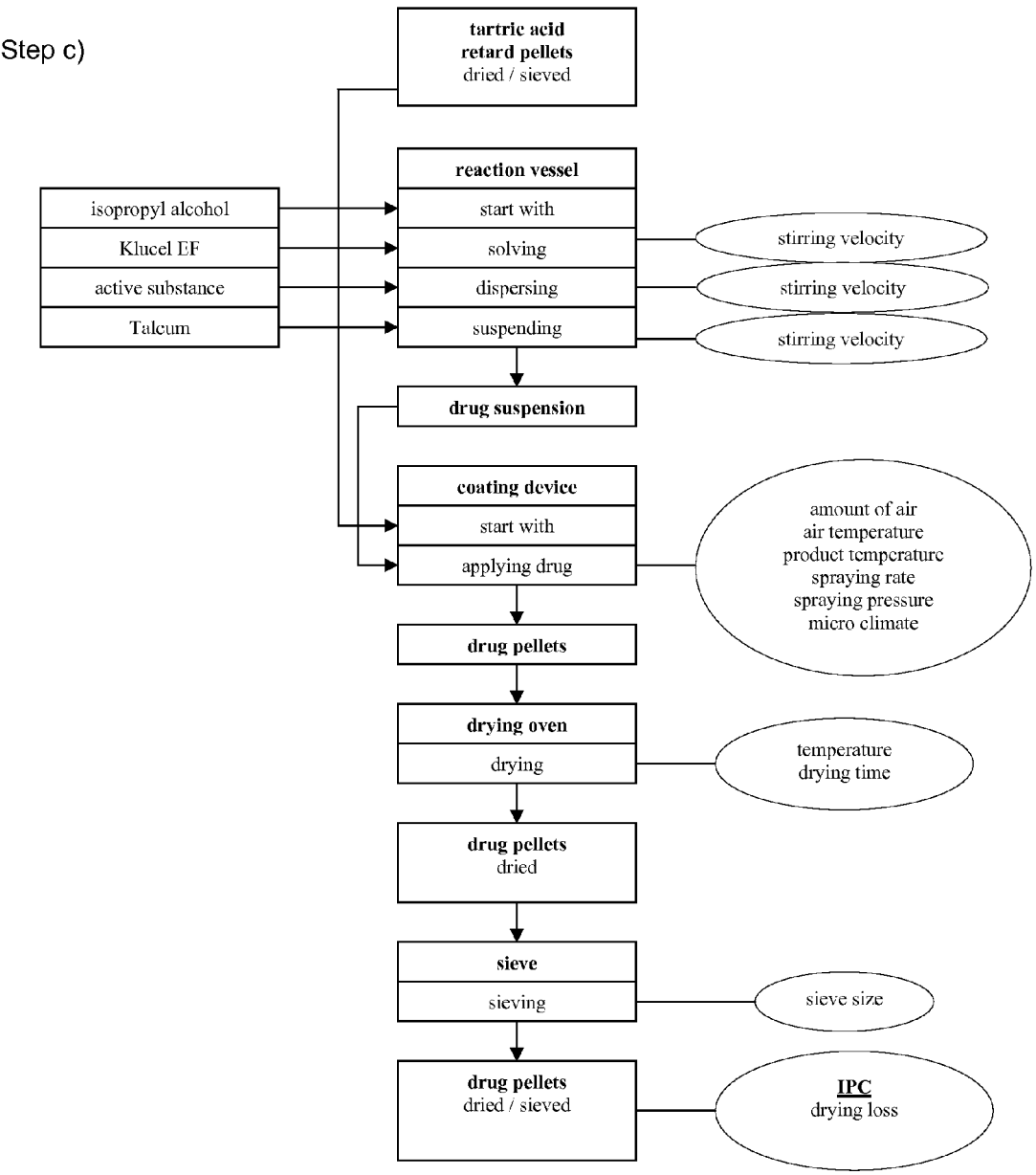

1. Preparation of the Lake Solution
As illustrated in FIG. 12 isopropyl alcohol (1360.00 g) was charged in a suitable reaction vessel and then Klucel EF (binder; 50.00 g), an active substance (250.00 g) added in portions and talc (40.00 g) were dispersed in this solution with stirring. The solution was stirred at room temperature overnight. It was obtained a lake solution.

2. Spraying of the Obtained Lake Solution
Then the lake solution was sprayed onto 778 g of the product obtained in step b). To this purpose the product was placed in a suitable coating apparatus fitted with an air inlet and exhaust. At an air inlet temperature of about 25° C. the product was sprayed with the lake solution in continuous operation and sprinkled so as to produce roughly spherical particles. The following conditions were used:

| | |
|---|---|
| inlet air quantity | 100 m$^3$/h |
| spraying rate | 1-10 g/min |
| spray pressure | 0.6 bar, |
| micro climate | 0.2 bar |
| nozzle diameter | 1.2 mm |
| spray time | about 5 h |
| product temperature | 20-25° C. |

The virtually spherical product obtained was then dried in a suitable drying device at 40° C. for 12 hours. The product was fractionated using a suitable screening machine with perforated plates having nominal mesh sizes of 1.25 mm.

Figure 13:
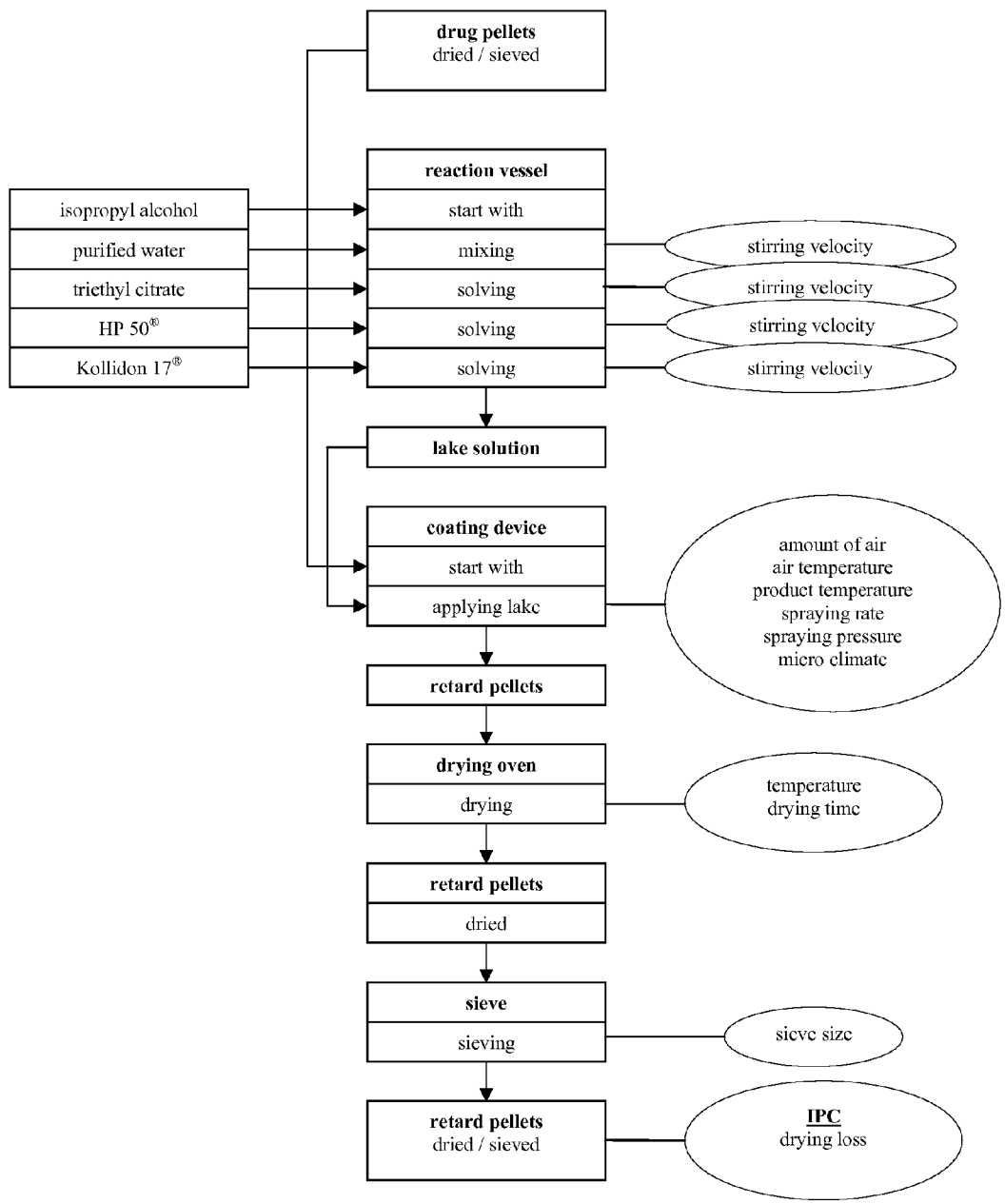

Step d)
Preparation of the Third Layer
1. Preparation of the Lake Solution
As illustrated in FIG. 13 isopropyl alcohol (33.09 g) was charged in a suitable reaction vessel and then purified water (7.79 g), triethyl citrate (0.12 g), glycerol monostearate (0.12 g), HP 50 (1.80 g) and Kollidon 17® (0.60 g) were added in portions and dispersed in this solution with stirring. The solution was stirred at room temperature overnight. It was obtained a lake solution.

2. Spraying of the Obtained Lake Solution
Then the lake solution was sprayed onto 30 g of the product obtained in step c). To this purpose the pellets were placed in a suitable coating apparatus fitted with an air inlet and exhaust. At an air inlet temperature of about 35° C. the product was sprayed with the lake solution in continuous operation and sprinkled so as to produce roughly spherical particles. The following conditions were used:

| | |
|---|---|
| inlet air quantity | 500 mbar |
| spraying rate | 0.3-0.5 g/min |
| spray pressure | 0.8 bar, |
| nozzle diameter | 0.3 mm |
| spray time | about 2 h |
| product temperature | 22-28° C. |

The virtually spherical product obtained was then dried in a suitable drying device at 40° C. for 12 hours. The product was fractionated using a suitable screening machine with perforated plates having nominal mesh sizes of 1.25 mm.

Step e)

Packing into Capsules

Figure 14:
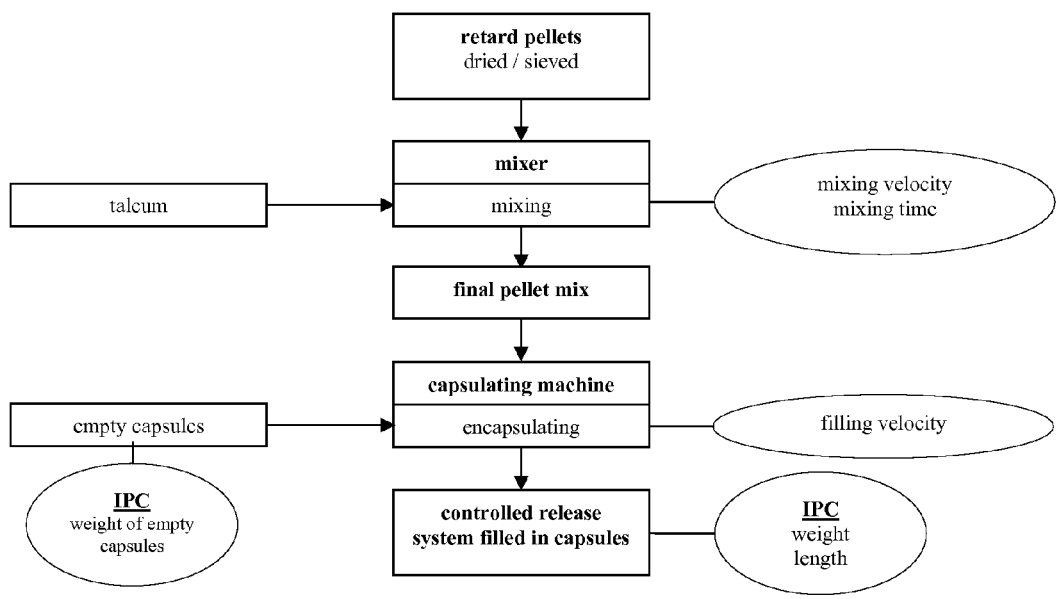

As illustrated in FIG. 14 a quantity of pellets containing active substance was mixed with talc to obtain the final mixture which was subsequently packed into size capsules such as hard gelatine capsules size 0 using a capsule filling machine.

During or after any step usual Internal Process Controls (IPC) were employed.

Example 4

Dissolution profiles of modified release formulations of each of examples 1 to 3 were evaluated and compared to an immediate release formulation (flibanserin IR tablet 100 mg) as described e.g. in WO 03-097058 (Example 3). Dissolution testing was performed in apparatus 2 (USP 30) equipped with a pH-sensor and a titration apparatus. The drug product is placed in a biphasic dissolution medium with a lower phosphate buffered aqueous phase of 550 ml which is covered by an upper lipophilic phase of 100 ml n-octanol facilitating sink conditions in the lipophilic phase throughout the dissolution test. Drug release in the test apparatus is performed at 37° C. and 50 rpm for 24 hours in an apparatus 2 dissolution vessel. Quantification of drug release is performed online using a UV-DAD spectrophotometer for each phase. During the dissolution test pH-values are adjusted in 3 stages using a suitable titration system: stage 1 pH 2 (1 h), stage 2 pH 5.5 (2+2 h), stage 3 pH 6.8 (19 h). pH adjustment is performed using 5 M sodium hydroxide solution. In order to test the drug products ability to release the active ingredients at pH 5.5 in combination with the incorporated pH modifier, a decreased pH value in stage 2 (pH<5.5) is readjusted to the initial value after 2 hours. All dissolution profiles display the total drug dissolved in aqueous and organic phase together.

Figure 15:
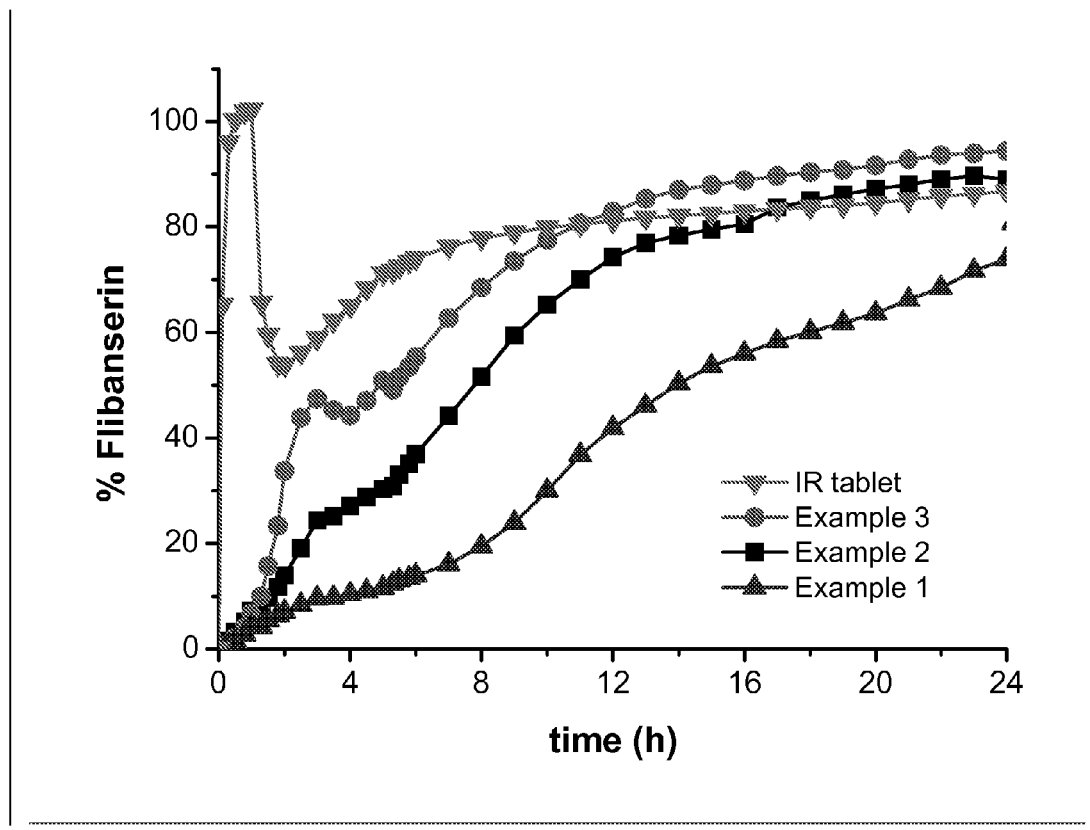
FIG. 15 shows the results of a in-vitro dissolution profiles of three different modified release formulations according to the invention compared to one non-modified release formulation as more fully described in Example 4

Data are shown in FIG. 15. During the first hour in pH 2 at which the active ingredient displays good solubility, all examples proofed to prevent dose dumping. In contrast the IR tablet released the entire dose within 20 min at the first stage of pH 2 for 1 hour. At the beginning of the second stage (pH 5.5) the absorption of active ingredient dissolved in the aqueous phase at pH 2 (stage 1) into the octanol phase is not completed hence, the dissolved fraction of active ingredient in the aqueous phase is susceptible to precipitate at the pH change from 2 to 5.5. This phenomenon is highly pronounced for the IR tablet in the combined dissolution/absorption test however, is not of in vivo relevance for the IR tablet, for the AUC of the IR tablet is determined by the early drug release at low pH in the stomach. In contrast the advantageous modified release formulations showed various drug release rates controlled by the prototypes especially at pH values (5.5-6.8) where the aqueous solubility of the active ingredient is poor.

What is claimed is:

1. A pharmaceutical controlled release system for administration of active substances with pH-dependent solubilities, comprising:
   a) a core material comprising one or more pharmaceutically acceptable pH modifiers, wherein at least one pharmaceutically acceptable pH modifier is an organic acid;
   b) a first insulating layer, provided on the core material, comprising one or more pharmaceutically acceptable water soluble polymers;
   c) a second layer comprising a pharmaceutically acceptable water-insoluble (poly(ethyl acrylate/methyl methacrylate/trimethylammonioethyl methacrylate chloride) polymer having either a 1:2:0.1 or 1:2:0.2 ratio of ethyl acrylate to methyl methacrylate to trimethylammonioethyl methacrylate chloride monomers;
   d) a third layer comprising at least one active substance having a pH-dependent solubility;
   e) a fourth layer comprising one or more pharmaceutically acceptable polymers having anionic or no ionic groups; and
   f) optionally a fifth layer.

2. The pharmaceutical controlled release system according to claim 1, wherein the system is for oral administration.

3. The pharmaceutical controlled release system according to claim 1, wherein the core material further comprises one or more binders and optionally one or more other excipients.

4. The pharmaceutical controlled release system according to claim 1, wherein the core material further includes one or more additional pH modifier(s) which comprises one or more pharmaceutically acceptable buffers.

5. The pharmaceutical controlled release system according to claim 1, wherein the pH modifier(s) is in solid or liquid form.

6. The pharmaceutical controlled release system according claim 1, wherein the one or more pharmaceutically acceptable organic acids selected from the group consisting of acetic acid, ascorbic acid, tartaric acid, glutaric acid, malic acid, fumaric acid, citric acid, lactic acid, adipic acid and succinic acid or combinations thereof.

7. The pharmaceutical controlled release system according to claim 1, wherein the core material has an average particle size of 0.4 to 1.5 mm.

8. The pharmaceutical controlled release system according to claim 1, wherein the second layer comprises one or more water-insoluble polymers, optionally one or more plasticizers, optionally one or more separating agents, optionally one or more pigments, and optionally other excipients.

9. The pharmaceutical controlled release system according to claim 1, wherein the fourth layer comprises one or more polymers having anionic or no ionic groups, one or more plasticizers, optionally one or more separating agents, and optionally other excipients.

10. The pharmaceutical controlled release system according to claim 9, wherein the polymer having anionic or no ionic groups contained in the fourth layer comprises ethylcellulose; hydroxypropyl methylcellulose phthalate; a poly(methacrylic acid/ethylacrylate) polymer having a 1:1 ratio of methacrylic acid to ethylacrylate monomers; or mixtures thereof.

11. The pharmaceutical controlled release system according to claim 1, wherein the fourth layer further comprises a pore former.

12. The pharmaceutical controlled release system according to claim 11, wherein the pore former comprises methylcellulose, hydroxypropyl methylcelluloses, hydroxypropyl cellulose, hydroxyethyl cellulose, povidone, or a poly(butyl methacrylate/ (2-dimethylaminoethyl) methacrylate/methyl methacrylate) polymer having a 1:2:1 ratio of butyl methacrylate to (2-dimethylaminoethyl) methacrylate to methyl methacrylate monomers.

13. The pharmaceutical controlled release system according to claim 1, wherein the third layer comprises one or more active substances having pH-dependent solubility, one or more binders, and optionally one or more other excipients.

14. The pharmaceutical controlled release system according to claim 1, wherein the first insulating layer comprises one or more water-soluble polymers, optionally one or more plasticizers, optionally one or more separating agents, optionally one or more pigments, and optionally other excipients.

15. The pharmaceutical controlled release system according to claim 1, wherein another insulating layer is provided on the third layer.

16. The pharmaceutical controlled release system according to claim 1, wherein the controlled release system further comprises the optional fifth layer.

17. The pharmaceutical controlled release system according to claim 16, wherein the optional fifth layer comprises one or more polymers having anionic or no ionic groups, one or more plasticizers, optionally one or more separating agents, and optionally other excipients.

18. The pharmaceutical controlled release system according to claim 17, wherein the polymer contained in the optional fifth layer comprises hydroxypropyl methylcellulose phthalate; a poly(methacrylic acid/ethylacrylate) having a 1:1 ratio of methacrylic acid to ethylacrylate monomers; or mixtures thereof.

19. The pharmaceutical controlled release system according to claim 1, wherein the optional fifth layer further comprises a pore former.

20. The pharmaceutical controlled release system according to claim 1, wherein the application quantities for the layers present, based on the specific surface area of the starting core, are as follows:
first insulating layer:
in the range from 0.05 to 5 mg/cm$^2$;
second layer:
in the range from 0.1 to 15 mg/cm$^2$;
third layer:
in the range from 0.1 to 20 mg/cm$^2$;
fourth layer:
in the range from 0.1 to 15 mg/cm$^2$, and
optional fifth layer:
if present in the range from 0.1 to 15 mg/cm$^2$.

21. The pharmaceutical controlled release system according to claim 1, wherein the active substance is flibanserin.

22. A process for preparing a pharmaceutical controlled release system according to claim 1 containing an active substance with pH-dependent solubility characteristics comprising the steps of:
step a) producing the core material from one or more pharmaceutically acceptable pH modifiers wherein at least one pharmaceutically acceptable pH modifier is an organic acid, optionally with the addition of one or more binders and/or other excipients, by pan methods, on pelleting plates or by extrusion/spheronisation;
step b) optionally applying an a first insulating layer comprising one or more water-soluble pharmaceutically acceptable polymers, optionally with the addition of one or more plasticizers, one or more separating agents and/or one or more pigments, and/or other excipients;
step c) applying a first second layer comprising one or more water-insoluble pharmaceutically acceptable polymers a water-insoluble (poly(ethyl acrylate/methyl methacrylate/trimethylammonioethyl methacrylate chloride) polymer having either a 1:2:0.1 or 1:2:0.2 ratio of ethyl acrylate to methyl methacrylate to trimethylammonioethyl methacrylate chloride monomers, optionally with the addition of one or more plasticizers and/or one or more separating agents and/or one or more pigments and/or other excipients;
step d) applying a second third layer comprising at least one active substance having a pH-dependent solubility from a solution or dispersion optionally containing one or more binders and/or one or more separating agents and/or other excipients, and simultaneously or subsequently drying to eliminate the solvent or dispersing agent;
step e) optionally applying an insulating layer comprising one or more water-soluble pharmaceutically acceptable polymers, optionally with the addition of one or more plasticizers and/or one or more separating agents and/or one or more pigments and/or other excipients;
step f) applying a third fourth layer comprising one or more pharmaceutically acceptable polymers having anionic or no ionic groups optionally with the addition of one or more plasticizers, one or more separating agents and/or one or more pigments and/or other excipients;
step g) optionally applying a fourth fifth layer, optionally with addition of one or more plasticizers and/or one or more pigments and/or other excipients; and
step h) optionally packing the controlled release system containing active substance thus obtained into capsules.

23. The process for preparing a pharmaceutical controlled release system according to claim 22, wherein the active substance is flibanserin.

24. A method of treating a condition in a mammal treatable by flibanserin comprising the administration of a therapeutically effective amount of the pharmaceutical controlled release system according to claim 21 to the mammal.

25. The method according to claim 24, wherein flibanserin is administered in a dosage range between 0.1 to 400 mg per day.

26. The pharmaceutical controlled release system according to claim 1, wherein the second layer is directly on the first insulating layer.

\* \* \* \* \*